United States Patent
Alanine et al.

(10) Patent No.: US 6,835,732 B2
(45) Date of Patent: Dec. 28, 2004

(54) BENZOTHIAZOLE DERIVATIVES WITH ACTIVITY AS ADENOSINE RECEPTOR LIGANDS

(75) Inventors: Alexander Alanine, Schlierbach (FR); Alexander Flohr, Basel (CH); Aubry Kern Miller, San Francisco, CA (US); Roger David Norcross, Rheinfelden (CH); Claus Riemer, Freiburg (DE)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 10/310,508

(22) Filed: Dec. 5, 2002

(65) Prior Publication Data

US 2003/0125318 A1 Jul. 3, 2003

Related U.S. Application Data

(62) Division of application No. 09/881,252, filed on Jun. 14, 2001, now Pat. No. 6,521,754.

(30) Foreign Application Priority Data

Jun. 21, 2000 (EP) .............................................. 00113219

(51) Int. Cl.$^7$ .................... A61K 31/426; A61K 31/496; A61K 31/4535; A61K 31/5377
(52) U.S. Cl. .............................. 514/235.5; 514/254.02; 514/321; 514/326; 514/367
(58) Field of Search .............................. 514/235.5, 326, 514/321, 367, 254.02

(56) References Cited

U.S. PATENT DOCUMENTS

| | | |
|---|---|---|
| 3,725,428 A | 4/1973 | Janiak |
| 4,028,374 A | 6/1977 | Pelosi, Jr. et al. |
| 5,099,021 A | 3/1992 | Worther et al. |

FOREIGN PATENT DOCUMENTS

| | | |
|---|---|---|
| DE | 1953149 | 5/1970 |
| EP | 0199400 A | 10/1986 |
| EP | 295 656 | 12/1988 |
| EP | 0343893 | 11/1989 |
| EP | 040444 A | 12/1990 |
| EP | 427 963 | 5/1991 |
| EP | 0604657 | 7/1994 |
| FR | 2 753 970 a | 4/1998 |
| GB | 1 345 552 A | 1/1974 |
| GB | 1 538 822 A | 1/1979 |
| WO | WO 99/37630 | 1/1990 |
| WO | WO 99/24035 | 5/1999 |
| WO | WO 00/18767 | 4/2000 |
| WO | WO 00/27819 A | 5/2000 |
| WO | WO 01/19360 A2 | 9/2000 |

OTHER PUBLICATIONS

The Merck Index 12$^{th}$ Ed., (1996) p. 506.
Arch. Pharm. Med. Chem., 332 (1999) pp. 39–41.
J. Med. Chem., 39 (1996) pp. 1164–1171.
J. Med. Chem., 42 (1999) pp. 706–721.
J. Med. Chem., 41 (1998) pp. 2835–2845.
J. Med. Chem., 41 (1998) pp. 3186–3201.
J. Med. Chem., 41 (1998) pp. 2126–2133.
Bioorganic & Medicinal Chemistry, 6 (1998) pp. 619–641.
Bioorganic & Medicinal Chemistry, 6 (1998) pp. 707–719.
Patent Abstracts of Japan, vol. 1999, No. 10, JP 11 130761a.
Pandeya, Surendra N. et al., Indian Drugs (1985), 23(3), 146–51 XP0080000199.
Daidone, G. et al., vol. 44, No. 5 (1989) pp. 465–473, XP001053114.

*Primary Examiner*—Taofiq Solola
(74) *Attorney, Agent, or Firm*—George W. Johnston; Patricia S. Rocha-Tramaloni; Kimberly J. Prior

(57) ABSTRACT

The present invention relates to substituted benzothiazole derivitives and to their pharmaceutically acceptable salts useful for the treatment of diseases related to the adenosine receptor.

18 Claims, No Drawings

BENZOTHIAZOLE DERIVATIVES WITH ACTIVITY AS ADENOSINE RECEPTOR LIGANDS

This is a divisional application of U.S. patent application Ser. No. 09/881,252, filed Jun. 14, 2001 now U.S. Pat. No. 6,521,754.

FIELD OF INVENTION

The present invention is related to benzothiazole compounds, and more particularly to benzothiazole dervitives showing activity as adenosine receptor ligands.

BACKGROUND

Adenosine modulates a wide range of physiological functions by interacting with specific cell surface receptors. The potential of adenosine receptors as drug targets was first reviewed in 1982. Adenosine is related both structurally and metabolically to the bioactive nucleotides adenosine triphosphate (ATP), adenosine diphosphate (ADP), adenosine monophosphate (AMP) and cyclic adenosine monophosphate (cAMP); to the biochemical methylating agent S-adenosyl-L-methione (SAM); and structurally to the coenzymes NAD, FAD and coenzym A; and to RNA. Together adenosine and these related compounds are important in the regulation of many aspects of cellular metabolism and in the modulation of different central nervous system activities.

The receptors for adenosine have been classified as $A_1$, $A_{2A}$, $A_{2B}$ and $A_3$ receptors, belonging to the family of G protein-coupled receptors. Activation of adenosine receptors by adenosine initiates signal transduction mechanism. These mechanisms are dependent on the receptor associated G protein. Each of the adenosine receptor subtyps has been classically characterised by the adenylate cyclase effector system, which utilises cAMP as a second messenger. The $A_1$ and $A_3$ receptors, coupled with $G_i$ proteins inhibit adenylate cyclase, leading to a decrease in cellular cAMP levels, while $A_{2A}$ and $A_{2B}$ receptors couple to $G_s$ proteins and activate adenylate cyclase, leading to an increase in cellular cAMP levels. It is known that the $A_1$ receptor system include the activation of phospholipase C and modulation of both potassium and calcium ion channels. The $A_3$ subtype, in addition to its association with adenylate cyclase, also stimulates phospholipase C and so activates calcium ion channels.

The $A_1$ receptor (326–328 amino acids) was cloned from various species (canine, human, rat, dog, chick, bovine, guinea-pig) with 90–95% sequence identify among the mammalian species. The $A_{2A}$ receptor (409–412 amino acids) was cloned from canine, rat, human, guinea pig and mouse. The $A_{2B}$ receptor (332 amino acids) was cloned from human and mouse with 45% homology of human $A_{2B}$ with human $A_1$ and $A_{2A}$ receptors. The $A_3$ receptor (317–320 amino acids) was cloned from human, rat, dog, rabbit and sheep.

The $A_1$ and $A_{2A}$ receptor subtypes are proposed to play complementary roles in adenosine's regulation of the energy supply. Adenosine, which is a metabolic product of ATP, diffuses from the cell and acts locally to activate adenosine receptors to decrease the oxygen demand ($A_1$) or increase the oxygen supply ($A_{2A}$) and so reinstate the balance of energy supply: demand within the tissue. The actions of both subtyps is to increase the amount of available oxygen to tissue and to protect cells against damage caused by a short term imbalance of oxygen. One of the important functions of endogenous adenosine is preventing damage during traumas such as hypoxia, ischaemia, hypotension and seizure activity.

Furthermore, it is known that the binding of the adenosine receptor agonist to mast cells expressing the rat $A_3$ receptor resulted in increased inositol triphosphate and intracellular calcium concentrations, which potentiated antigen induced secretion of inflammatory mediators. Therefore, the $A_3$ receptor plays a role in mediating asthmatic attacks and other allergic responses.

Adenosine is also a neuromodulator, possessing global importance in the modulation of molecular mechanisms underlying many aspects of physiological brain function by mediating central inhibitory effects. An increase in neurotransmitter release follows traumas such as hypoxia, ischaemia and seizures. These neurotransmitters are ultimately responsible for neural degeneration and neural death, which causes brain damage or death of the individual. The adenosine $A_1$ agonists which mimic the central inhibitory effects of adenosine may therefore be useful as neuroprotective agents. Adenosine has been proposed as an endogenous anticonvulsant agent, inhibiting glutamate release from excitory neurons and inhibiting neuronal firing. Adenosine agonists therefore may be used as antiepileptic agents. Adenosine antagonists stimulate the activity of the CNS and have proven to be effective as cognition enhancers. Selective $A_{2a}$-antagonists have therapeutic potential in the treatment of various forms of dementia, for example in Alzheimer's disease and are useful as neuroprotective agents. Adenosine $A_{2a}$-receptor antagonists inhibit the release of dopamine from central synaptic terminals and stimulate locomotor activity and consequently improve Parkinsonian symptoms. The central activities of adenosine are also implicated in the molecular mechanism underlying sedation, hypnosis, schizophrenia, anxiety, pain, respiration, depression and substance abuse. Drugs acting at adenosine receptors therefore have therapeutic potential as sedatives, muscle relaxants, antipsychotics, anxiolytics, analgesics, respiratory stimulants and antidepressants, and they may be used in the treatment of ADHD (attention deficit hyperactivity disorder).

An important role for adenosine in the cardiovascular system is as a cardioprotective agent. Levels of endogenous adenosine increase in response to ischaemia and hypoxia, and protect cardiac tissue during and after trauma (preconditioning). Adenosine agonists thus have potential as cardioprotective agents.

Adenosine modulates many aspects of renal function, including renin release, glomerular filtration rate and renal blood flow. Compounds, which antagonise the renal affects of adenosine, have potential as renal protective agents. Furthermore, adenosine $A_3$ and/or $A_{2B}$ antagonists may be useful in the treatment of asthma and other allergic responsesor and in the treament of diabetes mellitus and obesity.

Numerous documents describe the current knowledge on adenosine receptors, for example the following publications:

Bioorganic & Medicinal Chemistry, 6, (1998), 619–641,
Bioorganic & Medicinal Chemistry, 6, (1998), 707–719,
J. Med. Chem., (1998), 41, 2835–2845,
J. Med. Chem., (1998), 41, 3186–3201,
J. Med. Chem., (1998), 41, 2126–2133,
J. Med. Chem., (1999), 42, 706–721,
J. Med. Chem., (1996), 39, 1164–1171,
Arch. Pharm. Med. Chem., 332, 39–41, (1999).

SUMMARY

The present invention is a method of treatment of a person having a disease state treatable by modulation of the adenosine $A_{2a}$ receptor by administering to a person in need of such treatment an effective amount of a compound of the formula $$\underset{R^4}{\underset{R^3}{\overset{R^2}{\overset{R^1}{\bigcirc}}}}\underset{S}{\overset{N}{\bigcirc}}\underset{H}{\overset{X}{\bigvee}}R$$

I wherein $R^1$ is hydrogen, lower alkyl, lower alkoxy, benzyloxy, cycloalkyloxy, halogen, hydroxy or trifluoromethyloxy;

$R^2$, $R^3$ are independently from each other hydrogen, halogen, lower alkyl or lower alkyloxy;

$R^4$ is hydrogen, lower alkyl, lower alkenyl, halogen, —C(O)OH, —C(O)-lower alkyl, —C(O)-halogen-lower alkyl, —CH(OH)-halogen-lower alkyl, —C(O)O-lower alkyl, —NHC(O)-lower alkyl, —(CH$_2$)$_n$—OH, or is phenyl, which is optionally attached to the benzo group via the linker —(O)$_m$—(CH$_2$)$_n$— and is unsubstituted or substituted by N(R$^5$)(R$^6$), halogen, alkoxy or nitro, or is 2,3-dihydro-1H-indolyl, azepan-1-yl, [1,4]oxazepan-4-yl, or is a five or six membered aromatic or non aromatic heterocycle, which may be attached to the benzo group via the linker —(O)$_m$—(CH$_2$)$_n$ or —N=C(CH$_3$)— and is unsubstituted or substituted by one or two group(s) R$^7$, wherein R$^7$ is defined below;

R is (a) phenyl, unsubstituted or substituted by lower alkyl, halogen-lower alkyl, lower alkoxy, cyano, nitro, —C(O)H, —C(O)OH or by the following groups —(CH$_2$)$_n$—C(O)—N(R$^5$)—(CH$_2$)$_o$-lower alkoxy,
—(CH$_2$)$_n$O-halogen-lower alkyl,
—(CH$_2$)$_n$O—(CH$_2$)$_{n+1}$—O-lower alkyl,
—S(O)$_2$—N(R$^5$)—(CH$_2$)$_n$—O-lower alkyl,
—(CH$_2$)$_n$—OR$^5$,
—(CH$_2$)$_n$N(R$^5$)—(CH$_2$)$_o$-lower alkoxy,
—(CH$_2$)$_n$N[(CH$_2$)$_o$-lower alkoxy]$_2$,
—(CH$_2$)$_n$N(R$^5$)(R$^6$),
—(CH$_2$)$_n$N[S(O)$_2$CH$_3$]$_2$,
—(CH$_2$)$_n$N[R$^5$][S(O)$_2$CH$_3$],
—(CH$_2$)$_n$N(R$^5$)—(CH$_2$)$_o$NR$^5$R$^6$,
—(CH$_2$)$_n$N(R$^5$)-lower alkenyl,
—(CH$_2$)$_n$N(R$^5$)—(CH$_2$)$_o$-cycloalkyl,
—(CH$_2$)$_n$N(R$^5$)—C(O)O-lower alkyl,
—(CH$_2$)$_n$—S—(CH$_2$)$_n$—N(R$^5$)(R$^6$),
—(CH$_2$)$_n$N(R$^5$)—(CH$_2$)$_o$—S-lower alkyl,
—S(O)$_2$—N(R$^5$)(R$^6$),
—(CH$_2$)$_n$N(R$^5$)—S(O)$_2$CH$_3$
—(CH$_2$)$_n$N(R$^5$)—(CH$_2$)$_o$-phenyl,
—(CH$_2$)$_n$N(R$^5$)—(CH$_2$)$_o$—OH,
—(CH$_2$)$_n$N(R$^5$)—(CH$_2$)$_o$—CH(OH)—CF$_3$,
—(CH$_2$)$_n$N(R$^5$)—(CH$_2$)$_o$—CF$_3$,
—(CH$_2$)$_n$N(R$^5$)—(CH$_2$)$_o$—O—CH(OH)—C$_6$H$_3$(OCH$_3$)$_2$, —(CH$_2$)$_n$N(R$^5$)—(CH$_2$)$_o$—O—C(O)—C$_6$H$_3$(OCH$_3$)$_2$,
—N(R$^5$)—C(O)-morpholin,
—N(R$^5$)—C(O)—N(R$^5$)-phenyl, substituted by alkoxy,
—S(O)$_2$-morpholin, or is phenyl, which is unsubstituted or substituted by —(CR$^5$R$^6$)$_n$— five to seven membered aromatic or non aromatic heterocycle, and wherein the heterocycle is unsubststituted or substituted by hydroxy, —N(R$^5$)(R$^6$), lower alkoxy or lower alkyl, or by —(CH$_2$)$_n$N(R$^5$)(CH$_2$)$_o$— five or six membered aromatic or non aromatic heterocycle and wherein the heterocycle is unsubstituted or substituted by hydroxy, —N(R$^5$)(R$^6$) or lower alkyl, or is b) —(CH$_2$)$_n$— five or six membered aromatic or non aromatic heterocycle, with the exception of the the piperazinyl group in case if n=0, which rings are unsubstituted or substituted by one or two substituents, selected from the group consisting of 2-oxo-pyrrolidin, piperidinyl, phenyl, —(CH$_2$)$_n$OH, halogen, CF$_3$, =O, lower alkyl, cycloalkyl, —(CH$_2$)$_n$—O-lower alkyl, —(CH$_2$)$_n$NH$_2$, —(CH$_2$)$_n$CN, —C(O)O-lower alkyl, —CH$_2$—O—S(O)$_2$CH$_3$, —C(O)-lower alkyl, —C(O)—(CH$_2$)$_n$-lower alkoxy, —CH$_2$—N(R$^6$)C$_6$H$_4$F, —CH$_2$—N(R$^6$)C(O)O-lower alkyl, —N(R$^6$)—C(O)—N(R$^5$)—(CH$_2$)$_n$, —O-lower alkyl, -or by tetrahydrofuran, substituted by 4-Cl-phenyl, or by piperazin-1-yl, morpholinyl, thiomorpholinyl, thiomorpholin-1-oxo, pyrrolidin-1-yl or by piperidin-1-yl or is benzopiperidin-1-yl or benzothien-2-yl, or is c) —(CH$_2$)$_{n+1}$-phenyl,
—N(R$^5$)(CH$_2$)$_n$-phenyl, unsubstituted or substituted by lower alkoxy,
—O(CH$_2$)$_n$-phenyl, or
—N(R$^5$)C(O)-phenyl, or is d) —N(R$^5$)(CH$_2$)$_n$— 5-or 6 membered aromatic or non aromatic heterocycle, unsubstituted or substituted by lower alkyl, —(CH$_2$)$_n$— 5-or 6 membered aromatic or non aromatic heterocycle or is e) —(CH$_2$)$_n$—N(R$^5$)(R$^6$), lower alkyl, —O—(CH$_2$)$_n$-lower alkoxy, —(CH$_2$)$_n$-lower alkoxy, lower alkoxy, cycloalkyl, —N(R$^5$)(CH$_2$)$_n$O-lower alkyl, —N(R$^5$)(CH$_2$)$_n$OH, —N(R$^5$)(CH$_2$)$_n$N(R$^5$)(R$^6$), —C(O)O-lower alkyl, —(CH$_2$)$_n$OH, —(HC=CH)$_n$C(O)O-lower alkyl, octahydro-quinoline, 3,4-dihydro-1H-isoquinoline, 2,3-benzo-1,4-dioxa-8-aza-spiro[4,5]decane or 1,4-dioxa-8-aza-spiro[4,5]decane;

X is O, S or two hydrogen atoms;

R$^5$, R$^6$ are independently from each other hydrogen or lower alkyl,

R$^7$ is lower alkyl, lower alkoxy, —C(O)-lower alkyl, —C(O)O-benzyl, —C(O)O-lower alkyl, —(CH$_2$)$_n$NR$^5$R$^6$, pyridinyl, unsubstituted or substituted by lower alkyl, or is —CH$_2$N(R$^5$)—C(O)O-lower alkyl, —NH—C(phenyl)$_3$, pyrrolidinyl, piperidinyl, morpholinyl, piperazinyl, optionally substituted by lower alkyl;

n is 0, 1, 2, 3 or 4;
m is 0 or 1;
is 0, 1, 2, 3 or 4;

and pharmaceutically acceptable salts thereof for the manufacture of medicaments for the treatment of diseases related to the adenosine receptor.

Some minor subgroups of compounds of the present formula I are known compounds and have been described, for example in EP 427 963, U.S. Pat. No. 5,099,021, EP 295 656 or DE 19 531 49. These compounds possess microbicide activity or may be used for lowering the blood glucose level. Furthermore, WO 00/18767 describes 2-piperazino alkylamino benzoazole, having an affinity to the dopamine subtype specific ligands and are therefore useful in the treatment of diseases, related to this receptor. The compounds of WO 00/18767 are not encompassed from the scope of the present invention.

It has surprisingly been found that the compounds of formula I are adenosine receptor ligands.

Objects of the present invention are the use of compounds of formula I or their pharmaceutically acceptable salts for the manufacture of medicaments for the treatment of diseases, related to the adenosine A2 receptor, novel compounds of formula I-A per se, their manufacture, medicaments based on a compound in accordance with the invention and their production as well as the use of compounds of formula I in the control or prevention of illnesses based on the modulation of the adenosine system, such as Alzheimer's disease, Parkinson's disease, neuroprotection, schizophrenia, anxiety, pain, respiration deficits, depression, asthma, allergic responses, hypoxia, ischaemia, seizure and substance abuse. Furthermore, compounds of the present invention may be useful as sedatives, muscle relaxants, antipsychotics, antiepileptics, anticonvulsants and cardiaprotective agents. The most preferred indications in accordance with the present invention are those, which base on the $A_{2A}$ receptor antagonistic activity and which include disorders of the central nervous system, for example the treatment or prevention of certain depressive disorders, neuroprotection and Parkinson's disease as well as ADHD and diabetes mellitus.

The present invention includes novel compounds of the formula

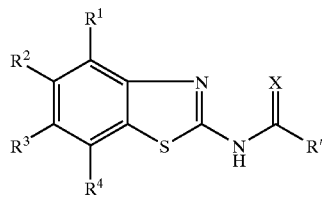

I-A wherein $R^1$ is hydrogen, lower alkyl, lower alkoxy, benzyloxy, cycloalkyloxy, halogen, hydroxy or trifluoromethyloxy;

$R^2$, $R^3$ are independently from each other hydrogen, halogen, lower alkyl or lower alkyloxy;

$R^4$ is hydrogen, lower alkyl, lower alkenyl, halogen, —C(O)-lower alkyl, —C(O)-halogen-lower alkyl, —CH(OH)-halogen-lower alkyl, —C(O)O-lower alkyl, —NHC(O)-lower alkyl, —(CH$_2$)$_n$—OH, or is phenyl, which is optionally attached to the benzo group via the linker —(O)$_m$—(CH$_2$)$_n$— and is unsubstituted or substituted by N(R$^5$)(R$^6$), halogen or nitro, or is 2,3-dihydro-1H-indolyl, azepan-1-yl, [1,4]oxazepan-4-yl, or is a five or six membered aromatic or non aromatic heterocycle, which may be attached to the benzo group via the linker —(O)$_m$—(CH$_2$)$_n$ or —N=C(CH$_3$)— and is unsubstituted or substituted by one or two group(s) R$^7$, wherein R$^7$ is defined below;

R' is (a) phenyl, optionally unsubstituted or substituted by halogen-lower alkyl, —C(O)H or by the following groups —(CH$_2$)$_n$—C(O)—N(R$^5$)—(CH$_2$)$_n$lower alkoxy, —(CH$_2$)$_n$O-halogen-lower alkyl, —(CH$_2$)$_n$O—(CH$_2$)$_{n+1}$O-lower alkyl, —S(O)$_2$—N(R$^5$)—(CH$_2$)$_n$O-lower alkyl, —(CH$_2$)$_n$OR$^5$, —(CH$_2$)$_n$N(R$^5$)—(CH$_2$)$_o$-lower alkoxy, —(CH$_2$)$_n$N[(CH$_2$)$_o$-lower alkoxy]$_2$, —(CH$_2$)$_n$N[S(O)$_2$CH$_3$]$_2$, —(CH$_2$)$_n$N[R$^5$][S(O)$_2$CH$_3$], —(CH$_2$)$_n$N(R$^5$)-lower alkenyl, —(CH$_2$)$_n$N(R$^5$)—(CH$_2$)$_o$-cycloalkyl, —(CH$_2$)$_n$N(R$^5$)—C(O)O-lower alkyl, —(CH$_2$)$_n$—S—(CH$_2$)$_n$—N(R$^5$)(R$^6$), —(CH$_2$)$_n$N(R$^5$)—(CH$_2$)$_o$—S-lower alkyl, —(CH$_2$)$_n$N(R$^5$)—S(O)$_2$CH$_3$ —(CH$_2$)$_n$N(R$^5$)—(CH$_2$)$_o$-phenyl, —(CH$_2$)$_n$N(R$^5$)—(CH$_2$)$_o$OH, —(CH$_2$)$_n$N(R$^5$)—(CH$_2$)$_o$CH(OH)—CF$_3$, —(CH$_2$)$_n$N(R$^5$)—(CH$_2$)$_o$—CF$_3$, —(CH$_2$)$_n$N(R$^5$)—(CH$_2$)$_o$—O—CH(OH)—C$_6$H$_3$(OCH$_3$)$_2$, —(CH$_2$)$_n$N(R$^5$)—(CH$_2$)$_o$—O—C(O)—C$_6$H$_3$(OCH$_3$)$_2$, —N(R$^5$)—C(O)-morpholin, —N(R$^5$)—C(O)—N(R$^5$)-phenyl, substituted by alkoxy, —S(O)$_2$-morpholin, or is phenyl, which is unsubstituted or substituted by —(CR$^5$R$^6$)$_n$— five to seven membered aromatic or non aromatic heterocycle, and wherein the heterocycle is unsubstituted or substituted by hydroxy, —N(R$^5$)(R$^6$) or lower alkyl, or by —(CH$_2$)$_n$N(R$^5$)(CH$_2$)$_o$— five or six membered aromatic or non aromatic heterocycle and wherein the heterocycle is unsubstituted or substituted by hydroxy, —N(R$^5$)(R$^6$) or lower alkyl, or is —N(R$^5$)-phenyl, which is unsubstituted or substituted by lower alkoxy, or is b) —(CH$_2$)$_n$— five or six membered aromatic or non aromatic heterocycle, with the exception of the the piperazinyl group in case if n=0, which rings may be optionally substituted by 2-oxo-pyrrolidin, piperidinyl, phenyl, —(CH$_2$)$_n$OH, halogen, CF$_3$, =O, lower alkyl, cycloalkyl, —(CH$_2$)$_n$—O-lower alkyl, —(CH$_2$)$_n$NH$_2$, —(CH$_2$)$_n$CN, —C(O)O-lower alkyl, —CH$_2$—O—S(O)$_2$CH$_3$, —C(O)-lower alkyl, —C(O)—(CH$_2$)$_n$-lower alkoxy, —CH$_2$—N(R$^6$)C$_6$H$_4$F, —CH$_2$—N(R$^6$)C(O)O-lower alkyl, —N(R$^6$)—C(O)—N(R$^5$)—(CH$_2$)$_n$—O-lower alkyl, -or by tetrahydrofuran, substituted by 4-Cl-phenyl, or by piperazin-1-yl, morpholinyl, thiomorpholinyl, thiomorpholin-1-oxo, pyrrolidin-1-yl or by piperidin-1-yl or is benzopiperidin-1-yl or benzothien-2-yl, or is c) —N(R$^5$)(CH$_2$)$_{n+1}$-phenyl, unsubstituted or substituted by lower alkoxy, —O(CH$_2$)$_n$-phenyl, or —N(R$^5$)C(O)-phenyl, or is d) —N(R$^5$)(CH$_2$)$_n$— 5-or 6 membered aromatic or non aromatic heterocycle, unsubstituted or substituted by lower alkyl, —(CH$_2$)$_n$— 5-or 6 membered aromatic or nonaromatic heterocycle or is e) —O—(CH$_2$)$_n$-lower alkoxy, lower alkyl-lower alkoxy, —N(R$^5$)(CH$_2$)$_n$N(R$^5$)(R$^6$), —(CH$_2$)$_n$OH, —(HC=CH)$_n$C(O)O-lower alkyl, octahydroquinoline, 3,4-dihydro-1H-isoquinoline, 2,3-benzo-1,4-dioxa-8-aza-spiro[4,5]decane or 1,4-dioxa-8-aza-spiro[4,5]decane.

X is O, S or two hydrogen atoms;

R$^5$, R$^6$ are independently from each other hydrogen or lower alkyl,

R$^7$ is lower alkyl, lower alkoxy, —C(O)-lower alkyl, —C(O)O-benzyl, —C(O)O-lower alkyl, —CH$_2$)$_n$NR$^5$R$^6$, pyridinyl, unsubstituted or substituted by lower alkyl, or is —CH$_2$N(R$^5$)—C(O)O-lower alkyl, —NH—C(phenyl)$_3$, pyrrolidinyl, piperidinyl, morpholinyl, piperazinyl, unsubstituted or substituted by lower alkyl;

n is 0, 1, 2, 3 or 4;

m is 0 or 1;

is 0, 1, 2, 3 or 4;

or pharmaceutically acceptable salts thereof.

DETAILED DESCRIPTION

As used herein, the term "lower alkyl" denotes a saturated straight- or branched-chain alkyl group containing from 1 to 6 carbon atoms, for example, methyl, ethyl, propyl, isopropyl, n-butyl, i-butyl, 2-butyl, t-butyl and the like. Preferred lower alkyl groups are groups with 1–4 carbon atoms.

As used herein, the term "lower alkenyl" denotes a unsaturated straight- or branched-chain alkyl group containing from 2 to 6 carbon atoms, for example, ethylen, propylen, isopropylen, n-butylen, i-butylen, 2-butylen, t-butylen and the like. Preferred lower alkyl groups are groups with 2–4 carbon atoms.

The term "cycloalkyl" denotes a saturated carbocyclic group, containing 3–6 carbon atoms.

The term "halogen" denotes chlorine, iodine, fluorine and bromine.

The term "lower alkoxy" denotes a group wherein the alkyl residues are as defined above, and which is attached via an oxygen atom.

The term "five or six membered aromatic or non aromatic heterocycle" denotes the following group: aromatic heterocyclic groups are, for example pyrrol-1-yl, tetrazolyl, imidazol-1 or 2-yl, pyrazoll-yl, pyridin-1, 2, 3 or 4-yl, pyrazinyl, pyrimidinyl, pyridazinyl, isothiazolyl, isoxazolyl, thiazolyl, thienyl or furyl; Non aromatic heterocyclic groups are, for example, pyrrolidinyl, imidazolidinyl, pyrazolidinyl, piperidinyl, piperazinyl, morpholinyl, thiomorpholinyl, thiomorpholin-1,1-dioxo or thiomorpholin-1-oxo.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

Preferred compounds of formula I are those, wherein R$^1$ is methoxy, X is oxygen and R$^2$/R$^3$ are hydrogen.

Exemplary preferred are compounds of formula I for the above mentioned method of treatment, wherein R is an unsubstituted or substituted five or six membered aromatic heterocycle, for example the following compounds:

N-(4-methoxy-7-morpholin-4-yl-benzothiazol-2-yl)-2-methyl-isonicotinamide, 5-methyl-thiophene-2-carboxylic acid (4-methoxy-7-phenyl-benzothiazol-2-yl)-amide, 5-methyl-furan-2-carboxylic acid (4-methoxy-7-phenyl-benzothiazol-2-yl)-amide, N-(4-methoxy-7-phenyl-benzothiazol-2-yl)-isonicotinamide, 5-methyl-thiophene-2-carboxylic acid (4-methoxy-7-pyridin-4-yl-benzothiazol-2-yl)-amide, 5-methyl-thiophene-2-carboxylic acid (4-methoxy-7-pyridin-3-yl-benzothiazol-2-yl)-amide, 5-methyl-thiophene-2-carboxylic acid [4-methoxy-7-(2-methyl-pyridin-4-yl)-benzothiazol-2-yl]-amide, 5-methyl-thiophene-2-carboxylic acid [7-(3-amino-phenyl)-4-methoxy-benzothiazol-2-yl]-amide, N-(4-methoxy-7-thiophen-2-yl-benzothiazol-2-yl)-2-methyl-isonicotinamide, N-[4-methoxy-7-(2-pyridin-2-yl-thiazol-4-yl)-benzothiazol-2-yl]-2-methyl-isonicotinamide, N-[4-methoxy-7-(2-pyrrolidin-1-yl-thiazol-4-yl)-benzothiazol-2-yl]-2-methyl-isonicotinamide, N-{4-methoxy-7-[2-(4-methyl-piperazin-1-yl)-thiazol-4-yl]-benzothiazol-2-yl}-2-methyl-isonicotinamide and N-[4-methoxy-7-(5-methyl-thiophen-2-yl)-benzothiazol-2-yl]-2-methyl-isonicotinamide.

Further preferred compounds of formula I for the above mentioned method of treatment are compounds, wherein R is an unsubstituted or substituted five or six membered non aromatic heterocycle, for example the following compounds:

morpholine-4-carboxylic acid (4-methoxy-7-phenyl-benzothiazol-2-yl)-amide, thiomorpholine-4-carboxylic acid (4-methoxy-7-phenyl-benzothiazol-2-yl)-amide, 1-oxo-1l 4-thiomorpholine-4-carboxylic acid (4-methoxy-7-phenyl-benzothiazol-2-yl)-amide, morpholine-4-carboxylic acid {4-methoxy-7-[2-(6-methyl-pyridin-3-yl)-thiazol-4-yl]-benzothiazol-2-yl}-amide, morpholine-4-carboxylic acid [4-methoxy-7-(2-pyridin-2-yl-thiazol-4-yl)-benzothiazol-2-yl]-amide, morpholine-4-carboxylic acid {4-methoxy-7-[2-(4-methyl-piperazin-1-yl)-thiazol-4-yl]-benzothiazol-2-yl}-amide, morpholine-4-carboxylic acid [4-methoxy-7-(2-piperidin-1-yl-thiazol-4-yl)-benzothiazol-2-yl]-amide, morpholine-4-carboxylic acid [4-methoxy-7-(5-methyl-thiophen-2-yl)-benzothiazol-2-yl]-amide, 4-(4-methoxy-7-morpholin-4-yl-benzothiazol-2-ylcarbamoyl)-piperidine-1-carboxylic acid tert-butyl ester, 1-acetyl-piperidine-4-carboxylic acid (4-methoxy-7-morpholin-4-yl-benzothiazol-2-yl)-amide, 4-oxo-piperidine-1-carboxylic acid (4-methoxy-7-morpholin-4-yl-benzothiazol-2-yl)-amide and 1-oxo-1$\lambda^4$-thiomorpholine-4-carboxylic acid (4-methoxy-7-piperidin-1-yl-benzothiazol-2-yl)-amide.

Preferred are further compounds, wherein R is methoxy, for example the following compounds:

rac-[7-(2-bromo-1-hydroxy-ethyl)-4-methoxy-benzothiazol-2-yl]-carbamic acid methyl ester, {4-methoxy-7-[2-(6-methyl-pyridin-3-yl)-thiazol-4-yl]-benzothiazol-2-yl}-carbamic acid methyl ester,

[4-methoxy-7-(2-pyridin-2-yl-thiazol-4-yl)-benzothiazol-2-yl]-carbamic acid methyl ester,

[4-methoxy-7-(2-piperidin-1-yl-thiazol-4-yl)-benzothiazol-2-yl]-carbamic acid methyl ester and {4-methoxy-7-[2-(4-methyl-piperazin-1-yl)-thiazol-4-yl]-benzothiazol-2-yl}-carbamic acid methyl ester.

Preferred compounds of formula I for the above mentioned method of treatment are those, wherein R is phenyl, optionally substituted by halogen, $CF_3$, —$CH_2OH$, —$CH_2NHCH_2CH_2OCH_3$, —$CH_2NHCH_2CH_2OH$, —$CH_2NHCH_2$-pyridinyl, —$CH_2NH_2$, —$CH_2NHCH_2CH_2SCH_3$, —$CH_2N(CH_3)CH_2CH_2SCH_3$, —$CH_2N(CH_3)CH_2CH_2OCH_3$, —$CH_2N(CH_2\ CH_3)CH_2CH_2OCH_3$, —$CH_2NHCH_3$, —$CH_2SCH_2CH_2N(CH_3)_2$, —$CH_2OCH_3$, —$CH_2OCH_2CH_2OCH_3$ or —$CH_2N(CH_3)C(O)OCH_3$, for example the following compounds:

4-hydroxymethyl-N-(4-methoxy-7-phenyl-benzothiazol-2-yl)-benzamide, 4-fluoro-N-(4-methoxy-7-phenyl-benzothiazol-2-yl)-benzamide, 2-(4-fluoro-benzoylamino)-4-methoxy-benzothiazole-7-carboxylic acid methyl ester, 4-[(2-methoxy-ethylamino)-methyl]-N-(4-methoxy-7-phenyl-benzothiazol-2-yl)-benzamide, 4-[(2-hydroxy-ethylamino)-methyl]-N-(4-methoxy-7-phenyl-benzothiazol-2-yl)-benzamide, N-(4-methoxy-7-phenyl-benzothiazol-2-yl)-4-{[(pyridin-4-yl-methyl)-amino]-methyl}-benzamide, N-(4-methoxy-7-phenyl-benzothiazol-2-yl)-4-{[(pyridin-3-yl-methyl)-amino]-methyl}-benzamide, 4-aminomethyl-N-(4-methoxy-7-phenyl-benzothiazol-2-yl)-benzamide, N-(4-methoxy-7-phenyl-benzothiazol-2-yl)-4-[(2-methylsulfanyl-ethylamino)-methyl]-benzamide, 4-{[(2-methoxy-ethyl)-methyl-amino]-methyl}-N-(4-methoxy-7-morpholin-4-yl-benzothiazol-2-yl)-benzamide, N-[7-(2-amino-thiazol-4-yl)-4-methoxy-benzothiazol-2-yl]-4-fluoro-benzamide, 4-fluoro-N-{4-methoxy-7-[2-(6-methyl-pyridin-3-yl)-thiazol-4-yl]-benzothiazol-2-yl}-benzamide, 4-fluoro-N-(4-methoxy-7-thiophen-2-yl-benzothiazol-2-yl)-benzamide, 4-fluoro-N-{4-methoxy-7-[2-(4-methyl-piperazin-1-yl)-thiazol-4-yl]-benzothiazol-2-yl}-benzamide, 4-{[(2-methoxy-ethyl)-methyl-amino]-methyl}-N-{4-methoxy-7-[2-(6-methyl-pyridin-3-yl)-thiazol-4-yl]-benzothiazol-2-yl}-benzamide, 4-{[(2-Methoxy-ethyl)-methyl-amino]-methyl}-N-(4-methoxy-7-thiophen-2-yl-benzothiazol-2-yl)-benzamide, 4-{[(2-methoxy-ethyl)-methyl-amino]-methyl}-N-[4-methoxy-7-(2-pyridin-2-yl-thiazol-4-yl)-benzothiazol-2-yl]-benzamide, N-(4-methoxy-7-morpholin-4-yl-benzothiazol-2-yl)-4-trifluoromethyl-benzamide, 4-fluoro-N-(4-methoxy-7-morpholin-4-yl-benzothiazol-2-yl)-benzamide, N-(4-methoxy-7-morpholin-4-yl-benzothiazol-2-yl)-benzamide, 4-chloro-3-{[ethyl-(2-methoxy-ethyl)-amino]-methyl}-N-(4-methoxy-7-morpholin-4-yl-benzothiazol-2-yl)-benzamide, N-(4-methoxy-7-morpholin-4-yl-benzothiazol-2-yl)-3-methylaminomethyl-benzamide, 4-chloro-N-(4-methoxy-7-morpholin-4-yl-benzothiazol-2-yl)-3-methylaminomethyl-benzamide, 4-chloro-3-{[(2-methoxy-ethyl)-methyl-amino]-methyl}-N-(4-methoxy-7-morpholin-4-yl-benzothiazol-2-yl)-benzamide, 4-chloro-3-[(2-methoxy-ethylamino)-methyl]-N-(4-methoxy-7-morpholin-4-yl-benzothiazol-2-yl)-benzamide, 3-[(2-methoxy-ethylamino)-methyl]-N-(4-methoxy-7-morpholin-4-yl-benzothiazol-2-yl)-benzamide, 3-{[(2-methoxy-ethyl)-methyl-amino]-methyl}-N-(4-methoxy-7-morpholin-4-yl-benzothiazol-2-yl)-benzamide, 4-[(2-ethoxy-ethylamino)-methyl]-N-(4-methoxy-7-morpholin-4-yl-benzothiazol-2-yl)-benzamide, N-(4-methoxy-7-morpholin-4-yl-benzothiazol-2-yl)-4-methylaminomethyl-benzamide, 4-(2-dimethylamino-ethylsulfanylmethyl)-N-(4-methoxy-7-morpholin-4-yl-benzothiazol-2-yl)-benzamide, 4-{[(2-ethoxy-ethyl)-ethyl-amino]-methyl}-N-(4-methoxy-7-morpholin-4-yl-benzothiazol-2-yl)-benzamide, 4-{[(2-ethoxy-ethyl)-methyl-amino]-methyl}-N-(4-methoxy-7-morpholin-4-yl-benzothiazol-2-yl)-benzamide, 4-(2-methoxy-ethoxymethyl)-N-(4-methoxy-7-morpholin-4-yl-benzothiazol-2-yl)-benzamide, 4-methoxymethyl-N-(4-methoxy-7-morpholin-4-yl-benzothiazol-2-yl)-benzamide, N-(4-methoxy-7-thiomorpholin-4-yl-benzothiazol-2-yl)-benzamide and

[4-(4-methoxy-7-morpholin-4-yl-benzothiazol-2-ylcarbamoyl)-benzyl]-methyl-carbamic acid methyl ester.

Further preferred compounds of formula I for the above mentioned method of treatment are those, wherein R is phenyl, substituted by an unsubstituted or substituted —$(CH_2)_n$— five to seven membered aromatic or non aromatic heterocycle, for example the following compounds:

4-imidazol-1-yl-methyl-N-(4-methoxy-7-phenyl-benzothiazol-2-yl)-benzamide, 4-(4-Hydroxy-piperidin-1-yl-methyl)-N-(4-methoxy-7-phenyl-benzothiazol-2-yl)-benzamide, 4-[1,4]diazepan-1-yl-methyl-N-(4-methoxy-7-phenyl-benzothiazol-2-yl)-benzamide, 4-(3(S)-dimethylamino-pyrrolidin-1-yl-methyl)-N-(4-methoxy-7-phenyl-benzothiazol-2-yl)-benzamide, N-{4-methoxy-7-[2-(6-methyl-pyridin-3-yl)-thiazol-4-yl]-benzothiazol-2-yl}-4-pyrrolidin-1-yl-methyl-benzamide, N-(4-methoxy-7-thiophen-2-yl-benzothiazol-2-yl)-4-pyrrolidin-1-yl-methyl-benzamide, N-[4-methoxy-7-(2-pyridin-2-yl-thiazol-4-yl)-benzothiazol-2-yl]-4-pyrrolidin-1-yl-methyl-benzamide, 4-chloro-N-(4-methoxy-7-morpholin-4-yl-benzothiazol-2-yl)-3-pyrrolidin-1-yl-methyl-benzamide, N-(4-methoxy-7-morpholin-4-yl-benzothiazol-2-yl)-3-pyrrolidin-1-yl-methyl-benzamide, N-(4-methoxy-7-morpholin-4-yl-benzothiazol-2-yl)-4-(2-methyl-imidazol-1-yl-methyl)-benzamide and N-(4-methoxy-7-morpholin-4-yl-benzothiazol-2-yl)-4-(4-methyl-piperazin-1-yl-methyl)-benzamide.

Especially preferred are compounds, wherein $R^4$ is an unsubstituted or substituted five to seven membered aromatic or non aromatic heterocycle, which is for example, but not limited to, morpholine or piperazine.

Preferred compounds of formula IA are those, wherein $R^1$ is methoxy, X is oxygen and $R^2/R^3$ are hydrogen.

Exemplary preferred are compounds of formula IA, wherein R' is an unsubstituted or substituted five or six membered aromatic heterocycle, for example the following compounds:

N-(4-methoxy-7-morpholin-4-yl-benzothiazol-2-yl)-2-methyl-isonicotinamide, 5-methyl-thiophene-2-carboxylic acid (4-methoxy-7-phenyl-benzothiazol-2-yl)-amide, 5-methyl-furan-2-carboxylic acid (4-methoxy-7-phenyl-benzothiazol-2-yl)-amide, N-(4-methoxy-7-phenyl-benzothiazol-2-yl)-isonicotinamide, 5-methyl-thiophene-2-carboxylic acid (4-methoxy-7-pyridin-4-yl-benzothiazol-2-yl)-amide, 5-methyl-thiophene-2-carboxylic acid (4-methoxy-7-pyridin-3-yl-benzothiazol-2-yl)-amide, 5-methyl-thiophene-2-carboxylic acid [4-methoxy-7-(2-methyl-pyridin-4-yl)-benzothiazol-2-yl]-amide, 5-methyl-thiophene-2-carboxylic acid [7-(3-amino-phenyl)-4-methoxy-benzothiazol-2-yl]-amide, N-(4-methoxy-7-thiophen-2-yl-benzothiazol-2-yl)-2-methyl-isonicotinamide, N-[4-methoxy-7-(2-pyridin-2-yl-thiazol-4-yl)-benzothiazol-2-yl]-2-methyl-isonicotinamide, N-[4-methoxy-7-(2-pyrrolidin-1-yl-thiazol-4-yl)-benzothiazol-2-yl]-2-methyl-isonicotinamide, N-{4-methoxy-7-[2-(4-methyl-piperazin-1-yl)-thiazol-4-yl]-benzothiazol-2-yl}-2-methyl-isonicotinamide and N-[4-methoxy-7-(5-methyl-thiophen-2-yl)-benzothiazol-2-yl]-2-methyl-isonicotinamide.

Further preferred compounds of formula IA are compounds, wherein R is an unsubstituted or substituted five or six membered non aromatic heterocycle, for example the following compounds:

morpholine-4-carboxylic acid (4-methoxy-7-phenyl-benzothiazol-2-yl)-amide, thiomorpholine-4-carboxylic acid (4-methoxy-7-phenyl-benzothiazol-2-yl)-amide, 1-oxo-11 4-thiomorpholine-4-carboxylic acid (4-methoxy-7-phenyl-benzothiazol-2-yl)-amide, morpholine-4-carboxylic acid {4-methoxy-7-[2-(6-methyl-pyridin-3-yl)-thiazol-4-yl]-benzothiazol-2-yl}-amide, morpholine-4-carboxylic acid [4-methoxy-7-(2-pyridin-2-yl-thiazol-4-yl)-benzothiazol-2-yl]-amide, morpholine-4-carboxylic acid {4-methoxy-7-[2-(4-methyl-piperazin-1-yl)-thiazol-4-yl]-benzothiazol-2-yl}-amide, morpholine-4-carboxylic acid [4-methoxy-7-(2-piperidin-1-yl-thiazol-4-yl)-benzothiazol-2-yl]-amide, morpholine-4-carboxylic acid [4-methoxy-7-(5-methyl-thiophen-2-yl)-benzothiazol-2-yl]-amide, 4-(4-methoxy-7-morpholin-4-yl-benzothiazol-2-yl-carbamoyl)-piperidine-1-carboxylic acid tert-butyl ester, 1-acetyl-piperidine-4-carboxylic acid (4-methoxy-7-morpholin-4-yl-benzothiazol-2-yl)-amide, 4-oxo-piperidine-1-carboxylic acid (4-methoxy-7-morpholin-4-yl-benzothiazol-2-yl)-amide and 1-oxo-1$\lambda^4$-thiomorpholine-4-carboxylic acid (4-methoxy-7-piperidin-1-yl-benzothiazol-2-yl)-amide.

Preferred are further compounds, wherein R is methoxy, for example the following compounds:

rac-[7-(2-bromo-1-hydroxy-ethyl)-4-methoxy-benzothiazol-2-yl]-carbamic acid methyl ester, {4-methoxy-7-[2-(6-methyl-pyridin-3-yl)-thiazol-4-yl]-benzothiazol-2-yl}-carbamic acid methyl ester,

[4-methoxy-7-(2-pyridin-2-yl-thiazol-4-yl)-benzothiazol-2-yl]-carbamic acid methyl ester,

[4-methoxy-7-(2-piperidin-1-yl-thiazol-4-yl)-benzothiazol-2-yl]-carbamic acid methyl ester and {4-methoxy-7-[2-(4-methyl-piperazin-1-yl)-thiazol-4-yl]-benzothiazol-2-yl}-carbamic acid methyl ester.

Preferred compounds of formula IA are those, wherein R' is phenyl, unsubstituted or substituted by —$CH_2OH$, —$CH_2NHCH_2CH_2OCH_3$, —$CH_2NHCH_2CH_2OH$, —$CH_2NHCH_2$-pyridinyl, —$CH_2NH_2$, —$CH_2NHCH_2CH_2SCH_3$, —$CH_2N(CH_3)CH_2CH_2SCH_3$, —$CH_2N(CH_3)CH_2CH_2OCH_3$, —$CH_2N(CH_2CH_3)CH_2CH_2OCH_3$, —$CH_2NHCH_3$, —$CH_2SCH_2CH_2N(CH_3)_2$, —$CH_2OCH_3$, —$CH_2OCH_2CH_2OCH_3$ or —$CH_2N(CH_3)C(O)OCH_3$, for example the following compounds:

4-hydroxymethyl-N-(4-methoxy-7-phenyl-benzothiazol-2-yl)-benzamide,

4-[(2-methoxy-ethylamino)-methyl]-N-(4-methoxy-7-phenyl-benzothiazol-2-yl)-benzamide, 4-[(2-hydroxy-ethylamino)-methyl]-N-(4-methoxy-7-phenyl-benzothiazol-2-yl)-benzamide, N-(4-methoxy-7-phenyl-benzothiazol-2-yl)-4-{[(pyridin-4-ylmethyl)-amino]-methyl}-benzamide, N-(4-methoxy-7-phenyl-benzothiazol-2-yl)-4-{[(pyridin-3-ylmethyl)-amino]-methyl}-benzamide, 4-aminomethyl-N-(4-methoxy-7-phenyl-benzothiazol-2-yl)-benzamide, N-(4-methoxy-7-phenyl-benzothiazol-2-yl)-4-[(2-methylsulfanyl-ethylamino)-methyl]-benzamide, 4-{[(2-methoxy-ethyl)-methyl-amino]-methyl}-N-(4-methoxy-7-morpholin-4-yl-benzothiazol-2-yl)-benzamide, N-[7-(2-amino-thiazol-4-yl)-4-methoxy-benzothiazol-2-yl]-4-fluoro-benzamide, 4-fluoro-N-{4-methoxy-7-[2-(6-methyl-pyridin-3-yl)-thiazol-4-yl]-benzothiazol-2-yl}-benzamide, 4-{[(2-methoxy-ethyl)-methyl-amino]-methyl}-N-{4-methoxy-7-[2-(6-methyl-pyridin-3-yl)-thiazol-4-yl]-benzothiazol-2-yl}-benzamide, 4-{[(2-Methoxy-ethyl)-methyl-amino]-methyl}-N-(4-methoxy-7-thiophen-2-yl-benzothiazol-2-yl)-benzamide, 4-{[(2-methoxy-ethyl)-methyl-amino]-methyl}-N-[4-methoxy-7-(2-pyridin-2-yl-thiazol-4-yl)-benzothiazol-2-yl]-benzamide, N-(4-methoxy-7-morpholin-4-yl-benzothiazol-2-yl)-4-trifluoromethyl-benzamide, N-(4-methoxy-7-morpholin-4-yl-benzothiazol-2-yl)-benzamide, 4-chloro-3-{[ethyl-(2-methoxy-ethyl)-amino]-methyl}-N-(4-methoxy-7-morpholin-4-yl-benzothiazol-2-yl)-benzamide, N-(4-methoxy-7-morpholin-4-yl-benzothiazol-2-yl)-3-methylaminomethyl-benzamide,
4-chloro-N-(4-methoxy-7-morpholin-4-yl-benzothiazol-2-yl)-3-methylaminomethyl-benzamide,
4-chloro-3-{[(2-methoxy-ethyl)-methyl-amino]-methyl}-N-(4-methoxy-7-morpholin-4-yl-benzothiazol-2-yl)-benzamide,
4-chloro-3-[(2-methoxy-ethylamino)-methyl]-N-(4-methoxy-7-morpholin-4-yl-benzothiazol-2-yl)-benzamide,
3-[(2-methoxy-ethylamino)-methyl]-N-(4-methoxy-7-morpholin-4-yl-benzothiazol-2-yl)-benzamide,
3-{[(2-methoxy-ethyl)-methyl-amino]-methyl}-N-(4-methoxy-7-morpholin-4-yl-benzothiazol-2-yl)-benzamide,
4-[(2-ethoxy-ethylamino)-methyl]-N-(4-methoxy-7-morpholin-4-yl-benzothiazol-2-yl)-benzamide,
N-(4-methoxy-7-morpholin-4-yl-benzothiazol-2-yl)-4-methylaminomethyl-benzamide,
4-(2-dimethylamino-ethylsulfanylmethyl)-N-(4-methoxy-7-morpholin-4-yl-benzothiazol-2-yl)-benzamide,
4-{[(2-ethoxy-ethyl)-ethyl-amino]-methyl}-N-(4-methoxy-7-morpholin-4-yl-benzothiazol-2-yl)-benzamide,
4-{[(2-ethoxy-ethyl)-methyl-amino]-methyl}-N-(4-methoxy-7-morpholin-4-yl-benzothiazol-2-yl)-benzamide,
4-(2-methoxy-ethoxymethyl)-N-(4-methoxy-7-morpholin-4-yl-benzothiazol-2-yl)-benzamide,
4-methoxymethyl-N-(4-methoxy-7-morpholin-4-yl-benzothiazol-2-yl)-benzamide,
N-(4-methoxy-7-thiomorpholin-4-yl-benzothiazol-2-yl)-benzamide and
[4-(4-methoxy-7-morpholin-4-yl-benzothiazol-2-yl-carbamoyl)-benzyl]-methyl-carbamic acid methyl ester.

Further preferred compounds of formula IA are those, wherein R' is phenyl, substituted by an unsubstituted or substituted —(CR$^5$R$^6$)$_n$— five to seven membered aromatic or non aromatic heterocycle, for example the following compounds:

4-imidazol-1-ylmethyl-N-(4-methoxy-7-phenyl-benzothiazol-2-yl)-benzamide,
4-(4-Hydroxy-piperidin-1-yl-methyl)-N-(4-methoxy-7-phenyl-benzothiazol-2-yl)-benzamide,
4-[1,4]diazepan-1-yl-methyl-N-(4-methoxy-7-phenyl-benzothiazol-2-yl)-benzamide,
4-(3(S)-dimethylamino-pyrrolidin-1-yl-methyl)-N-(4-methoxy-7-phenyl-benzothiazol-2-yl)-benzamide,
N-{4-methoxy-7-[2-(6-methyl-pyridin-3-yl)-thiazol-4-yl]-benzothiazol-2-yl}-4-pyrrolidin-1-yl-methyl-benzamide,
N-(4-methoxy-7-thiophen-2-yl-benzothiazol-2-yl)-4-pyrrolidin-1-yl-methyl-benzamide,
N-[4-methoxy-7-(2-pyridin-2-yl-thiazol-4-yl)-benzothiazol-2-yl]-4-pyrrolidin-1-yl-methyl-benzamide,
4-chloro-N-(4-methoxy-7-morpholin-4-yl-benzothiazol-2-yl)-3-pyrrolidin-1-yl-methyl-benzamide,
N-(4-methoxy-7-morpholin-4-yl-benzothiazol-2-yl)-3-pyrrolidin-1-yl-methyl-benzamide,
N-(4-methoxy-7-morpholin-4-yl-benzothiazol-2-yl)-4-(2-methyl-imidazol-1-yl-methyl)-benzamide and
N-(4-methoxy-7-morpholin-4-yl-benzothiazol-2-yl)-4-(4-methyl-piperazin-1-yl-methyl)-benzamide.

Especially preferred are compounds of formula IA, wherein R$^4$ is an unsubstituted or substituted five to seven membered aromatic or non aromatic heterocycle, which is for example morpholine or piperazine.

The present compounds of formulas I and I-A and their pharmaceutically acceptable salts can be prepared by methods known in the art, for example, by processes described below, which process comprises reacting a compound of formula

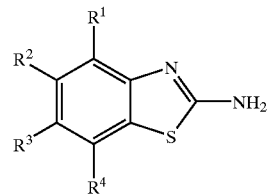

II with a compound of formula

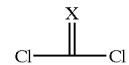

III and an amine of the formula R$^5$R$^6$NH or an appropiate cyclic amine to a compound of formula

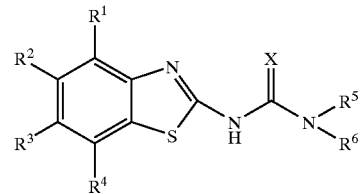

I-1 or to compounds of formula I-1, wherein the group —NR$^5$R$^6$ is replaced by a cyclic amine, wherein R$^1$–R$^6$ and X have the significances given above, or reacting a compound of formula

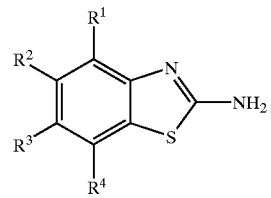

II with a compound of formula

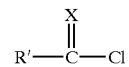

VI to a compound of formula I-A, wherein R$^1$–R$^4$, R' and X have the significances given above, or reacting a compound of formula

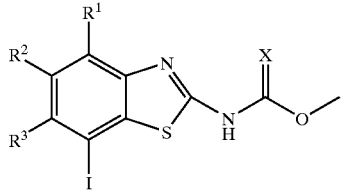

VII with a compound of formula

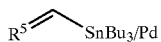

to a compound of formula

I-3

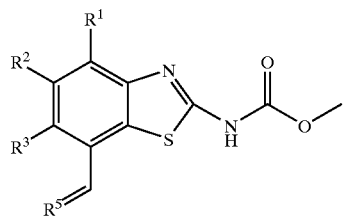

wherein $R^1$–$R^5$ have the significances given above, or hydrogenating a compound of formula I-3 with $H_2$/Pd/C to give a compound of formula

I-2

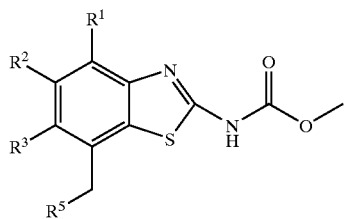

wherein $R^1$–$R^5$ have the significances given above, or reacting a compound of formula I-3 with N-bromosuccinimide/$H_2O$ to give a compound of formula

I-4

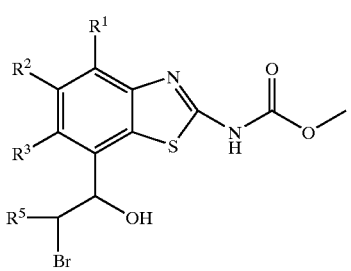

wherein $R^1$–$R^5$ have the significances given above, or oxidizing a compound of formula I-4 to a compound of formula

I-5

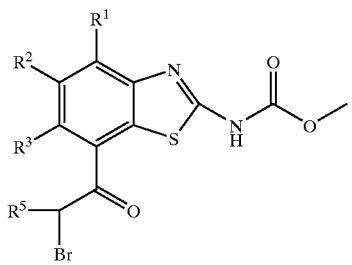

wherein $R^1$–$R^5$ have the significances given above, or reacting a compound of formula I-5 with a compound of formula

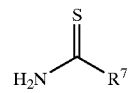

to a compound of formula

I-6

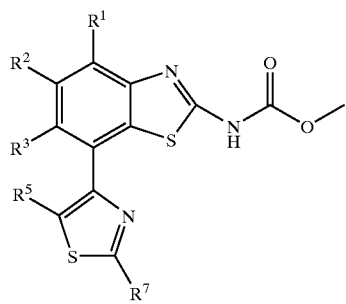

wherein $R^1$–$R^5$ and $R^7$ have the significances given above, or reacting a compound of formula I-5 with a compound of formula

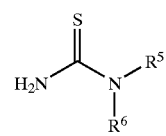

to a compound of formula

I-7

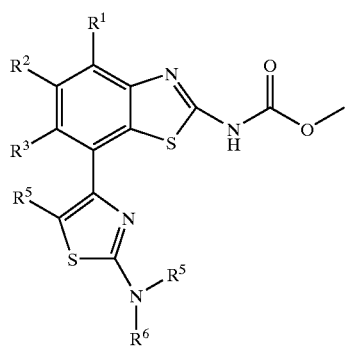

wherein $R^1$–$R^6$ have the significances given above, or reacting a compound of formula I-5 with a compound of formula

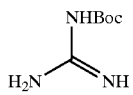

to a compound of formula

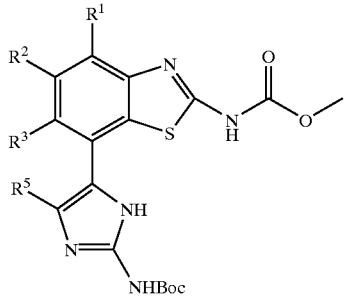

and cleaving off the boc-group to a compound of formula

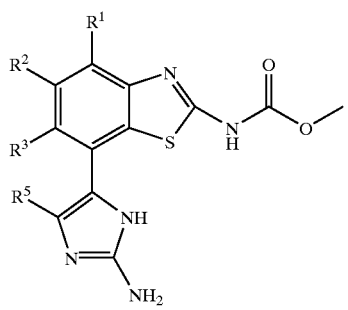

wherein $R^1$–$R^5$ have the significances given above, or modifying one or more substituents $R^1$–$R7^6$ within the definitions given above, and if desired, converting the compounds obtained into pharmaceutically acceptable acid addition salts.

All reaction steps described above are carried out in conventional manner and are described in more detail in the working examples.

In accordance with process variant a) a compound of formula II, for example 2-amino-7-phenyl-4-methoxy-benzothiazol in pyridine is dissolved in tetrahydrofuran and is then treated with phosgene in toluene. The reaction mixture is concentrated to half the volume under reduced pressure and the appropiate amine, for example an amine of formula $R^5R^6NH$ or a cyclic amine, such as morpholine or thiomorpholine, are added. The obtained product is isolated by flash chromatography.

Reaction variant b) describes the process for preparation of a compound of formula I, wherein a compound of formula II is reacting with a compound of formula IV. The reaction is carried out for about 10 minutes in conventional manner. The obtained compound is then isolated by flash chromatography.

The salt formation is effected at room temperatures in accordance with methods which are known per se and which are familiar to any person skilled in the art. Not only salts with inorganic acids, but also salts with organic acids came into consideration. Hydrochlorides, hydrobromides, sulphates, nitrates, citrate, acetates, maleates, succinates, methan-sulphonates, p-toluenesulphonates and the like are examples of such salts.

In Examples 1–187 and in the following schemes 1 and 2 the preparation of compounds of formula I is described in more detail.

The starting materials are known compounds or may be prepared according to methods known in the art.

Scheme 1

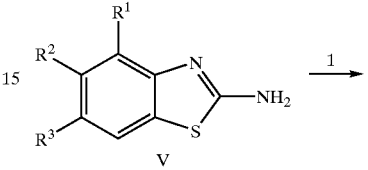

V

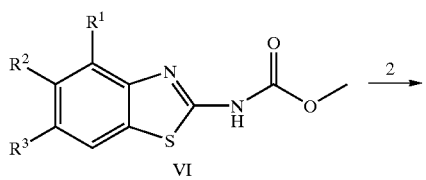

VI

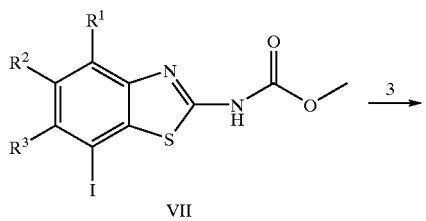

VII

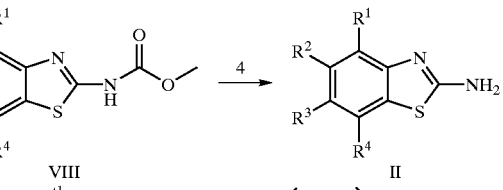

VIII
urethanes

II

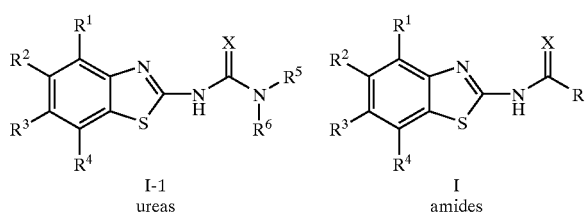

I-1
ureas

I
amides wherein the numbers 1–6 have the following meaning:
1 MeO(CO)Cl, base
2 ICl
3 $R^4$—$B(OR^5)_2$ or $R^4$—$Sn(CH_3)_3$, Pd-catalyst
4 KOH
5 $C(X)Cl_2$, $R^5R^6NH$, or $R^5NCX$
6 $RC(X)Cl$, base The definition of substituents is described above.

Scheme 2
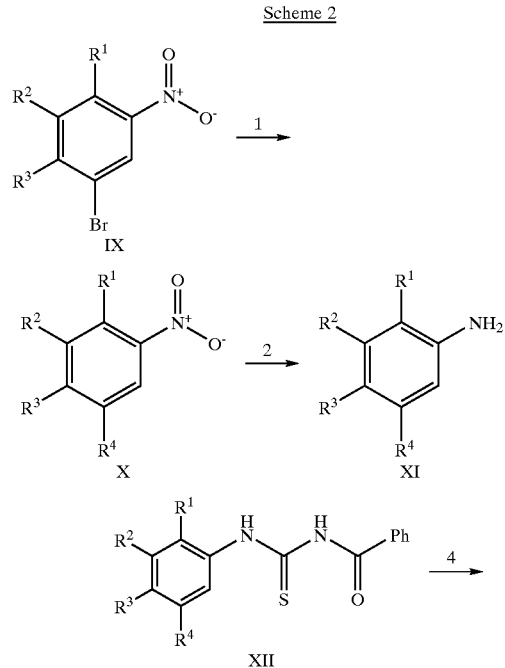
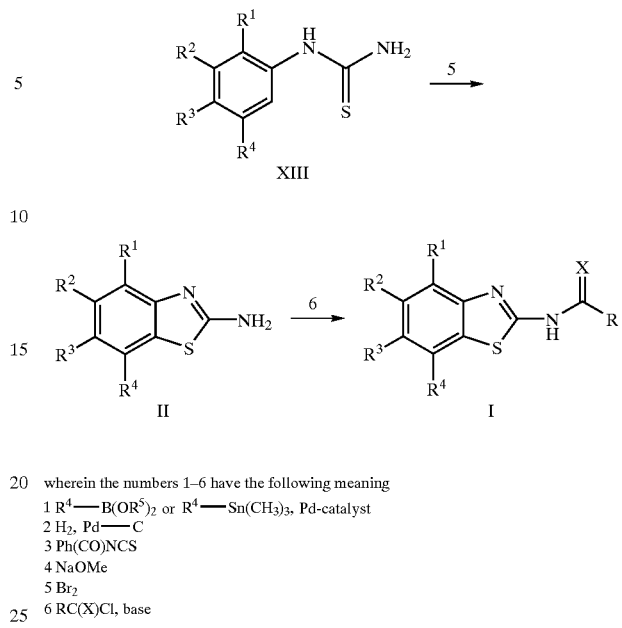
wherein the numbers 1–6 have the following meaning
1 $R^4$—$B(OR^5)_2$ or $R^4$—$Sn(CH_3)_3$, Pd-catalyst
2 $H_2$, Pd—C
3 Ph(CO)NCS
4 NaOMe
5 $Br_2$
6 RC(X)Cl, base
and the definition of the substituents $R^1$–$R^4$, $R^5$, X and R is given above.
Scheme 3

The definitions of $R^1$ to $R^5$ are given above and NBS is N-bromosuccinimide.

Scheme 4

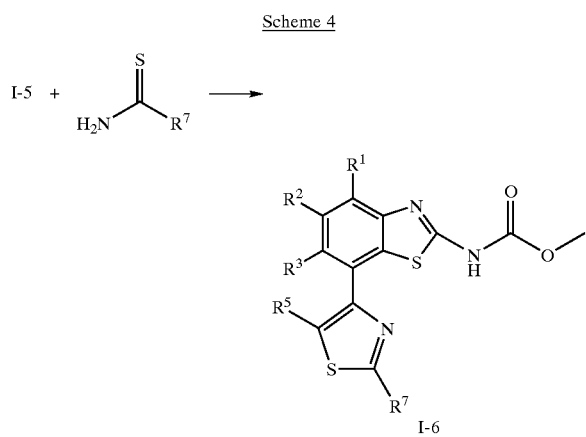

The definitions of $R^1$ to $R^5$ and $R^7$ are given above.

Scheme 5

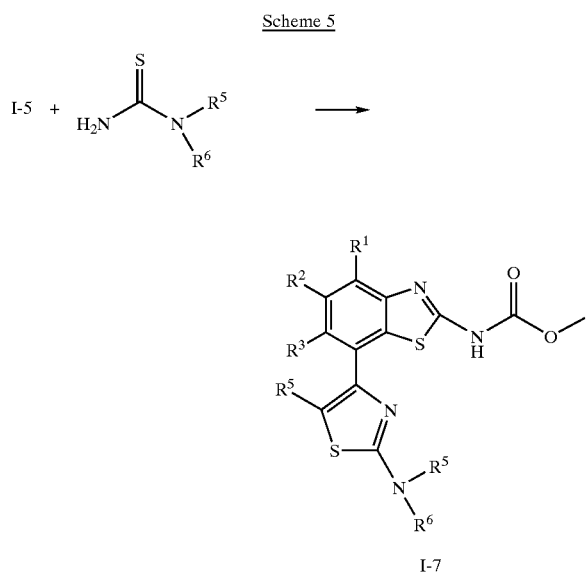

The definitions of $R^1$ to $R^6$ are given above.

Scheme 6

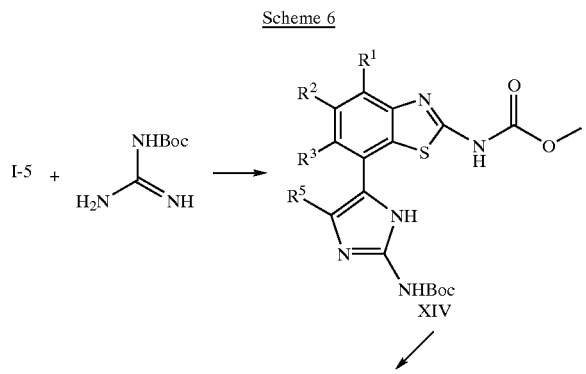

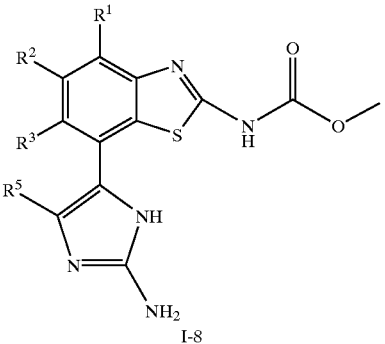

The definitions of $R^1$ to $R^5$ are given above.

The reactions described in schemes 1 to 6 are carried out in conventional manner.

The compounds of formulas I and I-A and their pharmaceutically usable addition salts possess valuable pharmacological properties. Specifically, it has been found that the compounds of the present invention are adenosine receptor ligands and possess a high affinity towards the adenosine $A_{2A}$ receptor.

All of the compounds were investigated in accordance with the test given hereinafter.

Human Adenosine $A_{2A}$ Receptor

The human adenosine $A_{2A}$ receptor was recombinantly expressed in chinese hamster ovary (CHO) cells using the semliki forest virus expression system. Cells were harvested, washed twice by centrifugation, homogenised and again washed by centrifugation. The final washed membrane pellet was suspended in a Tris (50 mM) buffer containing 120 mM NaCl, 5 mM KCl, 2 mM $CaCl_2$ and 10 mM $MgCl_2$ (pH 7.4) (buffer A). The [$^3$H]-SCH-58261 (Dionisotti et al., 1997, Br J Pharmacol 121, 353; 1 nM) binding assay was carried out in 96-well plates in the presence of 2.5 µg of membrane protein, 0.5 mg of Ysi-poly-1-lysine SPA beads and 0.1 U adenosine deaminase in a final volume of 200 µl of buffer A. Non-specific binding was defined using xanthine amine congener (XAC; 2 µM). Compounds were tested at 10 concentrations from 10 µM–0.3 nM. All assays were conducted in duplicate and repeated at least two times. Assay plates were incubated for 1 hour at room temperature before centrifugation and then bound ligand determined using a Packard Topcount scintillation counter. $IC_{50}$ values were calculated using a non-linear curve fitting program and Ki values calculated using the Cheng-Prussoff equation.

In accordance with the invention, it has been shown that all of the compounds of formula I have a high affinity toward the $A_{2A}$ receptor. The most preferred compounds show an affinity to the hA2A binding in the scope of a pKi value between 8.5 to 9.3.

Examples of such compounds are the followings:

| Example No. | pKi value |
|---|---|
| 3 | 8.8 |
| 10 | 9.0 |
| 17 | 9.3 |
| 23 | 8.9 |
| 36 | 9.1 |
| 59 | 9.0 |

-continued

| Example No. | pKi value |
|---|---|
| 61 | 8.9 |
| 62 | 9.1 |
| 91 | 8.8 |
| 92 | 8.9 |
| 96 | 8.8 |
| 100 | 9.3 |
| 107 | 8.8 |
| 108 | 8.9 |
| 121 | 9.0 |
| 125 | 9.0 |
| 157 | 8.9 |
| 159 | 8.9 |
| 201 | 8.6 |
| 221 | 8.7 |
| 238 | 8.7 |
| 240 | 8.5 |
| 253 | 8.6 |
| 258 | 8.9 |
| 271 | 8.6 |
| 275 | 8.7 |
| 277 | 8.7 |
| 278 | 8.5 |
| 279 | 8.8 |
| 280 | 8.7 |
| 282 | 8.6 |
| 283 | 9.0 |
| 286 | 8.8 |
| 287 | 8.5 |
| 289 | 8.9 |
| 290 | 8.6 |
| 292 | 8.8 |
| 298 | 8.7 |
| 301 | 8.5 |
| 304 | 8.5 |
| 308 | 9.1 |
| 309 | 8.5 |
| 314 | 8.5 |
| 315 | 8.6 |
| 317 | 8.6 |
| 326 | 8.5 |
| 327 | 8.5 |
| 342 | 8.5 |
| 369 | 9.2 |

The compounds of formula I, formula Ia and the pharmaceutically acceptable salts of the compounds of formula I and formula Ia can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, parenterally, e.g. in the form of injection solutions.

The compounds of formula I and formula Ia can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I, formula Ia or a pharmaceutically acceptable salt thereof and a therapeutically inert carrier are also an object of the present invention, as is a process for their production, which comprises bringing one or more compounds of formula I and/or pharmaceutically acceptable acid addition salts and, if desired, one or more other therapeutically valuable substances into a galenical administration form together with one or more therapeutically inert carriers.

In accordance with the invention compounds of formula I and formula Ia as well as their pharmaceutically acceptable salts are useful in the control or prevention of illnesses based on the adenosine receptor antagonistic activity, such as Alzheimer's disease, Parkinson's disease, neuroprotection, schizophrenia, anxiety, pain, respiration deficits, depression, asthma, allergic responses, hypoxia, ischaemia, seizure and substance abuse. Furthermore, compounds of the present invention may be useful as sedatives, muscle relaxants, antipsychotics, antiepileptics, anticonvulsants and cardiaprotective agents and for the production of corresponding medicaments.

The most preferred indications in accordance with the present invention are those, which include disorders of the central nervous system, for example the treatment or prevention of certain depressive disorders, neuroprotection and Parkinson's disease.

The dosage can vary within wide limits and will, of course, have to be adjusted to the individual requirements in each particular case. In the case of oral administration the dosage for adults can vary from about 0.01 mg to about 1000 mg per day of a compound of formula I, formula Ia or of the corresponding amount of a pharmaceutically acceptable salt thereof. The daily dosage may be administered as single dose or in divided doses and, in addition, the upper limit can also be exceeded when this is found to be indicated.

EXAMPLE 1

N-(4-Methoxy-7-phenyl-benzothiazol-2-yl)-benzamide

To a solution of 2-amino-4-methoxy-7-phenyl-benzothiazole (100 mg, 0.4 mmol) in pyridine (2 ml) was added benzoyl chloride (55 mg, 0.4 mmol) and the mixture stirred overnight at 20° C. To this mixture 2N HCl to pH 1 (20 ml) was added then the mixture was extracted twice with EtOAc (20 ml), washed with saturated $NaHCO_3$ solution, dried with $Na_2SO_4$ and the solvent evaporated. The crude product was then chromatographed over $SiO_2$ (Merck 230–400 mesh) eluting with $CH_2Cl_2$/MeOH (98:2), the product fractions were pooled and the solvent evaporated, to afford the title compound as a white solid (97 mg, 69% yield), MS: m/e=360 ($M^+$).

Following the General Method of Example 1 the Compounds of Examples 2 to 49 were Prepared

EXAMPLE 2

Furan-2-carboxylic acid (4-methoxy-7-phenyl-benzothiazol-2-yl)-amide

Using furan-2-carboxylic acid chloride the title compound was prepared as a beige solid (41% yield), MS: m/e=251.3 ($M+H^+$).

EXAMPLE 3

5-Methyl-thiophene-2-carboxylic acid (4-methoxy-7-phenyl-benzothiazol-2-yl)-amide Using 5-methyl-thiophene-carboxylic acid chloride the title compound was prepared as a beige solid (36% yield), MS: m/e=381.3 (M+H$^+$).

EXAMPLE 4

Furan-2-carboxylic acid (4,6-difluoro-benzothiazol-2-yl)-amide

Using 2-amino-4,6-difluoro-benzothiazole and furan-2-carboxylicacid chloride the title compound was prepared as a grey solid (81% yield), MS: m/e=280 (M$^+$).

EXAMPLE 5

5-Methyl-thiophene-2-carboxylic acid (4,6-difluoro-benzothiazol-2-yl)-amide

Using 2-amino-4,6-difluoro-benzothiazole and 5-methyl-thiophene-carboxylicacid chloride the title compound was prepared as a yellow solid (74% yield), MS: m/e=310 (M$^+$).

EXAMPLE 6

N-(4,6-Difluoro-benzothiazol-2-yl)-benzamide

Using 2-amino-4,6-difluoro-benzothiazole and benzoyl chloride the title compound was prepared as a beige solid (82% yield), MS: m/e=290 (M$^+$).

EXAMPLE 7

N-(4-Methoxy-7-phenyl-benzothiazol-2-yl)-acetamide

Using acetyl chloride the title compound was prepared as a light brown solid (69% yield), MS: m/e=299.2 (M+H$^+$).

EXAMPLE 8

4-Cyano-N-(4-methoxy-7-phenyl-benzothiazol-2-yl)-benzamide

Using 4-cyano-benzoyl chloride the title compound was prepared as yellow solid (84% yield), MS: m/e=385.1 (M$^+$).

EXAMPLE 9

5-Methyl-thiophene-2-carboxylic acid (4-methoxy-benzothiazol-2-yl)-amide

Using 2-amino-4-methoxy-benzothiazole and 5-methyl-thiophene-2-carboxylic acid chloride in pyridine the title compound was obtained as a beige solid (95% yield), MS: m/e=304.1 (M$^+$).

EXAMPLE 10

5-Methyl-furan-2-carboxylic acid (4-methoxy-7-phenyl-benzothiazol-2-yl)-amide

Using 2-amino-4-methoxy-7-phenyl-benzothiazole and freshly prepared 5-methyl-furan-2-carboxylic acid chloride the title compound was obtained crude, which was chromatographed over SiO$_2$ (Merck 230–400 mesh) eluting with nHexane/EtOAc (4:1), to afford the pure title compound as a pale yellow solid (67% yield), MS: m/e=364.0 (M$^+$).

EXAMPLE 11

Furan-2-carboxylic acid (4-methoxy-benzothiazol-2-yl)-amide

Using 2-amino-4-methoxy-benzothiazole and furan-2-carboxylic acid chloride in pyridine the title compound was obtained as a tan solid (100% yield), MS: m/e=274.1 (M$^+$).

EXAMPLE 12

N-(4-Methoxy-benzothiazol-2-yl)-benzamide

Using 2-amino-4-methoxy-benzothiazole and benzoyl chloride in pyridine the title compound was obtained as a white solid (72% yield), MS: m/e=284.1 (M$^+$).

EXAMPLE 13

Benzo[b]thiophene-2-carboxylic acid benzothiazol-2-ylamide

Using 2-amino-benzothiazole and benzo[b]thiophene-2-carboxylic acid chloride in pyridine the title compound was obtained as a light yellow solid (86% yield), MS: m/e=311.1 (M+H$^+$).

EXAMPLE 14

3-Methyl-thiophene-2-carboxylic acid benzothiazol-2-ylamide

Using 2-amino-benzothiazole and 3-methyl-thiophene-2-carboxylic acid chloride in pyridine the title compound was obtained as a yellow solid (69% yield), MS: m/e=275.1 (M+H$^+$).

EXAMPLE 15

5-Methyl-thiophene-2-carboxylic acid benzothiazol-2-ylamide

Using 2-amino-benzothiazole and 5-mrthyl-thiophene-2-carboxylic acid chloride in pyridine the title compound was obtained as a yellow solid (87% yield), MS: m/e=275.1 (M+H$^+$).

EXAMPLE 16

N-Benzothiazol-2-yl-6-chloro-nicotinamide

Using 2-amino-benzothiazole and 2-chloropyridine-5-carboxylic acid chloride in pyridine the title compound was obtained as a white solid (97% yield), MS: m/e=290.1 (M+H$^+$).

EXAMPLE 17

4-Hydroxymethyl-N-(4-methoxy-7-phenyl-benzothiazol-2-yl)-benzamide

To a solution of 4-formyl-N-(4-methoxy-7-phenyl-benzothiazol-2-yl)-benzamide (194 mg, 0.5 mmol), in THF (40 ml) was added sodium borohydride (19 mg, 0.5 mmol) and the mixture stirred for 2 h at r.t. Water was added (30 ml) followed by 1N HCl (4 ml) and the mixture agitated. The aqueous phase was then extracted twice with EtOAc (30 ml), the combined organic phases were then washed with saturated NaCl solution, dried with Na$_2$SO$_4$ filtered and evaporated. The crude residue was suspended in ether and ultrasonnicated for 10 min., the solid precipitate was filterted off, washed with ether then dried under vacuum (0.05 mmHg,

EXAMPLE 18

4-Formyl-N-(4-methoxy-7-phenyl-benzothiazol-2-yl)-benzamide

Using 4-formyl benzoic acid the title compound was obtained as a light yellow solid (73% yield), MS: m/e=388.1 (M+H$^+$).

EXAMPLE 19

2-Methoxy-N-(4-methoxy-7-phenyl-benzothiazol-2-yl)-benzamide

To a solution of 2-amino-4-methoxy-7-phenyl-benzothiazole (200 mg, 0.67 mmol) in THF (10 m) was added DMAP (10 mg, 0.08 mmol), triethylamine (163 □l, 1.17 mmol) and 2-methoxybenzoyl chloride (136 □l, 1 mmol) in THF (2 ml). The mixture was then heated to reflux for 2 h, after cooling, it was partitioned between 1:1 AcOEt/THF (70 ml) and 5% NaHCO$_3$ solution( 40 ml). The organic phase was washed with saturated NaCl solution (50 ml), dried with Na$_2$SO$_4$, filtered and the solvent removed under reduced presure. The residue was suspended in ether (10 ml), filtered, washed with ether then dried under vacuum (0.05 mmHg, 60° C.), to afford the title compound was a white solid (260 mg, 85% yield), MS: m/e=390.0 (M$^+$).

EXAMPLE 20

N-(4-Methoxy-7-phenyl-benzothiazol-2-yl)-2-methyl-benzamide

Using 2-methyl-benzoyl chloride the title compound was obtained crude, which was chromatographed over SiO$_2$ (Merck 230–400 mesh) eluting with CH$_2$Cl$_2$/EtOAc (1:1), to afford the pure title compound as a white solid, (88% yield), MS: m/e=374.1 (M$^+$).

EXAMPLE 21

N-(4-Methoxy-7-phenyl-benzothiazol-2-yl)-3-methyl-benzamide

Using 3-methyl-benzoyl chloride the title compound was obtained crude, which was chromatographed over SiO$_2$ (Merck 230–400 mesh) eluting with CH$_2$Cl$_2$/EtOAc (1:1), to afford the pure title compound as a light yellow solid, (80% yield), MS: m/e=374.0 (M$^+$).

EXAMPLE 22

N-(4-Methoxy-7-phenyl-benzothiazol-2-yl)-4-methyl-benzamide

Using 4-methyl-benzoyl chloride the title compound was obtained crude, which was chromatographed over SiO$_2$ (Merck 230–400 mesh) eluting with CH$_2$Cl$_2$/EtOAc (1:1), to afford the pure title compound as a white solid, (79% yield), MS: m/e=374.1 (M$^+$).

EXAMPLE 23

4-Fluoro-N-(4-methoxy-7-phenyl-benzothiazol-2-yl)-benzamide

Using 4-fluoro-benzoyl chloride the title compound was obtained crude, which was chromatographed over SiO$_2$ (Merck 230–400 mesh) eluting with CH$_2$Cl$_2$/EtOAc (1:1), to afford the pure title compound as a white solid (68% yield), MS: m/e=378.0 (M$^+$).

EXAMPLE 24

3-Methoxy-N-(4-methoxy-7-phenyl-benzothiazol-2-yl)-benzamide

Using 3-methoxy-benzoyl chloride the title compound was obtained crude, which was chromatographed over SiO$_2$ (Merck 230–400 mesh) eluting with CH$_2$Cl$_2$/EtOAc (1:1), to afford the pure title compound as a light yellow foam (75% yield), MS: m/e=390.0 (M$^+$).

EXAMPLE 25

4-Methoxy-N-(4-methoxy-7-phenyl-benzothiazol-2-yl)-benzamide

Using 4-methoxy-benzoyl chloride the title compound was obtained crude, which was chromatographed over SiO$_2$ (Merck 230–400 mesh) eluting with CH$_2$Cl$_2$/EtOAc (1:1), to afford the pure title compound as a white foam (79% yield), MS: m/e=390.1 (M$^+$).

EXAMPLE 26

N-(4-Methoxy-7-phenyl-benzothiazol-2-yl)-2-phenyl-acetamide

Using phenylacetyl-chloride chloride the title compound was obtained crude, which was chromatographed over SiO$_2$ (Merck 230–400 mesh) eluting with CH$_2$Cl$_2$/EtOAc (1:1), to afford the pure title compound as a white solid (29% yield), MS: m/e=374.1 (M$^+$).

EXAMPLE 27

3-Methyl-thiophene-2-carboxylic acid (4-methoxy-7-phenyl-benzothiazol-2-yl)-amide Using 3-methyl-thiophene-2-carboxylicacid chloride the title compound was obtained crude, which was chromatographed over SiO$_2$ (Merck 230–400 mesh) eluting with CH$_2$Cl$_2$/EtOAc (1:1), to afford the pure title compound as a white solid (64% yield), MS: m/e=380.0 (M$^+$).

EXAMPLE 28

2,5-Dimethyl-furan-3-carboxylic acid (4-methoxy-7-phenyl-benzothiazol-2-yl)-amide Using 2,5-dimethyl-furan-3-carboxylicacid chloride the title compound was obtained crude, which was chromatographed over SiO$_2$ (Merck 230–400 mesh) eluting with CH$_2$Cl$_2$/EtOAc (1:1), to afford the pure title compound as a white solid (73% yield), MS: m/e=378.1 (M$^+$).

EXAMPLE 29

3-Cyano-N-(4-methoxy-7-phenyl-benzothiazol-2-yl)-benzamide

Using 3-cyano-benzoyl chloride the title compound was obtained crude, which was chromatographed over SiO$_2$ (Merck 230–400 mesh) eluting with CH$_2$Cl$_2$/EtOAc (1:1), to afford the pure title compound as a white solid (80% yield), MS: m/e=385.0 (M$^+$).

EXAMPLE 30

N-(4-Methoxy-7-phenoxy-benzothiazol-2-yl)-benzamide

Using 4-Methoxy-7-phenoxy-benzothiazol-2-ylamine and benzoyl chloride the title compound was obtained crude, (50° C.) to afford the title compound as a light yellow solid (150 mg, 77% yield), MS: m/e=390.0 (M$^+$).

EXAMPLE 31

4-Dimethylamino-N-(4-methoxy-7-phenyl-benzothiazol-2-yl)-benzamide

Using 4-dimethylamino-benzoyl chloride in pyridine the title compound was obtained crude, which was chromatographed over SiO$_2$ (Merck 230–400 mesh) eluting with CH$_2$Cl$_2$/(2N NH$_3$ in MeOH) (19:1), to afford the pure title compound as a beige solid (70% yield), MS: m/e=403.0 (M$^+$).

EXAMPLE 32

4-Fluoro-N-(4-methoxy-7-phenyl-benzothiazol-2-yl)-N-methyl-benzamide

Using (4-mmethoxy-7-phenyl-benzothiazol-2-yl)-methyl-amine and 4-fluoro-benzoyl chloride in pyridine the title compound was obtained crude, which was chromatographed over SiO$_2$ (Merck 230–400 mesh) eluting with CH$_2$Cl$_2$/EtOAc (1:1), to afford the pure title compound as a beige solid (88% yield), MS: m/e=393.2 (M+H$^+$).

EXAMPLE 33

2-(4-Fluoro-benzoylamino)-4-methoxy-benzothiazole-7-carboxylic acid methyl ester Using 2-amino-4-methoxy-benzothiazole-7-carboxylic acid methyl ester and 4-fluoro-benzoyl chloride the title compound was obtained as a white solid (91% yield), MS: m/e=361.1 (M+H$^+$).

EXAMPLE 34

N-(7-tert-Butyl-4-methoxy-benzothiazol-2-yl)-4-fluoro-benzamide

Using 7-tert-butyl-4-methoxy-benzothiazol-2-ylamine and 4-fluoro-benzoyl chloride the title compound was obtained as a white solid (75% yield), MS: m/e=258.1 (M+H$^+$).

EXAMPLE 35

N-(7-Acetylamino-4-methoxy-benzothiazol-2-yl)-4-fluoro-benzamide

Using 7-acetylamino-4-methoxy-benzothiazol-2-ylamine and 4-fluoro-benzoyl chloride the title compound was obtained as a tan solid (25% yield), MS: m/e=359.1 (M+H$^+$).

EXAMPLE 36

N-(4-Methoxy-7-phenyl-benzothiazol-2-yl)-isonicotinamide

Using pyridine-4-carboxylic acid chloride hydrochloride salt in pyridine the title compound was obtained crude. After cooling a solid precipitated from the reaction mixture which was further triturated with ether (10 ml) then collected on a glass sinter and further washed with ether (10 ml). The filter cake was then washed sequentially with 10% Na$_2$CO$_3$ (20 ml), water (20 ml) followed by ether (20 ml) and the resulting product dried under vacuum (0.05 mmHg, 60° C.) to afford the pure title compound as a yellow solid (188 mg, 67% yield), MS: m/e=361.0 (M$^+$).

EXAMPLE 37

4-Fluoro-N-(4-methoxy-7-phenoxy-benzothiazol-2-yl)-benzamide

Using 4-methoxy-7-phenoxy-benzothiazol-2-ylamine and 4-fluoro-benzoyl chloride the title compound was obtained crude, which was chromatographed over SiO$_2$ (Merck 230–400 mesh) eluting with CH$_2$Cl$_2$/EtOAc (1:1), to afford the pure title compound as a white solid (75% yield), MS: m/e=394.1 (M$^+$).

EXAMPLE 38

5-Methyl-thiophene-2-carboxylic acid (4-methoxy-7-phenoxy-benzothiazol-2-yl)-amide Using 4-methoxy-7-phenoxy-benzothiazol-2-ylamine and 5-methyl-thiophene-2-carboxylic acid chloride the title compound was obtained crude, which was chromatographed over SiO$_2$ (Merck 230–400 mesh) eluting with CH$_2$Cl$_2$/EtOAc (1:1), to afford the pure title compound as a pale yellow solid (76% yield), MS: m/e=396.0 (M$^+$).

EXAMPLE 39

4-Fluoro-N-(4-methoxy-7-morpholin-4-ylmethyl-benzothiazol-2-yl)-benzamide

Using 4-methoxy-7-morpholin-4-ylmethyl-benzothiazol-2-ylamine and 4-fluoro-benzoyl chloride in pyridine the title compound was obtained as a yellow solid (44% yield), MS: m/e=402.4 (M+H$^+$).

EXAMPLE 40

5-Methyl-thiophene-2-carboxylic acid (4-methoxy-7-morpholin-4-ylmethyl-benzothiazol-2-yl)-amide Using 4-methoxy-7-morpholin-4-ylmethyl-benzothiazol-2-ylamine and 5-methyl-thiophene-2-carboxylic acid chloride in pyridine the title compound was obtained as a yellow solid (53% yield), MS: m/e=404.4 (M+H$^+$).

EXAMPLE 41

4-Fluoro-N-[4-methoxy-7-(1H-tetrazol-5-yl)-benzothiazol-2-yl]-benzamide

Using 4-methoxy-7-(1H-tetrazol-5-yl)-benzothiazol-2-ylamine and 4-fluoro-benzoyl chloride in pyridine the title compound was obtained as a tan solid (70% yield), MS: m/e=371.2 (M+H$^+$).

EXAMPLE 42

N-Benzothiazol-2-yl-benzamide

Using 2-amino-benzothiazole and benzoyl chloride in pyridine the title compound was obtained as a white solid (87% yield), MS: m/e=255.1 (M+H$^+$).

EXAMPLE 43

Furan-2-carboxylic acid benzothiazol-2-ylamide

Using 2-amino-benzothiazole and furan-2-carboxylic acid chloride in pyridine the title compound was obtained as a white solid (83% yield), MS: m/e=244 (M$^+$).

EXAMPLE 44

2-Chloro-N-(4-methyl-2-benzothiazolyl)-nicotinamide

Using 4-methyl-benzothiazol-2-ylamine and 2-chloronicotinic acid chloride the title compound was obtained as a yellow solid (50% yield), MS: m/e=304 (M+H$^+$).

EXAMPLE 45

2-chloro-N-(4-methoxy-2-benzothiazolyl-nicotinamide

Using 4-methoxy-benzothiazol-2-ylamine and 2-chloronicotinic acid chloride the title compound was obtained as a off-white solid (50% yield). MS: m/e=320 (M+H$^+$).

EXAMPLE 46

3-(4-Methoxy-benzothiazol-2-ylcarbamoyl)-acrylic acid ethyl ester

Using 4-methoxy-benzothiazol-2-ylamine and 3-chlorocarbonyl-acrylic acid methyl ester the title compound was obtained as a off-white solid (50% yield). MS: m/e=307 (M$^+$).

EXAMPLE 47

N-(4-Methoxy-7-phenyl-benzothiazol-2-yl)-oxalamic acid ethyl ester

The title compound is described in the following patent literature and was prepared according to the procedure described therin. N-(Benzothiazol-2-yl)oxamic acid derivatives. W. Winter, M. Thiel, A. Roesch and O. H. Wilhelms, German Patent, DE 2656468, 1978. Mp. 138–142° C., MS: m/e=357 (M+H$^+$).

EXAMPLE 48

4-Dimethylamino-N-(4-methoxy-7-phenyl-benzothiazol-2-yl)-benzamide

Using pyridine-2-carboxylic acid, chloride hydrochloride salt in pyridine the title compound was obtained crude. This compound was purified further with preparative reversed phase HPLC using a Nucleosil N-proteced column (20 mm×50 mm) and eluting with a gradient of MeCN/water (0.1% TFA), The product fractions were pooled, evaporated and the residue partitioned between EtOAc (30 ml) and 10% Na$_2$CO$_3$ (30 ml) and the aqueous phase extrteacted once with EtOAc (30 ml) The combind organic phases were then washed with satuarated NaCl,. dried, fitered and evaporated to afford the pure title compound as a beige solid (110 mg, 39% yield), MS: m/e=361.1 (M$^+$).

EXAMPLE 49

4-Fluoro-N-(7-hydroxymethyl-4-methoxy-benothiazol-2-yl)benzamide

To a solution of 2-(4-fluoro-benzoylamino)-4-methoxy-benzothiazole-7-carboxylic acid methyl ester (1.1 g, 3.05 mmol) in THF (250 ml) uner argon at 5° C. was added a solution of 1N LiAlH$_4$ in THF (2 ml, 2 mmol) over 5 min., the mixture was stirred for 1 h at 5° C., then over 1 h allowed to warm to 20° C. A further 3.5 ml of 1N LiAlH$_4$/THF was then added dropwise and the mixture stirred a further 2 h at 20° C. A solution of 5 ml THF/Water (4:1) was then added cautiosly followed by 4N NaOH (2 ml), then water (2 ml) and the mixture stirred vigorously for 15 min. Excess Na$_2$SO$_4$ (50 g) was then added with vigorous stirring, then the solution was filtered and the solvent evaporated to afford ther title compound as a white solid (0.9 g, 89% yield), MS: m/e=333.2 (M+H$^+$).

EXAMPLE 50

4-Dipropylsulfamoyl-N-(4-methoxy-7-phenyl-benzothiazol-2-yl)-benzamide

To a suspension of 4-dipropylsulfamoyl-benzoic acid (185 mg, 0.65 mmol) in toluene (10 ml) was added thionylchloride (600 mg, 5 mmol) and the mixture heated to 80° C. for 17 h. After cooling the solvent was evaporated and the resudue was taken up in THF (20 ml), 2-amino-4-methoxy-7-phenyl-benzothiazole (128 mg, 0.5 mmol), triethylamine (105 µl, 0.75 mmol), and DMAP (6 mg, 0.05 mmol) were then added and the mixture was stirred for 1 hour at r.t. followed by 1 hour at 60° C. After cooling to r.t. the reaction mixture was quenched by addition of 10% aq. Na$_2$CO$_3$ solution (30 ml) and EtOAc (30 ml) and vigorous stirring. After separation of the phases the aqueous phase was extracted with EtOAc (30 ml) and the combined orgainc phases were washed with 10% aq. Na$_2$CO$_3$, dried with Na$_2$SO$_4$, filtered and evaporated. The residue was then chromatographed over SiO$_2$ (Merck 230–400 mesh) eluting with a gradient of cyclohexane/EtOAc from (1:4) to 100% EtOAc. After pooling and evaporation of the product fractions the title compound was obtained as a white solid (240 mg, 92% yield), MS: m/e=524.2 (M+H$^+$).

Following the General Method of Example 50 the Compounds of Examples 51 to 53 were Prepared

EXAMPLE 51

4-Diethylsulfamoyl-N-(4-methoxy-7-phenyl-benzothiazol-2-yl)-benzamide

Using 4-diethylsulfamoyl-benzoic acid the title compound was obtained as a light yellow solid (81% yield), MS: m/e=496.2 (M+H$^+$).

EXAMPLE 52

N-(4-Methoxy-7-phenyl-benzothiazol-2-yl)-4-(morpholine-4-sulfonyl)-benzamide Using 4-(morpholine-4-sulfonyl)-benzoic acid the title compound was obtained as white amorphous solid (32% yield), MS: m/e=510.3 (M+H$^+$).

EXAMPLE 53

4-Ethylsulfamoyl-N-(4-methoxy-7-phenyl-benzothiazol-2-yl)-benzamide

Using 4-ethylsulfamoyl-benzoic acid the title compound was obtained as pale yellow amorphous solid (20% yield), MS: m/e=466.2 (M–H)$^-$.

EXAMPLE 54

5-Methyl-thiophene-2-carboxylic acid (7-iodo-4-methoxy-benzothiazol-2-yl)-amide Iodination of 5-methyl-thiophene-2-carboxylic acid (4-methoxy-benzothiazol-2-yl)-amide (5.17 g, 17 mmol)

with iodine monochloride (2.26 ml, 44 mmol), sodium acetate (3.63 g, 44 mmol) and acetic acid (200 ml) in the same manner as described for (4-methoxy-benzothiazol-2-yl)-carbamic acid methyl ester affords the product as off-white solid in 93% yield. MS: m/e=430 (M+).

(7-Aryl-4-methoxy-benzothiazol-2-yl)-carbamic acid ester, aryl-carboxylic acid (7-aryl-4-methoxy-benzothiazol-2-yl)-amides and substituted (4-methoxy-7-aryl-benzothiazol-2-yl)-ureas:

General procedure A: (7-Iodo-4-methoxy-benzothiazol-2-yl)-carbamic acid ester or the respective aryl-carboxylic acid (7-iodo-4-methoxy-benzothiazol-2-yl)-amide or the respective (4-methoxy-7-aryl-benzothiazol-2-yl)-urea (1 part), the appropriate boronic acid (or its ester) (1.5 equivalents), palladium(II) acetate (0.05 equivalents), potassium phosphate (2.5 equivalents) and 2-biphenyl-dicyclohexyl phosphine (0.1 equivalents) are combined in toluene (20 parts) and heated in an atmosphere of argon to 65° C. for 12 hours. The reaction mixture is evaporated to dryness and the product isolated by flash chromatography (silica, eluent ethyl acetate/cyclohexane 2:1).

General procedure B: (7-Iodo-4-methoxy-benzothiazol-2-yl)-carbamic acid ester or the respective aryl-carboxylic acid (7-iodo-4-methoxy-benzothiazol-2-yl)-amide amide or the respective (4-methoxy-7-aryl-benzothiazol-2-yl)-urea (1 part), the appropriate aryltrimethylstannane (1.5 equivalents), triphenylarsine (0.5 equivalents), tris-(dibenzylideneacetone)-dipalladium(0) (0.8 equivalents) and copper(I)iodide (0.8 equivalents) are combined in dimethylformamide (25 parts) and heated to 80° C. for 12 hours. The reaction mixture is evaporated to dryness and the product isolated by flash chromatography (silica, eluent ethyl acetate).

Following the General Method the Compounds of Examples 55 to 62 were Prepared

EXAMPLE 55

5-Methyl-thiophene-2-carboxylic acid [7-(2-chloro-phenyl)-4-methoxy-benzothiazol-2-yl]-amide 5-Methyl-thiophene-2-carboxylic acid [7-(2-chloro-phenyl)-4-methoxy-benzothiazol-2-yl]-amide is synthesized from 5-methyl-thiophene-2-carboxylic acid (7-iodo-4-methoxy-benzothiazol-2-yl)-amide (100 mg, 0.23 mmol) and 2-chlorophenylboronic acid (54 mg, 0.35 mmol) using the general procedure A as a light yellow solid in 80% yield. MS: m/e=415 (M+H+).

EXAMPLE 56

5-Methyl-thiophene-2-carboxylic acid [4-methoxy-7-(3-nitro-phenyl)-benzothiazol-2-yl]-amide 5-Methyl-thiophene-2-carboxylic acid [7-(3-nitro-phenyl)-4-methoxy-benzothiazol-2-yl]-amide is synthesized from 5-methyl-thiophene-2-carboxylic acid (7-iodo-4-methoxy-benzothiazol-2-yl)-amide (155 mg, 0.36 mmol) and 3-nitrophenylboronic acid (135 mg, 0.81 mmol) using the general procedure A as a light yellow crystals in 42% yield. MS: m/e=425 (M+).

EXAMPLE 57

5-Methyl-thiophene-2-carboxylic acid [7-(3-dimethylamino-phenyl)-4-methoxy-benzo-thiazol-2-yl]-amide 5-Methyl-thiophene-2-carboxylic acid [7-(3-dimethylamino-phenyl)-4-methoxy-benzothiazol-2-yl]-amide is synthesized from 5-methyl-thiophene-2-carboxylic acid (7-iodo-4-methoxy-benzothiazol-2-yl)-amide (100 mg, 0.23 mmol) and 3-dimethylaminophenylboronic acid (58 mg, 0.35 mmol) using the general procedure A as a light yellow solid in 71% yield. MS: m/e=424 (M+H+).

EXAMPLE 58

5-Methyl-thiophene-2-carboxylic acid (4-methoxy-7-pyridin-4-yl-benzothiazol-2-yl)-amide 5-Methyl-thiophene-2-carboxylic acid (4-methoxy-7-pyridin-4-yl-benzothiazol-2-yl)-amide is synthesized from 5-methyl-thiophene-2-carboxylic acid (7-bromo-4-methoxy-benzothiazol-2-yl)-amide (192 mg, 0.50 mmol) and 4-pyridylboronic acid (92 mg, 0.75 mmol) using the general procedure A as a white solid in 6% yield. MS: m/e=381 (M+).

EXAMPLE 59

5-Methyl-thiophene-2-carboxylic acid (4-methoxy-7-pyridin-3-yl-benzothiazol-2-yl)-amide 5-Methyl-thiophene-2-carboxylic acid (4-methoxy-7-pyridin-3-yl-benzothiazol-2-yl)-amide is synthesized from 5-methyl-thiophene-2-carboxylic acid (7-bromo-4-methoxy-benzothiazol-2-yl)-amide (192 mg, 0.50 mmol) and 4-pyridylboronic acid (123 mg, 1.0 mmol) using the general procedure A as a white solid in 8% yield. MS: m/e=381 (M+).

EXAMPLE 60

5-Methyl-thiophene-2-carboxylic acid (4-methoxy-7-pyridin-2-yl-benzothiazol-2-yl)-amide 65-Methyl-thiophene-2-carboxylic acid (4-methoxy-7-pyridin-2-yl-benzothiazol-2-yl)-amide is synthesized from 5-methyl-thiophene-2-carboxylic acid (7-iodo-4-methoxy-benzothiazol-2-yl)-amide (100 mg, 0.23 mmol) and 2-tri-n-butylstannane (130 mg, 0.35 mmol) using the general procedure B as a white solid in 23% yield. MS: m/e=382 (M+H+).

EXAMPLE 61

5-Methyl-thiophene-2-carboxylic acid [4-methoxy-7-(2-methyl-pyridin-4-yl)-benzothiazol-2-yl]-amide 5-Methyl-thiophene-2-carboxylic acid [4-methoxy-7-(2-methyl-pyridin-4-yl)-benzothiazol-2-yl]-amide is synthesized from 5-methyl-thiophene-2-carboxylic acid (4-methoxy-7-iodo-benzothiazol-2-yl)-amide (260 mg, 0.60 mmol) and 2-methyl-4-trimethylstannanyl-pyridine (384 mg, 0.90 mmol) using the general procedure B as a light yellow solid in 50% yield. MS: m/e=396 (M+H+).

EXAMPLE 62

5-Methyl-thiophene-2-carboxylic acid [7-(3-amino-phenyl)-4-methoxy-benzothiazol-2-yl]-amide 5-Methyl-thiophene-2-carboxylic acid [7-(3-amino-phenyl)-4-methoxy-benzothiazol-2-yl]-amide is synthesized from 5-methyl-thiophene-2-carboxylic acid (4-methoxy-7-iodo-benzothiazol-2-yl)-amide (300 mg, 0.70 mmol) and 3-trimethylstannanyl-phenylamine (291 mg, 1.14 mmol) using the general procedure B as a light brown solid in 56% yield. MS: m/e=396 (M+H+).

EXAMPLE 63

5-Methyl-thiophene-2-carboxylic acid (4-hydroxy-7-phenyl-benzothiazol-2-yl)-amide A solution of 5-methyl-thiophene-2-carboxylic acid (4-methoxy-7-phenyl-benzothiazol-2-yl)-amide (630 mg, 1.7 mmol) is slowly trated with boron tribromide (16 ml, 1.0 M in dichloromethane) at 0° C. The reaction is slowly warmed to ambient temperature and stirred for further 72 h. The mixture is diluted with ethyl acetate and extracted twice with water and once with brine. After drying over sodium sulfate, the solvent is removed in vacuo. Flash chromatography (silica, eluent ethyl acetate/hexane 1:1) and final recrystallization from tetrahydrofurane/hexane yields 118 mg (19%) of the product as white solid. MS: m/e=367 (M+H$^+$).

EXAMPLE 64

4-{4-Methoxy-2-[(5-methyl-thiophene-2-carbonyl)-amino]-benzothiazol-7-yl}-piperazine-1-carboxylic acid benzyl ester The title compound was synthesized starting from N-benzyloxycarbonylpiperazine and 4-bromo-2-nitroanisole as described for 5-methyl-thiophene-2-carboxylic acid (4-methoxy-7-morpholin-4-yl-benzothiazol-2-yl)-amide and obtained as a white solid in 12% overall yield, MS: m/e=523 (M+H$^+$).

EXAMPLE 65

5-Methyl-thiophene-2-carboxylic acid [7-(3-dimethylamino-pyrrolidin-1-yl)-4-methoxy-benzothiazol-2-yl]-amide The title compound is synthesized starting from 3-(dimethylamino)pyrrolidine and 4-bromo-2-nitroanisole as described for 5-methyl-thiophene-2-carboxylic acid (4-methoxy-7-morpholin-4-yl-benzothiazol-2-yl)-amide and was obtained as yellow solid in 10% overall yield, MS: m/e=417 (M+H$^+$).

EXAMPLE 66

5-Methyl-thiophene-2-carboxylic acid (5-methoxy-7-phenyl-benzothiazol-2-yl)-amide 2-Amino-5-methoxy-7-phenylbenzothiazol (45 mg, 0.18 mmol) is dissolved in dichloromethane (2 ml) and subsequently treated with triethylamine (0.073 ml, 0.53 mmol) and 5-methyl-thiophene-2-carbonyl chloride (56 mg, 0.35 mmol). After 6 h, further 0.073 ml, 0.53 mmol) and 5-methyl-thiophene-2-carbonyl chloride (56 mg, 0.35 mmol) are added and the mixture is stirred for additional 18 h at ambient. After addition of 0.1M aqueous sodium hydroxide, the mixture is stirred for additional 16 h. The organic layer is separated, dried and evaporated to dryness. Flash chromatography (silica, eluent ethyl acetate/cyclohexane 1:1, containing 0.5% of 25% aqueous ammonia) affords (10 mg, 5%) of the product as white solid. MS: m/e=380 (M$^+$).

EXAMPLE 67

5-Methyl-thiophene-2-carboxylic acid (4,5-dimethoxy-benzothiazol-2-yl)-amide

2-Amino-4,5-dimethoxybanzothiazole (1.1 g, 5.3 mmol) and N,N.dimethylaminopyridine (47 mg, 0.37 mmol) are dissolved in pyridine (17 ml) and slowly treated with 5-methyl-thiophene-2-carbonyl chloride (1.5 g, 9.0 mmol). After 48 h at ambient temperature, the solution is evaporated to drynes. Flash chromatography (silica, eluent diethyl ether/cyclohexane 2:1) affords the product (618 mg, 35%) as light yellow solid.

EXAMPLE 68

5-Methyl-thiophene-2-carboxylic acid (4-chloro-benzothiazol-2-yl)-amide

2-Amino-4-chlorobenzothiazol (92 mg, 0.50 mmol) is dissolved in dichloromethane (10 ml) and treated with pyridine (0.060 ml, 0.75 mmol) and 5-methyl-thiophene-2-carbonyl chloride (97 mg, 0.60 mmol). The reaction mixture is stirred at ambient temperature for 18 h and then evaporated to dryness. The residue is redissolved in ethyl acetate and water, the phases are separated and the organic layer extracted with brine. After dryin with sodium silfate, the solvent is removed in vacuo Flash chromatography on silica (eluent ethyl acetate/cyclohexane 1:4 affords the product as white solid.(88 mg, 57%). MS: m/e=308 (M$^+$).

EXAMPLE 69

5-Methyl-thiophene-2-carboxylic acid (7-bromo-4-methoxy-benzothiazol-2-yl)-amide 2-Amino-7-bromo-4-methoxybenzothiazol (2.33 g, 9 mmol) is dissolved in dichloromethane (100 ml) and at 0° C. treated with pyridine (2.2 ml, 27 mmol) and 5-methyl-thiophene-2-carbonyl chloride (2.2 g, 13.5 mmol). The reaction mixture is allowed to warm to room temperature and after stirring for additional 18 h quenched with water (100 ml). After separation of the phases, the aqueous phases are extracted twice with ethyl acetate. The combined organic layers are then washed with brine, dried and avaporated to dryness. Flash chromatography on silica (eluent ethyl acetate/cyclohexane 1:1 to 4:1) and final recrystallization from ethyl acetate affords the product as off-white solid. (34 mg, 69%). MS: m/e=384 (M$^+$).

EXAMPLE 70

5-Methyl-thiophene-2-carboxylic acid (4-fluoro-benzothiazol-2-yl)-amide

2-Amino-4-flourobenzothiazol (84 mg, 0.50 mmol) is dissolved in pyridine (3 ml) and treated with 4-dimethylaminopyridine (1 mg) and 5-methyl-thiophene-2-carbonyl chloride (161 mg, 1.0 mmol). After stirring for 1 h at ambient temperature, the reaction mixture was evaporated to dryness. Flash chromatography on silica (eluent diethyl ether/cyclohexane 1:1 containing 0.5% of 25% aqueous ammonia) and final recrystallization from ethyl acetate affords the product as off-white solid.(34 mg, 69%). MS: m/e=292 (M$^+$).

EXAMPLE 71

5-Methyl-thiophene-2-carboxylic acid (4-trifluoromethoxy-benzothiazol-2-yl)-amide 2-amino-4-triflouromethoxybenzothiazol (70 mg, 0.30 mmol) is dissolved in pyridine (3 ml) and treated with 4-dimethylaminopyridine (1 mg) and 5-methyl-thiophene-2-carbonyl chloride (96 mg, 0.60 mmol). After stirring for 4 h at ambient temperature, the reaction mixture was evaporated to dryness. Flash chromatography on silica (eluent ethyl acetate/cyclohexane 1:2) affords the product as white solid. (42 mg, 39% yield). MS: m/e=358 (M+).
Following the General Method of Example 1, the Compounds of Examples 72 to 75 were Prepared

EXAMPLE 72

5-Methyl-thiophene-2-carboxylic acid (4-methoxy-7-morpholin-4-yl-benzothiazol-2-yl)-amide Using 5-methyl-thiophene-2-carbonyl chloride and 2-amino-4-methoxy-7-morpholin-4-yl-benzothiazol the title compound was obtained as a yellow solid in 97% yield. MS: m/e=390 (M+H+).

EXAMPLE 73

6-Hydroxy-pyridine-2-carboxylic acid (4-methoxy-benzothiazol-2-yl)-amide

Using 2-Amino-4-methoxybenzothiazole (450 mg, 2.5 mmol) and 6-hydroxypicolinic acid chloride (1.5 g, 10 mmol) the title compound was obtained as a beige powder in 5% yield. MS: m/e=301 (M+).

EXAMPLE 74

5-Methyl-thiophene-2-carboxylic acid (7-benzyloxy-4-methoxy-benzothiazol-2-yl)-amide Using 5-methyl-thiophene-2-carboxylic acid chloride the title compound was obtained as an off-white solid (51% yield). M.p.: 228–230° C.
Following the General Method of Example 1, the Compound of Example 75 was Prepared

EXAMPLE 75

6-Chloro-N-(4-methoxy-7-phenyl-benzothiazol-2-yl)-nicotinamide

Using 6-chloro-nicotinyl chloride the title compound was obtained as a light yellow amorphous solid (79% yield), MS: m/e=395.1 (M+).

EXAMPLE 76

N-(4-Methoxy-7-phenyl-benzothiazol-2-yl)-6-pyrrolidin-1-yl-nicotinamide

To a solution of 6-chloro-N-(4-methoxy-7-phenyl-benzothiazol-2-yl)-nicotinamide (297 mg, 0.75 mmol) in dioxane (10 ml) was added pyrrolidine (266 mg, 3.7 mmol, 5 eq.) and the mixture stirred at 100° C. for 2 h. After cooling the solvent was evaporated and the residue suspended in methanol (20 ml) at r.t., the solid was then filtered, washed with methanol and finally dried under vacuum (0.05 mmHg, 60° C.) to obtain the title compound as a white solid (230 mg, 71% yield), MS: m/e=431.4 (M+H+).
Following the General Method of Example 76, the Compounds of Examples 77 to 80 were Prepared

EXAMPLE 77

3,4,5,6-Tetrahydro-2H-[1,2']bipyridinyl-5'-carboxylic acid (4-methoxy-7-phenyl-benzothiazol-2-yl)-amide Using piperidine the title compound was obtained as a light brown solid (59% yield), MS: m/e=445.3 (M+H+).

EXAMPLE 78

N-(4-Methoxy-7-phenyl-benzothiazol-2-yl)-6-morpholin-4-yl-nicotinamide

Using morpholine the title compound was obtained as a white solid (82% yield), MS: m/e=447.2 (M+H+).

EXAMPLE 79

N-(4-Methoxy-7-phenyl-benzothiazol-2-yl)-6-(4-methyl-piperazin-1-yl)-nicotinamide Using N-methylpiperazine the title compound was obtained as a light brown solid (52% yield), MS: m/e=460.4 (M+H+).

EXAMPLE 80

N-(4-Methoxy-7-phenyl-benzothiazol-2-yl)-6-thiomorpholin-4-yl-nicotinamide hydrochloride salt (1:1)

Using thiomorpholine the free base of the title compound was obtained, which was then conveted to the hydrochloride salt by addition of 5N HCl/EtOH, affording the title compound as a white solid (78% yield), MS: m/e=463.1 (M+H+).

EXAMPLE 81

N-(4-Methoxy-7-phenyl-benzothiazol-2-yl)-6-(1-oxo-11 4-thiomorpholin-4-yl)-nicotinamide hydrochloride salt (1:1)

To a solution of N-(4-methoxy-7-phenyl-benzothiazol-2-yl)-6-thiomorpholin-4-yl-nicotinamide hydrochloride salt (250 mg, 0.54 mmol) in chloroform (12 ml) was added 3-phenyl-2-(phenylsulfonyl)oxaziridine (211 mg, 0.81 mmol) and the mixture stirred at r.t. for 2 hr. After evaporation of the solvent, the residue was suspended in $CH_2Cl_2$, ultrasonnicated, then the precipitate was filtered off, washed with $CH_2Cl_2$, followed by ether and finally dried under vacuum (0.05 mmHg, 60° C.) to obtain the title compound as a light yellow solid (240 mg., 86% yield), MS: m/e=479.2 (M+H+).

EXAMPLE 82

4-Bromomethyl-N-(4-methoxy-7-phenyl-benzothiazol-2-yl)-benzamide

To a solution of 4-bromomethyl-benzoic acid (5.45 g, 25.3 mmol) in toluene (60 ml) was added thionyl chloride (18.25 ml, 25.3 mmol) and the mixture stirred at 80° C. for 16 h. The toluene and excess thionyl chloirde were then evaporated in vacuo and replaced with THF (100 ml). To this solution was added 2-amino-4-methoxy-7-phenyl-benzothiazole (5 g, 19.5 mmol), triethylamine (4.1 ml, 29.2 mmol) and DMAP (238 mg, 2 mmol) as catalyst, then the mixture stirred at 65° C. for 4 h. After cooling the reaction mixture was partitioned between 10% aq. $Na_2CO_3$ (200 ml) and EtOAc (100 ml), the aqueous phase was extracte further with EtOAc/THF (1:1) (150 ml), then the combined organic phases were washed with satd. aq. NaCl (100 ml), dried ($Na_2SO_4$), filtered and evaporated in vacuo. The residue was then chromatographed over $SiO_2$ (Merck 230–400 mesh) eluting with a gradient of $CH_2Cl_2$/EtOAc (100% $CH_2Cl_2$ to 1:1), the product fractions were pooled and evaporated in vacuo to affords the title compound as a pale yellow solid (4.9 g, 55% yield), MS: m/e=452.0 (M+).

EXAMPLE 83

N-(4-Methoxy-7-phenyl-benzothiazol-2-yl)-4-pyrrolidin-1-ylmethyl-benzamide hydrochloride salt (1:1)

To a solution of 4-formyl-N-(4-methoxy-7-phenyl-benzothiazol-2-yl)-benzamide (300 mg, 0.77 mmol) in THF (60 ml) was added pyrrolidine (82 mg, 1.16 mmol), acetic acid (70 mg, 1.16 mmol) and NaBH(OAc)$_3$ (246 mg, 1.16 mmol). This mixture was stirred for 16 h at r.t., then 5% NaHCO$_3$ (30 ml) was added with vigorous stirring and the mixture extracted twice with EtOAc (50 ml). The organic phases were washed with saturates NaCl solution then dried, filtered and evaporated to afford the crude product which was converted to its hydrochloride salt and purified by reversed phase preparative HPLC using a Nucleosil (Machery-Nagel) N-protected column (20×50 mm) and an MeCN/water (0.1% TFA) gradient. After pooling and evaporation of the product fractions the title compound was obtained as a white solid (217 mg, 59% yield), MS: m/e=444.4 (M+H$^+$).

Following the General Method of Example 83, the Compounds of Examples 84 to 89 were Prepared

EXAMPLE 84

N-(4-Methoxy-7-phenyl-benzothiazol-2-yl)-4-piperidin-1-ylmethyl-benzamide hydrochloride salt (1:1)

Using piperidine the title compound was obtained as a light yellow solid (78% yield), MS: m/e=458.4 (M+H$^+$).

EXAMPLE 85

N-(4-Methoxy-7-phenyl-benzothiazol-2-yl)-4-morpholin-4-ylmethyl-benzamide hydrochloride salt (1:1)

Using morpholine the title compound was obtained as a light yellow solid (23% yield), MS: m/e=460.5 (M+H$^+$).

EXAMPLE 86

4-Diethylaminomethyl-N-(4-methoxy-7-phenyl-benzothiazol-2-yl)-benzamide hydrochloride (1:1)

Using diethylamine the title compound was obtained as a white solid (39% yield), MS: m/e=446.3 (M+H$^+$).

EXAMPLE 87

N-(4-Methoxy-7-phenyl-benzothiazol-2-yl)-4-[(methyl-pyridin-3-ylmethyl-amino)-methyl]-benzamide hydrochloride salt (1:2)

Using 3-(methylaminomethyl)-pyridine the title compound was obtained as a light yellow solid (15% yield), MS: m/e=495.2 (M+H$^+$).

EXAMPLE 88

N-(4-Methoxy-7-phenyl-benzothiazol-2-yl)-4-(4-methyl-piperazin-1-ylmethyl)-benzamide hydrochloride salt (1:2)

Using N-methyl-piperazine the title compound was obtained as a white solid (21% yield), MS: m/e=473.3 (M+H$^+$).

EXAMPLE 89

4-Dimethylaminomethyl-N-(4-methoxy-7-phenyl-benzothiazol-2-yl)-benzamide hydrochloride salt (1:1)

Using dimethylamine hydrochloride the title compound was obtained as a light yellow solid (21% yield), MS: m/e=418.3 (M+H$^+$).

EXAMPLE 90

4-Ethylaminomethyl-N-(4-methoxy-7-phenyl-benzothiazol-2-yl)-benzamide hydrochloride salt (1:1)

To a solution of 4-bromomethyl-N-(4-methoxy-7-phenyl-benzothiazol-2-yl)-benzamide (300 mg, 0.66 mmol) in THF (2 ml) was added ethylamine (2N in THF) (3 ml, 6.6 mmol) and the mixture stirred at 20° C. for 18 h. The reaction mixture was then evaporated to dryness and the residue treated with an excess of 5N HCl/EtOH (3 ml), the ethanol was then evporated and the residue dissolved in DMSO and then subjected to preparative reversed phase HPLC purification using a C18 ODS-AQ column (20×50 mm), eluting with a gradient of MeCN/water (0.1% TFA). The product fractions were pooled and evaporated to afford the title compound as a light yellow solid (238 mg, 79% yield), MS: m/e=418.3 (M+H$^+$).

Following the General Method of Example 90, the Compounds of Examples 91 to 126 were Prepared

EXAMPLE 91

4-[(2-Methoxy-ethylamino)-methyl]-N-(4-methoxy-7-phenyl-benzothiazol-2-yl)-benzamide hydrochloride salt (1:1)

Using 2-methoxyethylamine in dioxane at 90° C. the title compound was obtained as a light yellow solid (66% yield), MS: m/e=448.3 (M+H$^+$).

EXAMPLE 92

4-[(2-Hydroxy-ethylamino)-methyl]-N-(4-methoxy-7-phenyl-benzothiazol-2-yl)-benzamide hydrochloride salt (1:1)

Using ethanolamine in dioxane at 90° C. the title compound was obtained as a light yellow solid (68% yield), MS: m/e=434.4 (M+H$^+$).

EXAMPLE 93

4-(Benzylamino-methyl)-N-(4-methoxy-7-phenyl-benzothiazol-2-yl)-benzamide hydrochloride salt (1:1)

Using benzylamine in dioxane at 90° C. the title compound was obtained as a white solid (50% yield), MS: m/e=480.3 (M+H$^+$).

EXAMPLE 94

4-[(Benzyl-methyl-amino)-methyl]-N-(4-methoxy-7-phenyl-benzothiazol-2-yl)-benzamide hydrochloride salt (1:1)

Using N-methyl-benzylamine in dioxane at 90° C. the title compound was obtained as a white solid (74% yield), MS: m/e=494.3 (M+H$^+$).

EXAMPLE 95

4-[(3-Imidazol-1-yl-propylamino)-methyl]-N-(4-methoxy-7-phenyl-benzothiazol-2-yl)-benzamide hydrochloride salt (1:2)

Using 1-(3-aminopropyl)-imidazole in dioxane at 90° C. the title compound was obtained as a pale yellow solid (58% yield), MS: m/e=498.2 (M+H$^+$).

EXAMPLE 96

N-(4-Methoxy-7-phenyl-benzothiazol-2-yl)-4-{[(pyridin-4-ylmethyl)-amino]-methyl}-benzamide hydrochloride salt (1:2)

Using 4-(aminomethyl)-pyridine in dioxane at 90° C. the title compound was obtained as a beige solid (33% yield), MS: m/e=481.2 (M+H$^+$).

EXAMPLE 97

4-{[(2-Methoxy-ethyl)-methyl-amino]-methyl}-N-(4-methoxy-7-phenyl-benzothiazol-2-yl)-benzamide hydrochloride salt (1:1)

Using N-(2-methoxyethyl)-methylamine in dioxane at 90° C. the title compound was obtained as a light yellow solid (73% yield), MS: m/e=462.3 (M+H$^+$).

EXAMPLE 98

4-(1,1-Dioxo-4-thiomorpholin-4-ylmethyl)-N-(4-methoxy-7-phenyl-benzothiazol-2-yl)-benzamide hydrochlorde salt (1:1)

To a solution of N-(4-methoxy-7-phenyl-benzothiazol-2-yl)-4-thiomorpholin-4-ylmethyl-benzamide (350 mg, 0.73 mmol) in CH$_2$Cl$_2$ (10 ml) was added 3-phenyl-2-(phenylsulfonyl) oxaziridine (288 mg, 1.1 mmol) and the mixture stirred for 2 h at r.t. The reaction mixture was then evaporated to drynesss, the residue suspended in ether, and the solid filtered off and washed with ether followed by acetone. This solid was dissolved in methanol (10 ml) and treated with 5N HCl/MeOH for 1 h at r.t., the resulting precipitate was filtered off, washed with methanol and finally dried under vacuum (0.05 mmHg, 60° C.) to afford the title compound as a white solid (270 mg, 68% yield), MS: m/e=508.3 (M+H$^+$).

EXAMPLE 99

N-(4-Methoxy-7-phenyl-benzothiazol-2-yl)-4-thiomorpholin-4-ylmethyl-benzamide hydrochloride salt (1:1)

Using thiomorpholine in dioxane at 90° C. the title compound was obtained as a yellow solid (68% yield), MS: m/e=476.1 (M+H$^+$).

EXAMPLE 100

4-Imidazol-1-ylmethyl-N-(4-methoxy-7-phenyl-benzothiazol-2-yl)-benzamide hydrochloride salt (1:1)

Using imidazole in DMF at 90° C. the title compound was obtained as a pale yellow solid (92% yield), MS: m/e=441.3 (M+H$^+$).

EXAMPLE 101

4-(2-Hydroxymethyl-imidazol-1-ylmethyl)-N-(4-methoxy-7-phenyl-benzothiazol-2-yl)-benzamide Using 2-hydroxymethyl-imidazole in DMF at 90° C. the title compound was obtained as a pale yellow solid (16% yield), MS: m/e=471.1 (M+H$^+$).

EXAMPLE 102

N-(4-Methoxy-7-phenyl-benzothiazol-2-yl)-4-(2-methylimidazol-1-ylmethyl)-benzamide Using 2-methyl-imidazole in DMF at 90° C. the title compound was obtained as a white solid (79% yield), MS: m/e=455.5 (M+H$^+$).

EXAMPLE 103

4-(4,5-Dimethyl-imidazol-1-ylmethyl)-N-(4-methoxy-7-phenyl-benzothiazol-2-yl)-benzamide Using 4,5-dimethyl-imidazole in DMF at 90° C. the title compound was obtained as a pale yellow solid (67% yield), MS: m/e=469.2 (M+H$^+$).

EXAMPLE 104

N-(4-Methoxy-7-phenyl-benzothiazol-2-yl)-4-piperazin-1-ylmethyl-benzamide hydrochloride salt (1:2)

Using 1-tert-butoxycarbonyl-piperazine in dioxane at 90° C. the title compound was obtained as a pale yellow solid (80% yield), MS: m/e=459.5 (M+H$^+$).

EXAMPLE 105

4-Allylaminomethyl-N-(4-methoxy-7-phenyl-benzothiazol-2-yl)-benzamide hydrochloride salt (1:1)

Using allylamine in dioxane at 90° C. the title compound was obtained as a pale yellow solid (65% yield), MS: m/e=430.5 (M+H$^+$).

EXAMPLE 106

N-(4-Methoxy-7-phenyl-benzothiazol-2-yl)-4-propylaminomethyl-benzamide hydrochloride salt (1:1)

Using propylamine in dioxane at 90° C. the title compound was obtained as a pale yellow solid (63% yield), MS: m/e=432.4 (M+H$^+$).

EXAMPLE 107

N-(4-Methoxy-7-phenyl-benzothiazol-2-yl)-4-{[(pyridin-3-ylmethyl)-amino]-methyl}-benzamide hydrochloride salt (1:2)

Using 3-(aminomethyl)-pyridine in THF at 65° C. the title compound was obtained as a pale yellow solid (28% yield), MS: m/e=481.3 (M+H$^+$).

EXAMPLE 108

4-(4-Hydroxy-piperidin-1-ylmethyl)-N-(4-methoxy-7-phenyl-benzothiazol-2-yl)-benzamide hydrochloride salt (1:1)

Using 4-hydroxy-piperidine in THF at 65° C. the title compound was obtained as a white solid (61% yield), MS: m/e=474.3 (M+H$^+$).

EXAMPLE 109

4-(3(S)-Hydroxy-pyrrolidin-1-ylmethyl)-N-(4-methoxy-7-phenyl-benzothiazol-2-yl)-benzamide hydrochloride salt (1:1)

Using (S)-3-hydroxy-pyrrolidine in THF at 65° C. the title compound was obtained as a white solid (74% yield), MS: m/e=460.3 (M+H$^+$).

EXAMPLE 110

4-[1,4]Diazepan-1-ylmethyl-N-(4-methoxy-7-phenyl-benzothiazol-2-yl)-benzamide hydrochloride salt (1:2)

Using tert-butyl-1-homopiperazine carboxylate in THF at 65° C. the title compound was obtained as a light yellow solid (87% yield), MS: m/e=473.2 (M+H$^+$).

EXAMPLE 111

4-(3(R)-Dimethylamino-pyrrolidin-1-ylmethyl)-N-(4-methoxy-7-phenyl-benzothiazol-2-yl)-benzamide hydrochloride salt (1:2)

Using (3R)-(+)-3-dimethylamino-pyrolidine in THF at 65° C. the title compound was obtained as a light brown solid (51% yield), MS: m/e=487.3 (M+H$^+$).

EXAMPLE 112

N-(4-Methoxy-7-phenyl-benzothiazol-2-yl)-4-[(2-morpholin-4-yl-ethylamino)-methyl]-benzamide hydrochloride salt (1:2)

Using 4-(2-aminoethyl)-morpholine in THF at 65° C. the title compound was obtained as a light yellow solid (44% yield), MS: m/e=503.3 (M+H$^+$).

EXAMPLE 113

N-(4-Methoxy-7-phenyl-benzothiazol-2-yl)-4-[(2-pyrrolidin-1-yl-ethylamino)-methyl]-benzamide hydrochloride salt (1:2)

Using N-(2-aminoethyl)-pyrrolidine in THF at 65° C. the title compound was obtained as a light yellow solid (37% yield), MS: m/e=487.3 (M+H$^+$).

EXAMPLE 114

N-(4-Methoxy-7-phenyl-benzothiazol-2-yl)-4-[(2-piperidin-1-yl-ethylamino)-methyl]-benzamide hydrochloride salt (1:2)

Using N-(2-aminoethyl)-piperidinee in THF at 65° C. the title compound was obtained as a light yellow solid (50% yield), MS: m/e=501.3 (M+H$^+$).

EXAMPLE 115

4-Cyclobutylaminomethyl-N-(4-methoxy-7-phenyl-benzothiazol-2-yl)-benzamide hydrochloride salt (1:1)

Using cyclobutylamine in THF at 65° C. the title compound was obtained as a white solid (68% yield), MS: m/e=444.3 (M+H$^+$).

EXAMPLE 116

4-Cyclopentylaminomethyl-N-(4-methoxy-7-phenyl-benzothiazol-2-yl)-benzamide hydrochloride salt (1:1)

Using cyclopentylamine in THF at 65° C. the title compound was obtained as a light brown solid (46% yield), MS: m/e=458.4 (M+H$^+$).

EXAMPLE 117

4-{[(Furan-2-ylmethyl)-amino]-methyl}-N-(4-methoxy-7-phenyl-benzothiazol-2-yl)-benzamide hydrochloride salt (1:1)

Using 2-(aminomethyl)-furan in THF at 65° C. the title compound was obtained as a beige solid (57% yield), MS: m/e=470.2 (M+H$^+$).

EXAMPLE 118

N-(4-Methoxy-7-phenyl-benzothiazol-2-yl)-4-{[(thiophen-2-ylmethyl)-amino]-methyl}-benzamide hydrochloride salt (1:1)

Using 2-(aminomethyl)-thiophene in THF at 65° C. the title compound was obtained as a light yellow solid (60% yield), MS: m/e=486.3 (M+H$^+$).

EXAMPLE 119

4-Dipropylaminomethyl-N-(4-methoxy-7-phenyl-benzothiazol-2-yl)-benzamide hydrochloride salt (1:1)

Using dipropylamine in THF at 65° C. the title compound was obtained as a white solid (64% yield), MS: m/e=474.3 (M+H$^+$).

EXAMPLE 120

N-(4-Methoxy-7-phenyl-benzothiazol-2-yl)-4-{[methyl-(2-pyridin-2-yl-ethyl)-amino]-methyl}-benzamide hydrochloride salt (1:2)

Using 2-[(2-(methylamino)ethyl]-pyridine in THF at 65° C. the title compound was obtained as a beige solid (46% yield), MS: m/e=509.3 (M+H$^+$).

EXAMPLE 121

4-Aminomethyl-N-(4-methoxy-7-phenyl-benzothiazol-2-yl)-benzamide hydrochloride salt (1:1)

Using ammonia (7N in MeOH) in THF at 20° C. the title compound was obtained (after 4 days) as a white solid (34% yield), MS: m/e=389.1 (M$^+$).

EXAMPLE 122

4-[(Cyclopropylmethyl-amino)-methyl]-N-(4-methoxy-7-phenyl-benzothiazol-2-yl)-benzamide hydrochloride salt (1:1)

Using aminomethyl-cyclopropane in dioxane at 90° C. the title compound was obtained as a light yellow solid (69% yield), MS: m/e=444.3 (M+H$^+$).

EXAMPLE 123

N-(4-Methoxy-7-phenyl-benzothiazol-2-yl)-4-[(2-methylsulfanyl-ethylamino)-methyl]-benzamide hydrochlorde salt (1:2)

Using 2-(methylthio)-ethylamine in THF at 65° C. the title compound was obtained as a light yellow solid (74% yield), MS: m/e=464.2 (M+H$^+$).

EXAMPLE 124

N-(4-Methoxy-7-phenyl-benzothiazol-2-yl)-4-thiazolidin-3-ylmethyl-benzamide hydrochlorde salt (1:1)

Using thiazolidine in THF at 65° C. the title compound was obtained as a white solid (48% yield), MS: m/e=462.2 (M+H$^+$).

EXAMPLE 125

4-(3(S)-Dimethylamino-pyrrolidin-1-ylmethyl)-N-(4-methoxy-7-phenyl-benzothiazol-2-yl)-benzamide hydrochlorde salt (1:2)

Using (3S)-(−)-3-(dimethylamino)-pyrrolidine in THF at 65° C. the title compound was obtained as a light brown solid (56% yield), MS: m/e=487.3 (M+H$^+$).

EXAMPLE 126

4-[(2-Dimethylamino-ethylamino)-methyl]-N-(4-methoxy-7-phenyl-benzothiazol-2-yl)-benzamide hydrochloride salt (1:2)

Using 2-(dimethylamino)-ethylamine in THF at 65° C. the title compound was obtained as a light yellow solid (32% yield), MS: m/e=461.3 (M+H$^+$).

Preparation of the 4-(R¹R²-amino)-N-(4-methoxy-7-aryl-benzothiazol-2-yl)-benzamides:

General procedure C: The appropriate 2-amino-7-aryl-4-methoxy-benzothiazol is converted with 4-(chloromethyl) benzoyl chloride using the general method of example 1. The product is then converted neat with the appropriate amine (10 equivalents) at 100° C. for 24 hours. The reaction mixture is then dissolved in ethyl acetate, extracted with water and brine, dried and evaporated in vacuo. Flash chromatography (silica, eluent dichloromethane containing 1.2 to 2.4% methanol) affords the product in about 50% yield.

EXAMPLE 127

4-Cloromethyl-N-(4-methoxy-7-morpholin-4-yl-benzothiazol-2-yl)-benzamide and 2-amino-4-methoxy-7-morpholin-4-yl-benzothiazol (1.0 g, 3.8 mmol), 4-(chloromethyl) benzoyl chloride (810 mg, 4.2 mmol) and pyridine (0.36 ml, 4.5 mmol) are reacted in dichloromethane (20 ml) for 18 h. The reaction is quenched with water (25 ml) and brought to pH 8.0 with sodium carbonate. The mixture is extracted with dichloromethane and the combined organic layers are dried and evapoarted to dryness. Flash chromatography (silica, eluent methylene chloride containing 2.5% methanol) affords the product as white crystalls in 54% yield. MS: m/e=418 (M+H$^+$).

Following the General Method the Compounds of Examples 128 to 132 were Prepared

EXAMPLE 128

4-(4-Hydroxy-piperidin-1-yl methyl)-N-(4-methoxy-7-morpholin-4-yl-benzothiazol-2-yl)-benzamide Conversion of 4-cloromethyl-N-(4-methoxy-7-morpholin-4-yl-benzothiazol-2-yl)-benzamide (84 mg, 0.20 mmol) with 4-hydroxypiperazin (200 mg, 2.0 mmol) using the general procedure C affords the product as white solid in 73% yield. MS: m/e=483 (M+H$^+$)

EXAMPLE 129

4-{[(2-Methoxy-ethyl)-methyl-amino]-methyl}-N-(4-methoxy-7-morpholin-4-yl-benzothiazol-2-yl)-benzamide Conversion of 4-cloromethyl-N-(4-methoxy-7-morpholin-4-yl-benzothiazol-2-yl)-benzamide (84 mg, 0.20 mmol) with N-(2-methoxyethyl)-methylamin (178 mg, 2.0 mmol) using the general procedure C affords the product as white solid in 55% yield. MS: m/e=471 (M+H$^+$).

EXAMPLE 130

4-{[(2-Hydroxy-ethyl)-methyl-amino]-methyl}-N-(4-methoxy-7-morpholin-4-yl-benzothiazol-2-yl)-benzamide 3,4-Dimethoxy-benzoic acid 2-{[4-(4-methoxy-7-morpholin-4-yl-benzothiazol-2-yl carbamoyl)-benzyl]-methyl-amino}-ethyl ester (63 mg, 0.10 mmol) are heated in aqueous sodium hydroxide (1M, 0.5 ml) and ethanol (2 ml) to 100° C. for 30 min. The mixture is diluted with water and extracted twice with ethyl acetate. The combined organic layers are extracted with saturated aqueous sodium hydrogencarbonate, dried and evaporated to dryness. Flash chromatography (silica, eluent methylene chloride containing 5% methanol) affords the product as white crystals in 48% yield. MS: m/e=457 (M+H$^+$).

EXAMPLE 131

3,4-Dimethoxy-benzoic acid 2-{[4-(4-methoxy-7-morpholin-4-yl-benzothiazol-2-ylcarbamoyl)-benzyl]-methyl-amino}-ethyl ester Conversion of 4-cloromethyl-N-(4-methoxy-7-morpholin-4-yl-benzothiazol-2-yl)-benzamide (84 mg, 0.20 mmol) with 3,4-dimethoxybenzoic acid 2-methylamino-ethyl ester chlorohydrate (96 mg, 0.4 mmol) and N-ethyl diisopropylamine (0.14 ml, 0.80 mmol) using the general procedure C affords the product as light yellow solid in 57% yield. MS: m/e=621 (M+H$^+$).

EXAMPLE 132

N-(4-Methoxy-7-morpholin-4-yl-benzothiazol-2-yl)-4-piperazin-1-ylmethyl-benzamide Conversion of 4-cloromethyl-N-(4-methoxy-7-morpholin-4-yl-benzothiazol-2-yl)-benzamide (84 mg, 0.20 mmol) with 1-BOC-piperazine (372 mg, 1.9 mmol) using the general procedure C and afterwards cleavage of the neat carbamate in trifluoroacetic acid (1 ml) followed by saturated aqueous sodium carbonate affords the product as colorless crystals in 72% yield. MS: m/e=468 (M+H$^+$).

EXAMPLE 133

N-(7-Benzyloxy-4-methoxy-benzothiazol-2-yl)-4-chloromethyl-benzamide

Following the general method of example 1 the title compound was obtained as a light yellow solid (70% yield). MS (EI): me/e=438 (M$^+$).

EXAMPLE 134

N-(7-Benzyloxy-4-methoxy-benzothiazol-2-yl)-4-(3-dimethylamino-pyrrolidin-1-ylmethyl)-benzamide hydrochloride According to general procedure C the title compound was obtained as a light brown solid (86% yield). M.p.: 195° C. (dec.).

Preparation of the 3-(7-aryl-4-methoxy-benzothiazol-2-yl)-1-R³-1-R⁴-ureas

General procedure D: The appropriate 2-amino-7-aryl-4-methoxy-benzothiazol (1 part) and pyridine (1.2 equivalents) are dissolved in 40 parts tetrahydrofuran and treated with phosgene (20% in toluene, 1 equivalent) at ambient temperature. After 60 min, the reaction mixture is concentrated to half the volume under reduced pressure and the appropriate amine (1.25 equivalents) and pyridine (1.1 equivalents) are added. After 15 min at ambient temperature, the reaction mixture is evaporated to dryness. The product is isolated by flash chromatography (silica, eluent dichloromethane containing 2.5% methanol).

Following the General Method the Compounds of Examples 135 to 137 were Prepared

EXAMPLE 135

Thiomorpholine-4-carboxylic acid (4-methoxy-7-morpholin-4-yl-benzothiazol-2-yl)-amide Conversion of 2-amino-4-methoxy-7-morpholin-4-yl-benzothiazol (100 mg, 0.377 mg) with phosgene (20% in toluene, 0.2 ml) and thiomorpholine (0.045 ml, 0.47 mmol) using the general procedure D affords the product as white solid in 73% yield. MS: m/e=395 (M+H$^+$).

EXAMPLE 136

Morpholine-4-carboxylic acid (4-methoxy-7-morpholin-4-yl-benzothiazol-2-yl)-amide Conversion of 2-amino-4-methoxy-7-morpholin-4-yl-benzothiazol (100 mg, 0.377 mg) with phosgene (20% in toluene, 0.2 ml) and morpholine (0.041 ml, 0.47 mmol) using the general procedure D affords the product as white solid in 25% yield. MS: m/e=379 (M+H$^+$).

EXAMPLE 137

3-(4-Methoxy-7-morpholin-4-yl-benzothiazol-2-yl)-1-methyl-1-(6-methyl-pyridin-3-ylmethyl)-urea Conversion of 2-amino-4-methoxy-7-morpholin-4-yl-benzothiazol (100 mg, 0.377 mg) with phosgene (20% in toluene, 0.2 ml) and methyl-(6-methyl-pyridin-3-ylmethyl)-amine (0.064 ml, 0.47 mmol) using the general procedure D affords the product as white solid in 25% yield. MS: m/e=429 (M+H$^+$).

EXAMPLE 138

1-Furan-2-yl-methyl-3-(4-methoxy-benzothiazol-2-yl)-urea

To a solution of (4-Methoxy-benzothiazol-2-yl)-carbamic acid tert-butyl ester (80 mg, 0.29 mmol) in dioxane (2 ml) was addded furfurylamine (55 mg, 0.57 mmol) and the mixture heated to 100° C. for 20 h. The reaction mixture was then evaporated to dryness and the residue recrystallised from ether/nHexane to afford the title compound as a beige solid (80 mg, 92% yield), MS: m/e=303 (M$^+$).

Following the General Method of Example 138, the Compounds of Examples 139 to 163 were Prepared

EXAMPLE 139

1-Furan-2-yl-methyl-3-(4-methoxy-7-phenyl-benzothiazol-2-yl)-urea

Using (4-Methoxy-benzothiazol-2-yl)-carbamic acid tert-butyl ester and furfurylamine the title compound was obtained as a beige solid (66% yield), MS: m/e=380.3 (M+H$^+$).

EXAMPLE 140

1-(4-Methoxy-7-phenyl-benzothiazol-2-yl)-3-thiophen-2-yl-methyl-urea

Using (4-methoxy-7-phenyl-benzoyhiazol-2-yl)-carbamic acid tert-butyl ester and thiophene-2-methylamine the title compound was obtained as a beige solid (62% yield), MS: m/e=396.3 (M+H$^+$).

EXAMPLE 141

1-(4-Methoxy-7-phenyl-benzothiazol-2-yl)-3-pyridin-2-yl-methyl-urea

Using (4-methoxy-7-phenyl-benzoyhiazol-2-yl)-carbamic acid tert-butyl ester and 2-(aminomethyl)-pyridine the title compound was obtained as a beige solid (18% yield) following purification using reversed-phase preparative HPLC, C18 ODS-AQ, with an MeCN/water gradient, MS: m/e=391.2 (M+H$^+$).

EXAMPLE 142

1-(4-Methoxy-7-phenyl-benzothiazol-2-yl)-3-pyridin-3-ylmethyl-urea

Using (4-methoxy-7-phenyl-benzoyhiazol-2-yl)-carbamic acid tert-butyl ester and 3-(aminomethyl)-pyridine the title compound was obtained as a beige solid (18% yield) following purification using reversed-phase preparative HPLC, C18 ODS-AQ, with a water/acetonitrile gradient, MS: m/e=391.2 (M+H$^+$).

EXAMPLE 143

1-(4-Methoxy-7-phenyl-benzothiazol-2-yl)-3-pyridin-4-ylmethyl-urea

Using (4-methoxy-7-phenyl-benzoyhiazol-2-yl)-carbamic acid tert-butyl ester and 4-(aminomethyl)-pyridine the title compound was obtained as a beige solid (52% yield), MS: m/e=391.2 (M+H$^+$).

EXAMPLE 144

3-(4-Methoxy-7-phenyl-benzothiazol-2-yl)-1-methyl-1-pyridin-3-yl-methyl-urea

Using (4-methoxy-7-phenyl-benzoyhiazol-2-yl)-carbamic acid tert-butyl ester and 3-(methylaminomethyl)-pyridine the title compound was obtained as a beige solid (23% yield), MS: m/e=405.4 (M+H$^+$).

EXAMPLE 145

1-(4-Methoxy-7-phenyl-benzothiazol-2-yl)-3-phenethyl-urea

Using (4-methoxy-7-phenyl-benzoyhiazol-2-yl)-carbamic acid tert-butyl ester and phenethylamine the title compound was obtained as a beige solid (77% yield), MS: m/e=404.5 (M+H$^+$).

EXAMPLE 146

1-(4-Methoxy-7-phenyl-benzothiazol-2-yl)-3-(3-phenyl-propyl)-urea

Using (4-methoxy-7-phenyl-benzoyhiazol-2-yl)-carbamic acid tert-butyl ester and 3-phenyl-propylamine the title compound was obtained as a beige solid (71% yield), MS: m/e=417.5 (M+H$^+$).

EXAMPLE 147

1-(4-Methoxy-benzyl)-3-(4-methoxy-7-phenyl-benzothiazol-2-yl)-urea

Using (4-methoxy-7-phenyl-benzoyhiazol-2-yl)-carbamic acid tert-butyl ester and 4-methoxy-benzylamine the title compound was obtained as a beige solid (60% yield), MS: m/e=420.3 (M+H$^+$).

EXAMPLE 148

3,4-Dihydro-1H-isoquinoline-2-carboxylic acid (4-methoxy-7-phenyl-benzothiazol-2-yl)-amide Using (4-methoxy-7-phenyl-benzoyhiazol-2-yl)-carbamic acid tert-butyl ester and 1,2,3,4- tetrahydroisoquinoline the title compound was obtained as a beige solid (31% yield) following purification using reverse-phase prep. HPLC, C18 ODS-AQ, with a water/acetonitrile gradient, MS: m/e=416.3 (M+H$^+$).

EXAMPLE 149

1-(2-Dimethylamino-ethyl)-3-(4-methoxy-7-phenyl-benzothiazol-2-yl)-urea

Using (4-methoxy-7-phenyl-benzoyhiazol-2-yl)-carbamic acid tert-butyl ester and 2-dimethylamino-ethylamine the title compound was obtained as a beige solid (67% yield), MS: m/e=371.3 (M+H$^+$).

EXAMPLE 150

1-(2-Hydroxy-ethyl)-3-(4-methoxy-7-phenyl-benzothiazol-2-yl)-urea

Using (4-methoxy-7-phenyl-benzoyhiazol-2-yl)-carbamic acid tert-butyl ester and ethanolamine the title compound was obtained as a beige solid (35% yield), MS: m/e=344.3 (M+H$^+$).

EXAMPLE 151

1-(4-Methoxy-7-phenyl-benzothiazol-2-yl)-3-(2-piperidin-1-yl-ethyl)-urea

Using (4-methoxy-7-phenyl-benzoyhiazol-2-yl)-carbamic acid tert-butyl ester and 1-(2-aminoethyl)-piperidine the title compound was obtained as a beige solid (67% yield), MS: m/e=411.4 (M+H$^+$).

EXAMPLE 152

1-(4-Methoxy-7-phenyl-benzothiazol-2-yl)-3-(2-morpholin-4-yl-ethyl)-urea

Using (4-methoxy-7-phenyl-benzoyhiazol-2-yl)-carbamic acid tert-butyl ester and 4-(2-aminoethyl)-morpholine the title compound was obtained as a beige solid (29% yield), MS: m/e=413.4 (M+H$^+$).

EXAMPLE 153

1-(4-Methoxy-7-phenyl-benzothiazol-2-yl)-3-(2-pyridin-2-yl-ethyl)-urea

Using (4-methoxy-7-phenyl-benzoyhiazol-2-yl)-carbamic acid tert-butyl ester and 2-(2-aminoethyl)-pyridine the title compound was obtained as a beige solid (88% yield), MS: m/e=405.4 (M+H$^+$).

EXAMPLE 154

1-(3-Imidazol-1-yl-propyl)-3-(4-methoxy-7-phenyl-benzothiazol-2-yl)-urea hydrochloride salt (1:1)

Using (4-methoxy-7-phenyl-benzoyhiazol-2-yl)-carbamic acid tert-butyl ester and N-(3-aminopropyl)-imidazole the free base was obtained which was was treated with 5N HCl/EtOH followed by crystallisation from methanol/ether to afford the title compound as a beige solid (72% yield), MS: m/e=408.3 (M+H$^+$).

EXAMPLE 155

1-Ethyl-3-(4-methoxy-7-phenyl-benzothiazol-2-yl)-1-pyridin-4-yl-methyl-urea hydrochloride salt (1:1)

Using (4-methoxy-7-phenyl-benzoyhiazol-2-yl)-carbamic acid tert-butyl ester and 4-(N-ethylaminomethyl)-pyridine the free base was obtained which was was treated with 5N HCl/EtOH followed by crystallisation from aceto-nitrile to afford the title compound as a white solid (64% yield), MS: m/e=419.3 (M+H$^+$).

EXAMPLE 156

1-(2-Imidazol-1-yl-ethyl)-3-(4-methoxy-7-phenyl-benzothiazol-2-yl)-urea hydrochloride salt (1:1)

Using (4-methoxy-7-phenyl-benzoyhiazol-2-yl)-carbamic acid tert-butyl ester and N-(2-aminoethyl)-imidazole the free base was obtained which was was treated with 5N HCl/EtOH followed by crystallisation from aceto-nitrile to afford the title compound as a light brown solid (65% yield), MS: m/e=393.0 (M$^+$).

EXAMPLE 157

Morpholine-4-carboxylic acid (4-methoxy-7-phenyl-benzothiazol-2-yl)-amide

Using (4-methoxy-7-phenyl-benzoyhiazol-2-yl)-carbamic acid tert-butyl ester and morpholine the the title compound was obtained as a white solid, following crystallisation from ether/nHexane (67% yield), MS: m/e=370.3 (M+H$^+$)

EXAMPLE 158

Thiomorpholine-4-carboxylic acid (4-methoxy-7-phenyl-benzothiazol-2-yl)-amide

Using (4-methoxy-7-phenyl-benzoyhiazol-2-yl)-carbamic acid tert-butyl ester and thiomorpholine the the title compound was obtained as a white solid, following crystallisation from ether/nHexane (88% yield), MS: m/e= 386.2 (M+H$^+$).

EXAMPLE 159

1-Oxo-11 4-thiomorpholine-4-carboxylic acid (4-methoxy-7-phenyl-benzothiazol-2-yl)-amide To a solution of thiomorpholine-4-carboxylic acid (4-methoxy-7-phenyl-benzothiazol-2-yl)-amide (240 mg, 0.62 mmol) in CH$_2$Cl$_2$ (10 ml) was added 3-phenyl-2-(phenylsulfonyl) oxaziridine (244 mg, 0.92 mmol) and the mixture stirred for 2 h at r.t. The solvent was then reduced to ca. 2 ml and the mixture ultrasonnicated for 15 min. with addition of ether (10 ml). The solid precipitated was filtered off, then dried under vacuum (0.05 mmHg, 60° C.) to afford the title compoundas a light yellow solid (90% yield), MS: m/e=402.9 (M+H$^+$).

EXAMPLE 160

1-[2-(1,1-Dioxo-11 6-thiomorpholin-4-yl)-ethyl]-3-(4-methoxy-7-phenyl-benzothiazol-2-yl)-urea hydrochloride (1:1)

Using (4-methoxy-7-phenyl-benzoyhiazol-2-yl)-carbamic acid tert-butyl ester 2-(1,1-Dioxo-thiomorpholin-4-yl)-ethylamine the free base was obtained, which was converted to the hydrochloride salt by treatment with 5N HCl/EtOH followed by under vacuum (0.05 mmHg, 60° C.) to afford the title compound as a beige solid (87% yield), MS: m/e=461.2 (M+H$^+$).

EXAMPLE 161

3-(4-Methoxy-7-phenyl-benzothiazol-2-yl)-1-methyl-1-(6-methyl-pyridin-3-yl-methyl)-urea hydrochloride salt (1:2)

Using (4-methoxy-7-phenyl-benzoyhiazol-2-yl)-carbamic acid tert-butyl ester and methyl-(6-methyl-pyridin- 3-ylmethyl)-amine, the free base was obtained, which was converted to the hydrochloride salt by treatment with 5N HCl/EtOH followed by recrystallisation from acetonitrile then drying under vacuum (0.05 mmHg, 60° C.) to afford the title compound as a white solid (61% yield), MS: m/e=448.9 (M+H$^+$).

EXAMPLE 162

3-(4-Methoxy-7-phenyl-benzothiazol-2-yl)-1-methyl-1-pyridin-2-yl-methyl-urea hydrochloride salt (1:2)

Using (4-methoxy-7-phenyl-benzoyhiazol-2-yl)-carbamic acid tert-butyl ester and methyl-pyridin-2-yl-methyl-amine, the free base was obtained, which was converted to the hydrochloride salt by treatment with 5N HCl/EtOH followed by recrystallisation from EtOH/ether then drying under vacuum (0.05 mmHg, 60° C.) to afford the title compound as a white solid (70% yield), MS: m/e=494.4 (M+H$^+$).

EXAMPLE 163

3-(4-Methoxy-7-phenyl-benzothiazol-2-yl)-1-methyl-1-pyridin-4-yl-methyl-urea hydrochloride salt (1:2)

Using (4-methoxy-7-phenyl-benzoyhiazol-2-yl)-carbamic acid tert-butyl ester methyl-pyridin-4-ylmethyl-amine the free base was obtained, which was converted to the hydrochloride salt by treatment with 5N HCl/EtOH followed by recrystallisation from EtOH/ether then drying under vacuum (0.05 mmHg, 60° C.) to afford the title compound as a white solid (65% yield), MS: m/e=480.3 (M+H$^+$).

EXAMPLE 164

3-(4-Methoxy-7-phenyl-benzothiazol-2-yl)-1-methyl-1-(1-oxy-pyridin-3-yl-methyl)-urea To an ice cooled solution of 3-(4-methoxy-7-phenyl-benzothiazol-2-yl)-1-methyl-1-pyridin-3-yl-methyl-urea (405 mg, 1 mmol), in $CH_2Cl_2$ was added 3-chloro-perbenzoicacid (MCPBA) (295 mg, 1.2 mmol) and the mixture stirred at 0° C. for 1 h, followed by 1 h at r.t. After this time the pale red reaction mixture was thoroughly washed with 5% $NaHCO_3$ solution (50 ml), and the aqueous phase was extracted with $CH_2Cl_2$ (2×30 ml) then the combined extracts were dried with $Na_2SO_4$, filtered and evaporated to affording a violet solid. This solid was then chromatographed over $SiO_2$ (Merck 230–400 mesh) eluting with a gradient of $CH_2C_2$/(2N $NH_3$/MeOH) (97:3 to 9:1), to afford the tile compound as a light brown solid (260 mg, 62% yield),MS: m/e=421.3 (M+H$^+$)

EXAMPLE 165

1-Benzyl-3-(4-methoxy-benzothiazol-2-yl)-urea

To a stirred solution of 2-amino-4-methoxy-benzothiazole (180 mg, 1 mol) in THF (5 ml) was added benzylisocyanate (166 mg, 1.25 mmol) and the mixture heated to 60° C. for 3 h. After evaporation of the solvent, ether (5 ml) was added and the suspension ultra-sonnicated for 10 min with addition of nHexane (5 ml). This suspension was filtered and washed further with ether/nHexane (1:1) to afford the title compound, after drying under vacuum, as a white solid (220 mg, 70% yield), MS: m/e=313 (M$^+$).

Following the General Method of Example 165, the Compound of Example 166 was Prepared

EXAMPLE 166

1-Benzyl-3-(4-methoxy-7-phenyl-benzothiazol-2-yl)-urea

Using 2-amino-4-methoxy-7-phenyl-benzothiazole the title compound was obtained as a white amorphous solid (92% yield), MS: m/e=389 (M$^+$)

EXAMPLE 167

1-(4-Methoxy-7-phenyl-benzothiazol-2-yl)-3-pyridin-3-yl-thiourea

To a stirred solution of 2-amino-4-methoxy-7-phenyl-benzothiazole (80 mg, 0.3 mmol) in dioxane (3 ml) was added pyridine-3-isothiocyanate (64 mg, 0.47 mmol) and the mixture heated to 100° C. for 69 h. After cooling to r.t. the resulting yellow suspension was filtered, washed with ether (5 ml) and dried under vacuum (0.05 mmHg, 50° C., to afford the title compound as a; light yellow solid (98 mg, 80% yield), MS: m/e=393.1 (M+H$^+$).

EXAMPLE 168

1-Benzoyl-3-(4-methoxy-7-phenyl-benzothiazol-2-yl)-thiourea

To a suspension of 2-amino-4-methoxy-7-phenyl-benzothiazole (1.52 g, 6 mmol) in dioxane (60 ml) was added benzoylisothiocyanate (1.45 g, 8.9 mmol) and the mixture heated to 100° C. for 2 h, during which time the suspension dissolved. After cooling the solvent was removed and the solids suspended in hot acetonitrile (100 ml) and filtered while warm (50° C.). The solid collected was washed with acetonitrile (20 ml) then dried under vacuum (0.05 mmHg), at 60° C. to afford the title compound as a pale yellow amorphous solid (1.38 g, 55% yield), MS: m/e=419.0 (M$^+$).

EXAMPLE 169

(4-Methoxy-7-phenyl-benzothiazol-2-yl)-thiourea

To a solution of 1-benzoyl-3-(4-methoxy-7-phenyl-benzothiazol-2-yl)-thiourea (1.3 g, 3.1 mmol) in methanol (20 ml)/THF (40 ml) was added NaOMe (250 mg, 4.6 mmol) and the mixture stirrd for 72 h at r.t. After evaporation of the solvents water (100 ml) was added with stirring followed by aceticacid (1 ml) which caused a solid to precipitate. This solid was collected and on a glass sinter, washed with water (100 ml), followed by EtOAc (30 ml) then finally cyclohexane (30 ml). After drying the title compound was obtained as a white solid (850 mg, 87% yield), MS: m/e=316.2 (M+H$^+$).

EXAMPLE 170

(4-Methoxy-benzothiazol-2-yl)-urea

A mixture of 2-amino-4-methoxy-benzothiazole (330 mg, 1.83 mmol) and urea (1.1 g, 1.83 mmol) were heated together for 1 h at 170° C., with evolution of ammonia. After allowing to cool to r.t., water (10 ml) was added and the mixture was vigorously stirred. The solid was then filtered, washed with water (10 ml) followed by ethanol (10 ml) and dried at 60° C. under vaccum (0.05 mmHg). The title product was afforded as an off-white solid (300 mg, 73% yield), MS: m/e=223 (M+).

Following the General Method of Example 170, the Compounds of Examples 171 to 173 were Prepared

EXAMPLE 171

(4-Methoxy-7-phenyl-benzothiazol-2-yl)-urea

Using 2-amino-4-methoxy-7-phenyl-benzothiazole the title compound was prepared as white solid (58% yield), MS: m/e=299 (M+). The preapration of this compound is decribed in the following patent literature; N-(Benzothiazol-2-yl)oxamic acid derivatives. W. Winter, M. Thiel, A. Roesch and O. H. Wilhelms, German Patent, DE 2656468, 1978.

EXAMPLE 172

(4,6-Difluoro-benzothiazol-2-yl)-urea

Using 2-amino-4,6-difluoro-benzothiazole the title compound was prepared as a light yellow solid (42% yield), MS: m/e=229 (M+).

EXAMPLE 173

(7-Isopropyl-4-methoxy-benzothiazol-2-yl)-urea

The title compound is described in the following patent literature and was prepared according to the procedure described therin; N-(Benzothiazol-2-yl)oxamic acid derivatives. W. Winter, M. Thiel, A. Roesch and O. H. Wilhelms, German Patent, DE 2656468, 1978.

EXAMPLE 174

(4-Methoxy-7-phenyl-benzothiazol-2-yl)-pyridin-3-ylmethyl-amine

To a solution of 2-chloro-4-methoxy-7-phenyl-benzothiazole (150 mg, 0.54 mmol), in dioxane (5 ml) was added 3-(aminomethyl)-pyridine (176 mg, 1.6 mmol) and this mixture was stirred at 100° C. for 18 h. The solvent was then evaporated and the mixture taken up in methanol (8 ml) and ultrasonnicated for 10 min. to precipitate the product, which was washed with methanol (5 ml), and dried under vacuum (0.05 mmHg, 60° C.) to afford the title compound as a white solid (58 mg, 31% yield), MS: m/e=348.3 (M+H+).

Following the General Method of Example 174, the Compounds of Examples 175 to 184 were Prepared

EXAMPLE 175

(4-Methoxy-7-phenyl-benzothiazol-2-yl)-pyridin-4-ylmethyl-amine

Using 4-(aminomethyl)-pyridine the title compound was obtained as a pale yellow solid (17% yield), MS: m/e=343.3 (M+H+).

EXAMPLE 176

(4-Methoxy-7-phenyl-benzothiazol-2-yl)-pyridin-2-ylmethyl-amine

Using 2-(aminomethyl)-pyridine the title compound was obtained as a white solid (32% yield), MS: m/e=343.3 (M+H+).

EXAMPLE 177

Benzyl-(4-methoxy-7-phenyl-benzothiazol-2-yl)-amine

Using benzylamine the title compound was obtained as a white solid (54% yield), MS: m/e=347.3 (M+H+).

EXAMPLE 178

(2-Methoxy-ethyl)-(4-methoxy-7-phenyl-benzothiazol-2-yl)-amine

Using 2-methoxy-ethylamine the title compound was obtained as a white solid (56% yield), MS: m/e=315.3 (M+H+).

EXAMPLE 179

Cyclopropylmethyl-(4-methoxy-7-phenyl-benzothiazol-2-yl)-amine

Using aminomethyl-cyclopropane the title compound was obtained as a white solid (68% yield), MS: m/e=311.2 (M+H+).

EXAMPLE 180

(4-Methoxy-7-phenyl-benzothiazol-2-yl)-(2-pyridin-2-yl-ethyl)-amine hydrochloride salt (1:2)

Using 3-(2-aminoethyl)-pyridine the crude product was obtained which was converted to its hydrochloride salt with excess 5N HCl/EtOH (2.5 eq.) and then purified by reversed phase preparative HPLC, using a C18 ODS-AQ column, with a water (0.1% TFA)/acetonitrile gradient. After pooling the product fractions and evaporation of solvents the title compound was obtained as a white foam (59% yield), MS: m/e=362.2 (M+H+).

EXAMPLE 181

N-(4-Methoxy-7-phenyl-benzothiazol-2-yl)-N',N'-dimethyl-ethane-1,2-diamine hydrochloride salt (1:2)

Using 2-(dimethylamino)-ethylamine the crude product was obtained which was converted to its hydrochloride salt with excess 5N HCl/EtOH (2.5 eq.) and then purified by reversed phase preparative HPLC, using a C18 ODS-AQ column, with a water (0.1% TFA)/acetonitrile gradient. After pooling the product fractions and evaporation of solvents the title compound was obtained as a white foam (80% yield), MS: m/e=328.3 (M+H+).

EXAMPLE 182

(4-Methoxy-7-phenyl-benzothiazol-2-yl)-(2-morpholin-4-yl-ethyl)-amine hydrochloride salt (1:2)

Using 4-(2-aminoethyl)morpholine the crude product was obtained which was converted to its hydrochloride salt with excess 5N HCl/EtOH (2.5 eq.) and then purified by reversed phase preparative HPLC, using a C18 ODS-AQ column, with a water (0.1% TFA)/acetonitrile gradient. After pooling the product fractions and evaporation of solvents the title compound was obtained as a white foam (67% yield), MS: m/e=370.3 (M+H+).

EXAMPLE 183

(4-Methoxy-7-phenyl-benzothiazol-2-yl)-(2-piperidin-1-yl-ethyl)-amine hydrochloride salt (1:2)

Using 1-(2-aminoethyl)-piperidine the crude product was obtained which was converted to its hydrochloride salt with excess 5N HCl/EtOH (2.5 eq.) and then purified by reversed phase preparative HPLC, using a C18 ODS-AQ column,

EXAMPLE 184

2-(4-Methoxy-7-phenyl-benzothiazol-2-ylamino)-ethanol hydrochloride salt (1:1)

Using ethanolamine the crude product was obtained which was converted to its hydrochloride salt with excess 5N HCl/EtOH (2.5 eq.) and then purified by reversed phase preparative HPLC, using a C18 ODS-AQ column, with a water (0.1% TFA)/acetonitrile gradient. After pooling the product fractions and evaporation of solvents the title compound was obtained as a white foam (60% yield), MS: m/e=300.4 (M+H$^+$).

EXAMPLE 185

[4-Methoxy-7-(2-methyl-pyridin-4-yl)-benzothiazol-2-yl]-carbamic acid methyl ester The title compound is sysnthesised from (7-iodo-4-methoxy-benzothiazol-2-yl)-carbamic acid methyl ester and 2-methyl-4-trimethylstannanyl-pyridine using the general procedure B as a off-white solid in 20% yield. MS: m/e=329 (M$^+$).

EXAMPLE 186

(4-Methoxy-7-morpholin-4-yl-benzothiazol-2-yl)-carbamic acid methyl ester

Carbamate formation using the same procedure as for (4-methoxy-benzothiazol-2-yl)-carbamic acid methyl ester yields the product as off-white solid in 58% yield. MS: m/e=324 (M+H$^+$).

EXAMPLE 187

(4-Methoxy-7-phenyl-benzothiazol-2-yl)-carbamic acid benzyl ester

To a stirred solution of 2-amino-4-methoxy-7-phenyl-benzothiazole (512 mg, 2 mmol) in pyridine at 90° C. was added benzyl chloroformate (3.3 ml, 23.4 mmol) in three portions over 6 hours. The reaction mixture was then evaporated to dryness and partioned between CH$_2$Cl$_2$ (50 ml) and saturated aqueous NaCl solution (50 ml), the aqueous phase was separated and extracted further with CH$_2$Cl$_2$ (2×50 ml) and the combined organic phases dried, filtered and evaporated. The crude residue was then chromatographed over SiO$_2$ (Merck 230–400 mesh) eluting with CH$_2$Cl$_2$/EtOAc (4:1) to afford the title compound as a white foam (620 mg, 79% yield), MS: m/e=391.2 (M+H$^+$).

EXAMPLE 188

(4-Methoxy-7-vinyl-benzothiazol-2-yl)-carbamic acid methyl ester a) (7-Iodo-4-methoxy-benzothiazol-2-yl)-carbamic acid methyl ester (4-Methoxy-benzothiazol-2-yl)-carbamic acid methyl ester (31.0 g, 130 mmol) and sodium acetate (32.3 g, 394 mmol) are dissolved in 400 ml of glacial acetic acid and slowly treated with iodine monochloride (13.5 ml, 264 mmol) at 0° C. The reaction mixture is then slowly warmed to room temperature and stirred for 15 hours. After addition of water (1.3 l), the formed precipitate is filtered off and washed with water. The filter cake is then dissolved in a minimal amount of tetrahydrofurane (about 150 ml) and decolorized with 1M aqueous sodium thiosulfate. The product is precipitated by the addition of water (about 2.0 l), filtered off and dried at 60° C. for 12 hours. 42.3 g (89%) white solid. MS: m/e=364 (M$^+$).

b) (4-Methoxy-7-vinyl-benzothiazol-2-yl)-carbamic acid methyl ester (7-Iodo-4-methoxy-benzothiazol-2-yl)-carbamic acid ester (1 part), vinyltributylstannane (1.0 equivalents) and tetrakis-(triphenylphosphine)-palladium(0) (0.1 equivalents) are combined in dioxane (25 parts) containing 2M Na$_2$CO$_3$ (4.0 equivalents) and heated to reflux for 24 hours. The reaction mixture was evaporated, washed with brine and dried over MgSO$_4$. After evaporation to dryness the product was isolated by flash chromatography (silica, eluent ethyl acetate/hexanes) as a white solid (60%). F.p.: 138–139° C.

EXAMPLE 189

4-Fluoro-N-(4-methoxy-7-vinyl-benzothiazol-2-yl)-benzamide a) 4-Methoxy-7-vinyl-benzothiazol-2-ylamine (4-Methoxy-7-vinyl-benzothiazol-2-yl)-carbamic acid methyl ester was dissolved in ethylenglycol/2N KOH (2:1) and stirred at 100° C. for 3 hrs. Then water was added and the mixture was extracted with CH$_2$Cl$_2$, the organic phase was washed with brine and dried over MgSO$_4$. After evaporation the residue was crystallized from CH$_2$Cl$_2$. White crystals (64%); F.p.: 155–159° C.

b) 4-Fluoro-N-(4-methoxy-7-vinyl-benzothiazol-2-yl)-benzamide

Following the general method of example 1 the title compound was obtained from 4-methoxy-7-vinyl-benzothiazol-2-ylamine and 4-fluoro-benzoic acid chloride as a white solid (85%); F.p.: 198–199° C.

EXAMPLE 190

(4-Methoxy-7-propenyl-benzothiazol-2-yl)-carbamic acid methyl ester

Following the general method 188b) the title compound was obtained from (7-iodo-4-methoxy-benzothiazol-2-yl)-carbamic acid methyl ester and tributyl-propenyl-stannane as a yellowish solid (75%); F.p.: 153–156° C.

EXAMPLE 191

N-(7-Ethyl-4-methoxy-benzothiazol-2-yl)-4-fluoro-benzamide 100 mg of 4-fluoro-N-(4-methoxy-7-vinyl-benzothiazol-2-yl)-benzamide (0.3 mmol) were dissolved in methanol (100 ml) and Pd/C (4 mg) were added. The reaction mixture was hydrogenated for 2 hrs. After filtering and evaporation of the solvent the crude product was subjected to column chromatography (silica gel, eluent MeOH/CH$_2$Cl$_2$ 1:9). The title compound was obtained in form of white crystals (79%); F.p.: 165–167° C.

EXAMPLE 192

(7-Acetyl-4-methoxy-benzothiazol-2-yl)-carbamic acid methyl ester

According to the method described for example 188b) the title compound was obtained from (7-iodo-4-methoxybenzothiazol-2-yl)-carbamic acid methyl ester (1 equivalent) and (1-ethoxy-vinyl)-tributylstannane (1 equivalent) as a white solid (34%), F.p.: 238–240° C.

EXAMPLE 193

Rac-[7-(1-Hydroxy-ethyl)-4-methoxy-benzothiazol-2-yl]-carbamic acid methyl ester 0.05 g of (7-acetyl-4-methoxy-benzothiazol-2-yl)-carbamic acid methyl ester (0.00018 Mol) were dissolved in ethanol (30 ml) and 0.028 g of $NaBH_4$ (0.00072 Mol) were added. After stirring at 40° C. for 24 hrs. the reaction mixture was diluted with water, extracted with $CH_2Cl_2$, the organic phase washed with brine and dried over $MgSO_4$. After chromatography on silicagel with $CH_2Cl_2$/MeOH 97:3 the title compound was obtained as a white solid (38%); F.p.: 179° C. (dec.).

EXAMPLE 194 (INTERMEDIATE)

Rac-[7-(2-Bromo-1-hydroxy-ethyl)-4-methoxy-benzothiazol-2-yl]-carbamic acid methyl ester 1.5 g of (4-methoxy-7-vinyl-benzothiazol-2-yl)-carbamic acid methyl ester (0.0057 Mol), dissolved in THF (60 ml) were treated with $H_2O$ (6 ml) and 1.0 g of NBS (0.006 Mol) at room temperature for 15 min. Then the solvent was removed, the residue taken up in $H_2O$ (30 ml) and extracted four times with ethyl acetate (50 ml). The combined organic phases were washed with brine and dried over $MgSO_4$. After evaporation the crude product was subjected to column chromatography (silicagel, ethyl acetate). The title compound was obtained as a white solid (78%), F.p.: 150–155° C.

EXAMPLE 195 (INTERMEDIATE)

[7-(2-Bromo-1-hydroxy-propyl)-4-methoxy-benzothiazol-2-yl]-carbamic acid methyl ester According to the method described for the example above the title compound was obtained from (4-methoxy-7-propenyl-benzothiazol-2-yl)-carbamic acid methyl ester as a foam and carried on to the next step without further purification and characterization.

EXAMPLE 196 (INTERMEDIATE)

(7-Bromoacetyl-4-methoxy-benzothiazol-2-yl)-carbamic acid methyl ester 1.6 g of rac-[7-(2-bromo-1-hydroxy-ethyl)-4-methoxy-benzothiazol-2-yl]-carbamic acid methyl ester (0.0044 Mol) were dissolved in $CHCl_3$ (100 ml) and treated with 3.8 g of $MnO_2$ (0.044 Mol) for 3 hrs. at 70° C. The hot reaction mixture was filtered and subsequently concentrated. The crude product was crystallized from $Et_2O$ to yield the title compound as a beige solid (73%); F.p.: 250–260° C. (dec.).

EXAMPLE 197 (INTERMEDIATE)

[7-(2-Bromo-propionyl)-4-methoxy-benzothiazol-2-yl]-carbamic acid methyl ester 5.0 g of [7-(2-bromo-1-hydroxy-propyl)-4-methoxy-benzothiazol-2-yl]-carbamic acid methyl ester 0.0133 Mol) were suspended in water (30 ml) and 2.0 g of $CrO_3$ (0.02 Mol), dissolved in acetic acid (30 ml), were added. The reaction mixture was heated to 70° C. for 2 hrs. and then evaporated to dryness. The residue was taken up in sat. $NaHCO_3$ (200 ml), extracted 4× with ethyl acetate (200 ml each) and the combined organic phases were dried over $MgSO_4$. The title compound was obtained as orange crystals (74%); F.p.: 199–201° C.

EXAMPLE 198

(4-Methoxy-7-thiophen-2-yl-benzothiazol-2-yl)-carbamic acid methyl ester

Following the method described for (4-methoxy-7-vinyl-benzothiazol-2-yl)-carbamic acid methyl ester (Example 188b) the title compound was obtained from (7-iodo-4-methoxy-benzothiazol-2-yl)-carbamic acid methyl ester and 2-tributylstannyl-thiophen as a yellowish solid (41%); 160–165° C.

EXAMPLE 199

[4-Methoxy-7-(5-methyl-thiophen-2-yl)-benzothiazol-2-yl]-carbamic acid methyl ester Following the method described for (4-methoxy-7-vinyl-benzothiazol-2-yl)-carbamic acid methyl ester (Example 188b) the title compound was obtained from (7-iodo-4-methoxy-benzothiazol-2-yl)-carbamic acid methyl ester and 2-tributylstannyl-5-methylthiophen as a yellowish solid (40%); 267–274° C. (dec.).

EXAMPLE 200

[4-Methoxy-7-(2-methyl-thiazol-4-yl)-benzothiazol-2-yl]-carbamic acid methyl ester 1.3 g of (7-bromoacetyl-4-methoxy-benzothiazol-2-yl)-carbamic acid methyl ester (0.0036 Mol) and 0.27 g of thioacetamide (0.0036 Mol) were dissolved in dioxane (30 ml) and stirred for 4 hrs. at 70° C. After evaporation of half of the solvent water (40 ml) was added and the pH adjust to 7 with sat. $NaHCO_3$. A solid precipitated, which was isolated and then subjected to column chromatography on silicagel using ethyl acetate as eluent. The title product was isolated as an off-white solid (27%); F.p.: 186–188° C.

EXAMPLE 201

{4-Methoxy-7-[2-(6-methyl-pyridin-3-yl)-thiazol-4-yl]-benzothiazol-2-yl}-carbamic acid methyl ester According to the method described above the title compound was obtained from (7-bromoacetyl-4-methoxy-benzothiazol-2-yl)-carbamic acid methyl ester and 2-methylpyridine-5-thiocaboxamide as a yellowish solid (73%); F.p.: 240–242° C.

EXAMPLE 202

[4-Methoxy-7-(2-pyridin-2-yl-thiazol-4-yl)-benzothiazol-2-yl]-carbamic acid methyl ester According to the method described above the title compound was obtained from (7-bromoacetyl-4-methoxy-benzothiazol-2-yl)-carbamic acid methyl ester and pyridine-2-thiocaboxamide as a dark red solid (63%); F.p.: 207° C.

EXAMPLE 203

{7-[2-(tert-Butoxycarbonylamino-methyl)-thiazol-4-yl]-4-methoxy-benzothiazol-2-yl}-carbamic acid methyl ester According to the method described above the title compound was obtained from (7-bromoacetyl-4-methoxybenzothiazol-2-yl)-carbamic acid methyl ester and thiocarbamoylmethyl-carbamic acid tert-butyl ester as a white solid (26%); MS (ISP): m/e=451 (M+H$^+$).

EXAMPLE 204

[7-(2-Aminomethyl-thiazol-4-yl)-4-methoxy-benzothiazol-2-yl]-carbamic acid methyl ester hydrochloride (1:1)

0.075 g of {7-[2-(tert-butoxycarbonylamino-methyl)-thiazol-4-yl]-4-methoxy-benzothiazol-2-yl}-carbamic acid methyl ester (0.00017 Mol) were stirred in 2 ml of 2.5 M HCl/MeOH for 4 hrs. Upon cooling to room temperature a precipitate formed, which was filtered off, washed with hexane and dried. The title compound was obtained as a white solid (70%), F.p.: 220–230° C.

EXAMPLE 205

[7-(2-Dimethylaminomethyl-thiazol-4-yl)-4-methoxy-benzothiazol-2-yl]-carbamic acid methyl ester According to the method described for [4-methoxy-7-(2-methyl-thiazol-4-yl)-benzothiazol-2-yl]-carbamic acid methyl ester the title compound was obtained from (7-bromoacetyl-4-methoxy-benzothiazol-2-yl)-carbamic acid methyl ester and dimethylamino-thioacetamide as an off-white solid (11%); F.p.: 185–189° C. (dec.).

EXAMPLE 206

[7-(2,5-Dimethyl-thiazol-4-yl)-4-methoxy-benzothiazol-2-yl]-carbamic acid methyl ester According to the method described above the title compound was obtained from [7-(2-bromo-propionyl)-4-methoxy-benzothiazol-2-yl]-carbamic acid methyl ester and thioacetamide as an off-white solid (42%); F.p.: 180–181° C. (dec.).

EXAMPLE 207

{4-Methoxy-7-[2-(trityl-amino)-thiazol-4-yl]-benzothiazol-2-yl}-carbamic acid methyl ester According to the method described above the title compound was obtained from [7-(2-bromo-acetyl)-4-methoxy-benzothiazol-2-yl]-carbamic acid methyl ester and trityl-thiourea as an off-white solid (53%); F.p.: 135–140° C.

EXAMPLE 208

[7-(2-Amino-thiazol-4-yl)-4-methoxy-benzothiazol-2-yl]-carbamic acid methyl ester 0.070 g of {4-methoxy-7-[2-(trityl-amino)-thiazol-4-yl]-benzothiazol-2-yl}-carbamic acid methyl ester (0.00012 Mol) were heated to reflux in 2 ml of 2.5 M HCl/MeOH for 4 hrs. After cooling to room temperature the pH was adjusted to 7 upon drop wise addition of sat. NaHCO$_3$. A precipitate formed, which was filtered off, washed with ethyl acetate and dried. The title compound was obtained as a white solid (23%), F.p.: 293–296° C. (dec.).

EXAMPLE 209

[7-(2-Dimethylamino-thiazol-4-yl)-4-methoxy-benzothiazol-2-yl]-carbamic acid methyl ester According to the method described above the title compound was obtained from [7-(2-bromo-acetyl)-4-methoxy-benzothiazol-2-yl]-carbamic acid methyl ester, N,N-dimethyl-thiourea and triethylamin as an off-white solid (86%); F.p.: 185–195° C.

EXAMPLE 210

[4-Methoxy-7-(2-pyrrolidin-1-yl-thiazol-4-yl)-benzothiazol-2-yl]-carbamic acid methyl ester According to the method described for the example described above the title compound was obtained from [7-(2-bromo-acetyl)-4-methoxy-benzothiazol-2-yl]-carbamic acid methyl ester and 1-pyrrolidine-carbothioamide as an off-white solid (16%); F.p.: 199° C.

EXAMPLE 211

[4-Methoxy-7-(2-piperidin-1-yl-thiazol-4-yl)-benzothiazol-2-yl]-carbamic acid methyl ester According to the method described above the title compound was obtained from [7-(2-bromo-acetyl)-4-methoxy-benzothiazol-2-yl]-carbamic acid methyl ester and 1-piperidine-carbothioamide as an off-white solid (71%); F.p.: 209 211° C.

EXAMPLE 212

[4-Methoxy-7-(2-morpholin-4-yl-thiazol-4-yl)-benzothiazol-2-yl]-carbamic acid methyl ester According to the method described above the title compound was obtained from [7-(2-bromo-acetyl)-4-methoxy-benzothiazol-2-yl]-carbamic acid methyl ester and 1-morpholine-carbothioamide as a yellowish solid (41%); MS (ISP): m/e=407 (M+H$^+$).

EXAMPLE 213

{4-Methoxy-7-[2-(4-methyl-piperazin-1-yl)-thiazol-4-yl]-benzothiazol-2-yl}-carbamic acid methyl ester According to the method described above the title compound was obtained from [7-(2-bromo-acetyl)-4-methoxy-benzothiazol-2-yl]-carbamic acid methyl ester and 4-methyl-1-piperazinethiocarboxamide as a brownwish solid (41%); F.p.: 143° C.

EXAMPLE 214

[7-(2-tert-Butoxycarbonylamino-1H-imidazol-4-yl)-4-methoxy-benzothiazol-2-yl]-carbamic acid methyl ester 0.25 g of (7-bromoacetyl-4-methoxy-benzothiazol-2-yl)-carbamic acid methyl ester (0.0007 Mol) and 0.33 g of tert-butoxycarbonylguanidine (0.0021 Mol) were heated to reflux in acetonitril (3 ml) for 3 hrs. After evaporation of the solvent the residue was triturated with water (10 ml) and filtered. The filtrate was evaporated and the residue subjected to column chromatography (silicagel, ethyl-acetate/hexanes 1:1) to yield the title compound as a white solid (17%); F.p.: 255–265° C.

EXAMPLE 215

[7-(2-Amino-1H-imidazol-4-yl)-4-methoxy-benzothiazol-2-yl]-carbamic acid methyl ester 0.04 g of [7-(2-tert-butoxycarbonylamino-1H-imidazol-4-yl)-4-methoxy-benzothiazol-2-yl]-carbamic acid methyl ester (0.0001 Mol) were heated to 60° C. in HCl/MeOH (2.5 M, 2 ml). After evaporation of the solvent the residue was dissolved in water (5 ml) and the pH was adjusted to 8 with sat. NaHCO$_3$. The water was evaporated and the residue triturated in ethyl acetate where a precipitation formed. This was isolated and dried to yield the title compound as a grey solid (16%); F.p.: 225–235° C.

The following examples were prepared according to the general method described for 4-methoxy-7-vinyl-benzothiazol-2-yl-amine (Example 189a) from the corresponding carbamic acid methyl ester:

4-Methoxy-7-(2-morpholin-4-yl-thiazol-4-yl)-benzothiazol-2-yl-amine Obtained as a white solid (73%); F.p.: 289–292° C.

4-Methoxy-7-[2-(4-methyl-piperazin-1-yl)-thiazol-4-yl]-benzothiazol-2-yl-amine Obtained as a light yellow solid (81%); F.p.: 176° C. (dec.).

4-Methoxy-7-[2-(6-methyl-pyridin-3-yl)-thiazol-4-yl]-benzothiazol-2-yl-amine Obtained as an off-white solid (94%); MS (ISP): m/e=355 (M+H$^+$).

7-(2-Amino-thiazol-4-yl)-4-methoxy-benzothiazol-2-yl-amine Obtained as a white solid (56%); MS (ISP): m/e=279 (M+H$^+$).

7-(2-Dimethylamino-thiazol-4-yl)-4-methoxy-benzothiazol-2-yl-amine Obtained as a beige solid (62%); F.p.: 225–238° C.

4-Methoxy-7-thiophen-2-yl-benzothiazol-2-yl-amine Obtained as a light brown solid (85%); F.p.: 215–219° C.

4-Methoxy-7-(2-pyridin-2-yl-thiazol-4-yl)-benzothiazol-2-yl-amine Obtained as a light yellow solid (67%); F.p.: 302° C. (dec.). 4-Methoxy-7-(2-pyrrolidin-1-yl-thiazol-4-yl)-benzothiazol-2-yl-amine Obtained as a light brown solid (99%); F.p.: 270° C. (dec.).

4-Methoxy-7-(2-piperidin-1-yl-thiazol-4-yl)-benzothiazol-2-yl-amine Obtained as a light brown solid (75%); MS (ISP): m/e=347 (M+H$^+$).

4-Methoxy-7-(2-methyl-thiazol-4-yl)-benzothiazol-2-yl-amine Obtained as an off-white solid (81%); F.p.: 262–265° C.

4-Methoxy-7-(5-methyl-thiophen-2-yl)-benzothiazol-2-yl-amine Obtained as an off-white solid (81%); F.p.: 195–205° C. (dec.).

7-(2,5-Dimethyl-thiazol-4-yl)-4-methoxy-benzothiazol-2-yl-amine Obtained as a yellow solid (5%); F.p.: 201–20 3° C.

Following the General Method of Example 1 the Following Examples were Obtained from Corresponding Benzothiazol-2-yl-amines and 4-fluoro-benzoic Acid Chloride

EXAMPLE 216

4-Fluoro-N-[4-methoxy-7-(2-morpholin-4-yl-thiazol-4-yl)-benzothiazol-2-yl]-benzamide Obtained as an off-white solid (53%); F.p.: 225–227° C.

EXAMPLE 217

N-[7-(2-Amino-thiazol-4-yl)-4-methoxy-benzothiazol-2-yl]-4-fluoro-benzamide

Obtained as a white solid (85%); F.p.: 262–264° C.

EXAMPLE 218

4-Fluoro-N-{4-methoxy-7-[2-(6-methyl-pyridin-3-yl)-thiazol-4-yl]-benzothiazol-2-yl}-benzamide Obtained as an off-white solid (79%); MS (ISP): m/e=477 (M+H$^+$).

EXAMPLE 219

N-[7-(2-Dimethylamino-thiazol-4-yl)-4-methoxy-benzothiazol-2-yl]-4-fluoro-benzamide Obtained as a light yellow solid (29%); F.p.: 218–220° C.

EXAMPLE 220

4-Fluoro-N-(4-methoxy-7-thiophen-2-yl-benzothiazol-2-yl)-benzamide

Obtained as a light yellow solid (72%); F.p.: 242–250° C.

EXAMPLE 221

4-Fluoro-N-{4-methoxy-7-[2-(4-methyl-piperazin-1-yl)-thiazol-4-yl]-benzothiazol-2-yl}-benzamide Obtained as an off-white solid (66%); F.p.: 138° C. (dec.).

EXAMPLE 222

4-Fluoro-N-[4-methoxy-7-(2-pyridin-2-yl-thiazol-4-yl)-benzothiazol-2-yl]-benzamide Obtained as an off-white solid (92%); F.p.: 150° C. (dec.).

EXAMPLE 223

4-Fluoro-N-[4-methoxy-7-(2-pyrrolidin-1-yl-thiazol-4-yl)-benzothiazol-2-yl]-benzamide Obtained as an off-white solid (82%); MS (ISP): m/e=455 (M+H$^+$).

EXAMPLE 224

4-Fluoro-N-[4-methoxy-7-(2-methyl-thiazol-4-yl)-benzothiazol-2-yl]-benzamide

Obtained as a white solid (36%); F.p.: 217–219° C.

EXAMPLE 225

4-Fluoro-N-[4-methoxy-7-(5-methyl-thiophen-2-yl)-benzothiazol-2-yl]-benzamide

Obtained as an off-white solid (70%); F.p.: 192–196° C. (dec.).

EXAMPLE 226

N-[7-(2,5-Dimethyl-thiazol-4-yl)-4-methoxy-benzothiazol-2-yl]-4-fluoro-benzamide Obtained as an off-white solid (42%); F.p.: 205–206° C. (dec.).

EXAMPLE 227

4-Chloromethyl-N-[4-methoxy-7-(2-morpholin-4-yl-thiazol-4-yl)-benzothiazol-2-yl]-benzamide 0.165 g of 4-methoxy-7-(2-morpholin-4-yl-thiazol-4-yl)-benzothiazol-2-ylamine (0.00047 Mol) were dissolved in dioxane (5 ml) and combined with 0.1 ml of triethylamine (0.0007 Mol), 0.006 g DMAP (0.000047 Mol) and a solution of 0.116 g of 4-(chlormethyl)benzoylchlorid (0.00062 Mol) in dioxane (1 ml). The reaction mixture was stirred for 6 hrs. at 70° C. After cooling down to room temperature, water (10 ml) and sat. NaHCO$_3$ (10 ml) were added. A precipitation formed. It was filtered, washed with water and tried. This crude product was subjected to column chromatography (silicagel, CH$_2$Cl$_2$/MeOH 19:1). The title compound was obtained as a light yellow solid (65%); F.p.: 166–168° C. The Following Examples were Prepared from the Corresponding 7-substituted 4-methoxy-benzothiazol-2-yl-amines According to the Above Described Method

EXAMPLE 228

4-Chloromethyl-N-{4-methoxy-7-[2-(6-methyl-pyridin-3-yl)-thiazol-4-yl]-benzothiazol-2-yl}-benzamide Obtained as an off-white solid (68%); F.p.: 230–250° C.

EXAMPLE 229

4-Chloromethyl-N-{4-methoxy-7-[2-(trityl-amino)-thiazol-4-yl]-benzothiazol-2-yl}-benzamide Obtained as a white solid (42%); F.p.: 163° C. (dec.).

EXAMPLE 230

4-Chloromethyl-N-[7-(2-dimethylamino-thiazol-4-yl)-4-methoxy-benzothiazol-2-yl]-benzamide Obtained as a light yellow solid (36%); F.p.: 183–186° C.

EXAMPLE 231

4-Chloromethyl-N-(4-methoxy-7-thiophen-2-yl-benzothiazol-2-yl)-benzamide

Obtained as a light yellow solid (60%); F.p.: 183–209° C. (dec.).

EXAMPLE 232

4-Chloromethyl-N-[4-methoxy-7-(2-pyridin-2-yl-thiazol-4-yl)-benzothiazol-2-yl]-benzamide Obtained as a light brown solid (79%); F.p.: 195–201° C.

EXAMPLE 233

4-Chloromethyl-N-[4-methoxy-7-(2-methyl-thiazol-4-yl)-benzothiazol-2-yl]-benzamide Obtained as a white solid (72%); F.p.: 140–145° C.

EXAMPLE 234

4-Chloromethyl-N-[4-methoxy-7-(5-methyl-thiophen-2-yl)-benzothiazol-2-yl]-benzamide Obtained as a yellow solid (93%); F.p.: 130–146° C.

EXAMPLE 235

4-{[(2-Methoxy-ethyl)-methyl-amino]-methyl}-N-[4-methoxy-7-(2-morpholin-4-yl-thiazol-4-yl)-benzothiazol-2-yl]-benzamide 0.035 g N-(2-methoxyethyl)-methylamine (0.00039 Mol) and 0.064 g (4-chloromethyl-N-[4-methoxy-7-(2-morpholin-4-yl-thiazol-4-yl)-benzothiazol-2-yl]-benzamide (0.00013 Mol) dissolved in THF (2 ml) were heated to reflux for 4 hrs. After cooling to room temperature and evaporation of the solvent the residue was triturated with water (7 ml). A precipitation formed, which was filtered, washed with water and dried yielding the title product as an off-white solid (79%); F.p.: 100–110° C.

The following examples were prepared according to the method above from N-(2-methoxyethyl)methylamin and the corresponding 7-substituted 4-chloromethyl-N-[4-methoxy-benzothiazol-2-yl]-benzamides:

EXAMPLE 236

4-{[(2-Methoxy-ethyl)-methyl-amino]-methyl}-N-{4-methoxy-7-[2-(trityl-amino)-thiazol-4-yl]-benzothiazol-2-yl}-benzamide Obtained as a white solid (79%); F.p.: 119–128° C.

EXAMPLE 237

N-[7-(2-Amino-thiazol-4-yl)-4-methoxy-benzothiazol-2-yl]-4-{[(2-methoxy-ethyl)-methyl-amino]-methyl}-benzamide g of 4-{[(2-methoxy-ethyl)-methyl-amino]-methyl}-N-{4-methoxy-7-[2-(trityl-amino)-thiazol-4-yl]-benzothiazol-2-yl}-benzamide (0.00014 Mol) were treated with cc HCl (0.03 ml) in MeOH (1 ml) for 1 h at reflux. After evaporation of the solvent the residue was taken up in water (10 ml), treated with sat. NaHCO$_3$ (10 ml) and extracted 4× with ethyl acetate. The combined organic phases were dried over Na$_2$SO$_4$, filtered and concentrated. The residue was subjected to column chromatography (silicagel, ethyl acetate, CH$_2$Cl$_2$/MeOH 19:1 and 9:1). The title compound was obtained as a white solid (53%); F.p.: 199–206° C.

EXAMPLE 238

4-{[(2-Methoxy-ethyl)-methyl-amino]-methyl}-N-{4-methoxy-7-[2-(6-methyl-pyridin-3-yl)-thiazol-4-yl]-benzothiazol-2-yl}-benzamide Obtained as a light yellow foam (69%); MS (ISP): m/e=560 (M+H$^+$).

EXAMPLE 239

N-[7-(2-Dimethylamino-thiazol-4-yl)-4-methoxy-benzothiazol-2-yl]-4-{[(2-methoxy-ethyl)-methyl-amino]-methyl}-benzamide Obtained as a light yellow solid (47%); F.p.: 85–95° C.

EXAMPLE 240

4-{[(2-Methoxy-ethyl)-methyl-amino]-methyl}-N-(4-methoxy-7-thiophen-2-yl-benzothiazol-2-yl)-benzamide Obtained as a light beige solid (44%); F.p.: 58–78° C.

EXAMPLE 241

4-{[(2-Methoxy-ethyl)-methyl-amino]-methyl}-N-[4-methoxy-7-(2-pyridin-2-yl-thiazol-4-yl)-benzothiazol-2-yl]-benzamide Obtained as a light yellow solid (54%); MS (ISP): m/e=546 (M+H$^+$).

EXAMPLE 242

4-{[(2-Methoxy-ethyl)-methyl-amino]-methyl}-N-[4-methoxy-7-(2-methyl-thiazol-4-yl)-benzothiazol-2-yl]-benzamide Obtained as a white solid (36%); F.p.: 140–145° C.

EXAMPLE 243

4-{[(2-Methoxy-ethyl)-methyl-amino]-methyl}-N-[4-methoxy-7-(5-methyl-thiophen-2-yl)-benzothiazol-2-yl]-benzamide Obtained as a light beige solid (73%); F.p.: 83–90° C.

EXAMPLE 244

N-[4-Methoxy-7-(2-morpholin-4-yl-thiazol-4-yl)-benzothiazol-2-yl]-4-pyrrolidin-1-yl-methyl-benzamide 0.032 g pyrrolidine (0.00045 Mol) and 0.075 g (4-chloromethyl-N-[4-methoxy-7-(2-morpholin-4-yl-thiazol-4-yl)-benzothiazol-2-yl]-benzamide (0.00015 Mol) dissolved in THF (2 ml) were heated to reflux for 1 h. After cooling to room temperature and evaporation of the solvent the residue was triturated with water (7 ml). A precipitation formed, which was filtered, washed with water and dried yielding the title product as an off-white solid (87%); F.p.: 120–130° C.

The Following Examples were Prepared According to the Method above from Pyrrolidine and the Corresponding 7-substituted 4-chloromethyl-N-[4-methoxy-benzothiazol-2-yl]-benzamides

EXAMPLE 245

N-{4-Methoxy-7-[2-(6-methyl-pyridin-3-yl)-thiazol-4-yl]-benzothiazol-2-yl}-4-pyrrolidin-1-yl-methyl-benzamide Obtained as a light brown solid (58%); F.p.: 230–231° C.

EXAMPLE 246

N-{4-Methoxy-7-[2-(trityl-amino)-thiazol-4-yl]-benzothiazol-2-yl}-4-pyrrolidin-1-yl-methyl-benzamide Obtained as a light yellow solid (89%); F.p.: 122–135° C.

EXAMPLE 247

N-[7-(2-Amino-thiazol-4-yl)-4-methoxy-benzothiazol-2-yl]-4-pyrrolidin-1-yl-methyl-benzamide hydrochloride (1:1)

0.055 g of N-{4-methoxy-7-[2-(trityl-amino)-thiazol-4-yl]-benzothiazol-2-yl}-4-pyrrolidin-1-ylmethyl-benzamide (0.000078 Mol) were dissolved in MeOH (0.5 ml) and ccHCl (0.015 ml). After refluxing for 1 h the solvent was evaporated, the residue treated with ethyl acetate, filtered and isolated. This material was triturated in EtOH whereby crystals formed, which were washed with $Et_2O$. After drying the title compound was obtained as a white solid (62%); F.p.: 228–240° C.

EXAMPLE 248

N-[7-(2-Dimethylamino-thiazol-4-yl)-4-methoxy-benzothiazol-2-yl]-4-pyrrolidin-1-yl methyl-benzamide Obtained as a light yellow solid (75%); F.p.: 120–136° C.

EXAMPLE 249

N-(4-Methoxy-7-thiophen-2-yl-benzothiazol-2-yl)-4-pyrrolidin-1-yl-methyl-benzamide Obtained as a light beige solid (47%); F.p.: 174–190° C. (dec.).

EXAMPLE 250

N-[4-Methoxy-7-(2-pyridin-2-yl-thiazol-4-yl)-benzothiazol-2-yl]-4-pyrrolidin-1-yl-methyl-benzamide Obtained as a light yellow foam (48%); MS (ISP): m/e= 528 (M+H$^+$).

EXAMPLE 251

N-[4-Methoxy-7-(5-methyl-thiophen-2-yl)-benzothiazol-2-yl]-4-pyrrolidin-1-yl-methyl-benzamide Obtained as a light beige solid (67%); F.p.: 140–149° C. (dec.).

EXAMPLE 252

N-[4-Methoxy-7-(2-methyl-thiazol-4-yl]-benzothiazol-2-yl)-4-pyrrolidin-1-yl-methyl-benzamide Obtained as a light yellow solid (44%); F.p.: 123–134° C.

EXAMPLE 253

N-(4-Methoxy-7-thiophen-2-yl-benzothiazol-2-yl)-2-methyl-isonicotinamide 0.21 g of 4-methoxy-7-thiophen-2-yl-benzothiazol-2-yl-amine (0.0008 Mol) together with 0.27 ml triethylamine (0.002 Mol), 0.01 g of DMAP and 0.20 g isonicotinic acid chloride (0.001 Mol) were heated to reflux for 20 hrs. in dioxane (10 ml). After cooling to room temperature water (20 ml) and sat. $NaHCO_3$ (15 ml) were added. A precipitation formed, which was filtered, washed with water and dried. This crude product was subjected to column chromatography (silicagel, ethyl acetate) to yield the title compound as a yellow solid (58%); F.p.: 203–211° C. (dec.).

The Following Examples were Prepared According to the Method above from Isonicotinic Acid Chloride and the Corresponding 7-substituted 4-methoxy-benzothiazol-2-yl-amines

EXAMPLE 254

N-[4-Methoxy-7-(2-pyridin-2-yl-thiazol-4-yl)-benzothiazol-2-yl]-2-methyl-isonicotinamide Obtained as a light yellow solid (38%); MS (ISP): m/e= 460 (M+H$^+$).

EXAMPLE 255

N-[4-Methoxy-7-(2-pyrrolidin-1-yl-thiazol-4-yl)-benzothiazol-2-yl]-2-methyl-isonicotinamide Obtained as a yellow solid (9%); F.p.: 195–215° C.

EXAMPLE 256

N-{4-Methoxy-7-[2-(4-methyl-piperazin-1-yl)-thiazol-4-yl]-benzothiazol-2-yl}-2-methyl-isonicotinamide Obtained as a yellow foam (4%); MS (ISP): m/e=481 (M+H$^+$).

EXAMPLE 257

N-[4-Methoxy-7-(5-methyl-thiophen-2-yl)-benzothiazol-2-yl]-2-methyl-isonicotinamide Obtained as a light orange foam (65%); MS (ISP): m/e= 396 (M+H$^+$).

EXAMPLE 258

Morpholine-4-carboxylic acid {4-methoxy-7-[2-(6-methyl-pyridin-3-yl)-thiazol-4-yl]-benzothiazol-2-yl}-amide 0.1 g of 4-methoxy-7-[2-(6-methyl-pyridin-3-yl)-thiazol-4-yl]-benzothiazol-2-ylamine (0.00028 Mol) were dissolved in dioxane (2 ml) and treated with 0.047 ml triethylamine (0.00034 Mol) and 0.164 ml of phosgene (20% in toluene) (0.00031 Mol). After stirring for 2 hrs. at room temperature 0.122 ml of morpholine (0.0014 Mol) were added and the whole mixture was stirred for 16 hrs. at ambient temperature. Upon addition of water (5 ml) a precipitation formed, which was filtered, washed with water and dried. This crude material was triturated with hot MeOH and after cooling to room temperature filtered. The filtrate was evaporated and the residue subjected to column chromatography (silicagel, $CH_2Cl_2/MeOH+1\%$ $NH_4OH$). The title compound was obtained as a light yellow solid (7%); MS (ISP): m/e=468 $(M+H^+)$.

EXAMPLE 259

Morpholine-4-carboxylic acid [4-methoxy-7-(2-pyridin-2-yl-thiazol-4-yl)-benzothiazol-2-yl]-amide g of 4-methoxy-7-[2-pyridin-2-yl)-thiazol-4-yl]-benzothiazol-2-yl-amine (0.00029 Mol) were dissolved in THF (5 ml) and treated with 0.063 ml ethyldiisopropylamine (0.00037 Mol), DMAP (1 mg) and 0.029 mg of triphosgene (0.0001 Mol). After heating to reflux for 30 min., 0.0322 ml of morpholine (0.00037 Mol) and another 0.062 ml of ethyldiisopropylamine were added and the whole mixture was stirred for 16 hrs. at reflux. After cooling to room temperature water (10 ml) was added and the reaction mixture was extracted with ethyl acetate (4x, 15 ml each). The combined organic phases were dried over $Na_2SO_4$, filtered and evaporated. The residue was subjected to column chromatography (silicagel, ethyl acetate). The title compound was obtained as a light yellow solid (7%); F.p.: 152–178° C. (dec.).

EXAMPLE 260

Morpholine-4-carboxylic acid [4-methoxy-7-(2-methyl-thiazol-4-yl)-benzothiazol-2-yl]-amide 0.07 g of 7-(2-Amino-thiazol-4-yl)-4-methoxy-benzothiazol-2-yl-amine (0.00025 Mol) were suspended in dioxane (4 ml) and treated with 0.028 g of NaH (60% dispersion in oil) (0.0006 Mol) for 1 h at room temperature. Then 0.11 ml of triethylamine (0.00076 Mol) and 0.07 ml of morpholine-4-carbonylchloride (0.0006 Mol) were added and the reaction mixture was stirred at room temperature for 3 hrs. Then water (15 ml) was added and the reaction mixture was extracted with ethyl acetate (4x, 20 ml each). The combined organic phases were dried over $Na_2SO_4$, filtered and evaporated. The residue was subjected to column chromatography (silicagel, ethyl acetate). The title compound was obtained as a light yellow solid (61%); F.p.: 223–226° C. (dec.).

The Following Examples were Prepared According to the Method above from Morpholin-4-carbonylchloride and the Corresponding 7-substituted 4-methoxy-benzothiazol-2-ylamines

EXAMPLE 261

Morpholine-4-carboxylic acid {4-methoxy-7-[2-(4-methyl-piperazin-1-yl)-thiazol-4-yl]-benzothiazol-2-yl}-amide Obtained as a beige solid (40%); F.p.: 150–170° C.

EXAMPLE 262

Morpholine-4-carboxylic acid [4-methoxy-7-(2-piperidin-1-yl-thiazol-4-yl)-benzothiazol-2-yl]-amide Obtained as a light yellow solid (25%); F.p.: 227–234° C.

EXAMPLE 263

Morpholine-4-carboxylic acid (4-methoxy-7-thiophen-2-yl-benzothiazol-2-yl)-amide Obtained as a light beige solid (37%); F.p.: 175–182° C. (dec.).

EXAMPLE 264

Morpholine-4-carboxylic acid [4-methoxy-7-(5-methyl-thiophen-2-yl)-benzothiazol-2-yl]-amide Obtained as a light beige solid (59%); F.p.: 173–180° C. (dec.).

EXAMPLE 265

4-Hydroxy-piperidine-1-carboxylic acid [4-methoxy-7-(2-methyl-thiazol-4-yl)-benzothiazol-2-yl]-amide To a suspension of 0.070 g of 4-methoxy-7-(2-methyl-thiazol-4-yl)-benzothiazol-2-ylamine (0.00025 Mol) in THF (4 ml) at room temperature were added 0.054 ml N-ethyl-diisopropylamine (0.00031 Mol) and 0.001 g DMAP. 0.025 g of triphosgen (0.000085 Mol) were added and the whole mixture was heated to 70° C. for 1 hr. Then another 0.054 ml N-ethyl-diisopropylamine (0.00031 Mol) and 0.031 g of 4-hydroxy-piperidin (0.00031 Mol) were added and the reaction mixture was stirred at 70° C. for 1.5 hrs. Upon cooling to room temperature a precipitation formed, which was filtered and washed with THF. The filtrate was evaporated and the residue was subjected to column chromatography (silicagel, $CH_2Cl_2/MeOH$ 9:1). The title product was obtained as a white solid (11%); F.p.: 145–150° C.

The Following Example was Prepared According to the above Described Methode from 4-methoxy-7-(5-methyl-thiophene-2-yl)-benzothiazol-2-yl-amine

EXAMPLE 266

4-Hydroxy-piperidine-1-carboxylic acid [4-methoxy-7-(5-methyl-thiophen-2-yl)-benzothiazol-2-yl]-amide Obtained as a yellow solid (10%); F.p.: 197–204° C. (dec.).

The Following Example was Prepared According to the Methode Described Above from N-methyl-piperazine and 4-methoxy-7-(2-methyl-thiazol-4-yl)-benzothiazol-2-ylamine

EXAMPLE 267

4-Methyl-piperazine-1-carboxylic acid [4-methoxy-7-(2-methyl-thiazol-4-yl)-benzothiazol-2-yl]-amide Obtained as a white solid (8%); F.p.: 179–181° C.

EXAMPLE 268

{2-[4-(4-Methoxy-7-morpholin-4-yl-benzothiazol-2-ylcarbamoyl)-phenyl]-ethyl}-methyl-carbamic acid tert-butyl ester Using [2-(4-chlorocarbonyl-phenyl)-ethyl]-methyl-carbamic acid tert-butyl ester the title compound was prepared using the general method of example 1 as white solid (16%), MS: m/e=527 (M+H$^+$).

EXAMPLE 269

N-(4-Methoxy-7-morpholin-4-yl-benzothiazol-2-yl)-4-(1,1,2,2-tetrafluoro-ethoxy)-benzamide Using 4-(1,1,2,2-tetrafluoro-ethoxy)-benzoyl chloride the title compound was prepared using the general method of example 1 as light yellow solid (35%), MS: m/e=486 (M+H$^+$).

EXAMPLE 270

4-[(2-Methoxy-ethyl)-methyl-sulfamoyl]-N-(4-methoxy-7-morpholin-4-yl-benzothiazol-2-yl)-benzamide Using (2-methoxy-ethyl)-methyl-sulfamic acid chloride the title compound was prepared using the general method of example 1 as red solid (44%), MS: m/e=521 (M+H$^+$).

EXAMPLE 271

N-(4-Methoxy-7-morpholin-4-yl-benzothiazol-2-yl)-4-trifluoromethyl-benzamide

Using 4-(trifluoromethyl)-benzoyl chloride the title compound was prepared using the general method of example 1 as white solid (58%), MS: m/e=438 (M+H$^+$).

EXAMPLE 272

N-(4-Methoxy-7-morpholin-4-yl-benzothiazol-2-yl)-3-trifluoromethoxy-benzamide

Using 3-(trifluoro-methoxy)-benzoyl chloride the title compound was prepared using the general method of example 1 as light yellow solid (84%), MS: m/e=454 (M+H$^+$).

EXAMPLE 273

N-(4-Methoxy-7-morpholin-4-yl-benzothiazol-2-yl)-4-trifluoromethoxy-benzamide

Using 4-(trifluoro-methoxy)-benzoyl chloride the title compound was prepared using the general method of example 1 as yellow solid (77%), MS: m/e=453 (M$^+$).

EXAMPLE 274

4-Ethyl-N-(4-methoxy-7-morpholin-4-yl-benzothiazol-2-yl)-benzamide

Using 4-ethyl-benzoyl chloride the title compound was prepared using the general method of example 1 as white solid (21%), MS: m/e=397 (M+H$^+$).

EXAMPLE 275

4-Fluoro-N-(4-methoxy-7-morpholin-4-yl-benzothiazol-2-yl)-benzamide

Using 4-fluoro-benzoyl chloride the title compound was prepared using the general method of example 1 as white solid (64%), MS: m/e=388 (M+H$^+$).

EXAMPLE 276

N-(4-Methoxy-7-morpholin-4-yl-benzothiazol-2-yl)-2-methyl-isonicotinamide

Using 2-methyl-isonicotinyl chloride the title compound was prepared using the general method of example 1 as white solid (72%), MS: m/e=385 (M+H$^+$).

EXAMPLE 277

N-(4-Methoxy-7-morpholin-4-yl-benzothiazol-2-yl)-benzamide

Using benzoyl chloride the title compound was prepared using the general method of example 1 as white solid (85%), MS: m/e=370 (M+H$^+$).

The Following Compounds are Described According to the General Procedure C in Example 126

EXAMPLE 278

4-Chloro-3-{[ethyl-(2-methoxy-ethyl)-amino]-methyl}-N-(4-methoxy-7-morpholin-4-yl-benzothiazol-2-yl)-benzamide Using 4-chloro-3-chloromethyl-benzoyl chloride and ethyl-(2-methoxy-ethyl)-amine the title compound was prepared using the general procedure C as off-white solid (69%), MS: m/e=519 (M+H$^+$).

EXAMPLE 279

N-(4-Methoxy-7-morpholin-4-yl-benzothiazol-2-yl)-3-methylaminomethyl-benzamide

Using 3-chloromethyl-benzoyl chloride and methylamine the title compound was prepared using the general procedure C as white solid (44%), MS: m/e=413 (M+H$^+$).

EXAMPLE 280

4-Chloro-N-(4-methoxy-7-morpholin-4-yl-benzothiazol-2-yl)-3-methylaminomethyl-benzamide Using 4-chloro-3-chloromethyl-benzoyl chloride and methylamine the title compound was prepared using the general procedure C as light yellow solid (69%), MS: m/e=447 (M+H$^+$).

EXAMPLE 281

4-Chloro-3-{[(2-methoxy-ethyl)-methyl-amino]-methyl}-N-(4-methoxy-7-morpholin-4-yl-benzothiazol-2-yl)-benzamide Using 4-chloro-3-chloromethyl-benzoyl chloride and (2-methoxy-ethyl)-methyl-amine the title compound was prepared using the general procedure C as off-white solid (54%), MS: m/e=505 (M+H$^+$).

EXAMPLE 282

4-Chloro-3-[(2-methoxy-ethylamino)-methyl]-N-(4-methoxy-7-morpholin-4-yl-benzothiazol-2-yl)-benzamide Using 4-chloro-3-chloromethyl-benzoyl chloride and 2-methoxy-ethylamine the title compound was prepared using the general procedure C as off-white solid (69%), MS: m/e=491 (M+H$^+$).

EXAMPLE 283

4-Chloro-N-(4-methoxy-7-morpholin-4-yl-benzothiazol-2-yl)-3-pyrrolidin-1-ylmethyl-benzamide Using 4-chloro-3-chloromethyl-benzoyl chloride and pyrrolidine the title compound was prepared using the general procedure C as light yellow solid (72%), MS: m/e=487 (M+H$^+$)

EXAMPLE 284

1-[4-(4-Benzyloxy-7-morpholin-4-yl-benzothiazol-2-ylcarbamoyl)-benzyl]-pyridinium; chloride Using 4-benzyloxy-7-morpholin-4-yl-benzothiazol-2-ylamine, 4-chloromethyl-benzoyl chloride and pyridine the title compound was prepared using the general procedure C as white solid (80%), MS: m/e=538 (M+).

EXAMPLE 285

3-Fluoro-N-(4-methoxy-7-morpholin-4-yl-benzothiazol-2-yl)-4-pyrrolidin-1-ylmethyl-benzamide Using 4-chloromethyl-3-fluoro-benzoyl chloride and pyrrolidine the title compound was prepared using the general procedure C as yellow solid (25%), MS: m/e=471 (M+H+).

EXAMPLE 286

3-[(2-Methoxy-ethylamino)-methyl]-N-(4-methoxy-7-morpholin-4-yl-benzothiazol-2-yl)-benzamide Using 3-chloromethyl-benzoyl chloride and 2-methoxy-ethylamine the title compound was prepared using the general procedure C as light yellow solid (68%), MS: m/e=457 (M+H+).

EXAMPLE 287

3-{[(2-Methoxy-ethyl)-methyl-amino]-methyl}-N-(4-methoxy-7-morpholin-4-yl-benzothiazol-2-yl)-benzamide Using 3-chloromethyl-benzoyl chloride and (2-methoxy-ethyl)-methyl-amine the title compound was prepared using the general procedure C as yellow solid (75%), MS: m/e=471 (M+H+).

EXAMPLE 288

1-[4-(4-Methoxy-7-morpholin-4-yl-benzothiazol-2-ylcarbamoyl)-benzyl]-pyridinium; chloride Using 4-chloromethyl-benzoyl chloride and pyridine the title compound was prepared using the general procedure C as white solid (33%), MS: m/e=462 (M+).

EXAMPLE 289

N-(4-Methoxy-7-morpholin-4-yl-benzothiazol-2-yl)-3-pyrrolidin-1-ylmethyl-benzamide Using 3-chloromethyl-benzoyl chloride and pyrrolidine the title compound was prepared using the general procedure C as light yellow solid (65%), MS: m/e=454 (M+H+).

EXAMPLE 290

4-[(2-Ethoxy-ethylamino)-methyl]-N-(4-methoxy-7-morpholin-4-yl-benzothiazol-2-yl)-benzamide Using 4-chloromethyl-benzoyl chloride and 2-ethoxy-ethylamine the title compound was prepared using the general procedure C as white solid (18%), MS: m/e=471 (M+H+).

EXAMPLE 291

[R]-N-(4-Methoxy-7-morpholin-4-yl-benzothiazol-2-yl)-4-(3-methoxy-pyrrolidin-1-yl-methyl)-benzamide Using 4-chloromethyl-benzoyl chloride and [R]-3-methoxy-pyrrolidine the title compound was prepared using the general procedure C as light yellow solid (18%), MS: m/e=483 (M+H+).

EXAMPLE 292

N-(4-Methoxy-7-morpholin-4-yl-benzothiazol-2-yl)-4-methylaminomethyl-benzamide

Using 4-chloromethyl-benzoyl chloride and methylamine the title compound was prepared using the general procedure C as light yellow solid (63%), MS: m/e=413 (M+H+).

EXAMPLE 293

[S]-N-(4-Methoxy-7-morpholin-4-yl-benzothiazol-2-yl)-4-(3-methoxy-pyrrolidin-1-ylmethyl)-benzamide Using 4-chloromethyl-benzoyl chloride and [S]-3-methoxy-pyrrolidine the title compound was prepared using the general procedure C as light brown solid (13%), MS: m/e=483 (M+H+).

EXAMPLE 294

4-Azetidin-1-ylmethyl-N-(4-methoxy-7-morpholin-4-yl-benzothiazol-2-yl)-benzamide Using 4-chloromethyl-benzoyl chloride and azetidine the title compound was prepared using the general procedure C as light yellow solid (33%), MS: m/e=439 (M+H+).

EXAMPLE 295

4-[1-(2-Methoxy-ethylamino)-ethyl]-N-(4-methoxy-7-morpholin-4-yl-benzothiazol-2-yl)-benzamide Using 4-(1-chloro-ethyl)-benzoyl chloride and 2-methoxy-ethylamine the title compound was prepared using the general procedure C as yellow solid (52%), MS: m/e=471 (M+H+).

EXAMPLE 296

4-{1-[(2-Methoxy-ethyl)-methyl-amino]-ethyl}-N-(4-methoxy-7-morpholin-4-yl-benzothiazol-2-yl)-benzamide Using 4-(1-chloro-ethyl)-benzoyl chloride and (2-methoxy-ethyl)-methyl-amine the title compound was prepared using the general procedure C as yellow solid (91%), MS: m/e=485 (M+H+).

EXAMPLE 297

N-(4-Methoxy-7-morpholin-4-yl-benzothiazol-2-yl)-4-(1-pyrrolidin-1-yl-ethyl)-benzamide Using 4-(1-chloro-ethyl)-benzoyl chloride and pyrrolidine the title compound was prepared using the general procedure C as yellow solid (68%), MS: m/e=467 (M+H+).

EXAMPLE 298

4-(2-Dimethylamino-ethylsulfanylmethyl)-N-(4-methoxy-7-morpholin-4-yl-benzothiazol-2-yl)-benzamide Using 4-chloromethyl-benzoyl chloride and 2-dimethylamino-ethanethiol the title compound was prepared using the general procedure C as yellow solid (52%), MS: m/e=487 (M+H+).

EXAMPLE 299

(rac) N-(4-Methoxy-7-morpholin-4-yl-benzothiazol-2-yl)-4-{[methyl-(4,4,4-trifluoro-3-hydroxy-butyl)-amino]-methyl}-benzamide Using 4-chloromethyl-benzoyl chloride and (rac)-1,1,1-trifluoro-4-methylamino-butan-2-ol the title compound was prepared using the general procedure C as white solid (89%), MS: m/e=539 (M+H⁺).

EXAMPLE 300

4-{[Ethyl-(2-methoxy-ethyl)-amino]-methyl}-N-(4-methoxy-7-morpholin-4-yl-benzothiazol-2-yl)-benzamide Using 4-chloromethyl-benzoyl chloride and (2-methoxy-ethyl)-ethyl-amine the title compound was prepared using the general procedure C as light brown solid (62%), MS: m/e=485 (M+H⁺).

EXAMPLE 301

4-{[(2-Ethoxy-ethyl)-ethyl-amino]-methyl}-N-(4-methoxy-7-morpholin-4-yl-benzothiazol-2-yl)-benzamide Using 4-chloromethyl-benzoyl chloride and (2-ethoxy-ethyl)-ethyl-amine the title compound was prepared using the general procedure C as light brown solid (66%), MS: m/e=499 (M+H⁺).

EXAMPLE 302

3-Fluoro-4-{[(2-methoxy-ethyl)-methyl-amino]-methyl}-N-(4-methoxy-7-morpholin-4-yl-benzothiazol-2-yl)-benzamide Using 3-fluoro-4-chloromethyl-benzoyl chloride and (2-methoxy-ethyl)-methyl-amine the title compound was prepared using the general procedure C as light brown solid (52%), MS: m/e=489 (M+H⁺).

EXAMPLE 303

4-{[Bis-(2-ethoxy-ethyl)-amino]-methyl}-N-(4-methoxy-7-morpholin-4-yl-benzothiazol-2-yl)-benzamide Using 4-chloromethyl-benzoyl chloride and bis-(2-ethoxy-ethyl)-amine the title compound was prepared using the general procedure C as light brown solid (49%), MS: m/e=543 (M+H⁺).

EXAMPLE 304

4-{[(2-Ethoxy-ethyl)-methyl-amino]-methyl}-N-(4-methoxy-7-morpholin-4-yl-benzothiazol-2-yl)-benzamide Using 4-chloromethyl-benzoyl chloride and (2-ethoxy-ethyl)-methyl-amine the title compound was prepared using the general procedure C as white solid (78%), MS: m/e=485 (M+H⁺).

EXAMPLE 305

N-(4-Methoxy-7-morpholin-4-yl-benzothiazol-2-yl)-4-(4-methoxy-piperidin-1-yl-methyl)-benzamide Using 4-chloromethyl-benzoyl chloride and 4-methoxy-piperidine the title compound was prepared using the general procedure C as white solid (33%), MS: m/e=497 (M+H⁺).

EXAMPLE 306

4-Diethylaminomethyl-N-(4-methoxy-7-morpholin-4-yl-benzothiazol-2-yl)-benzamide

Using 4-chloromethyl-benzoyl chloride and diethylamine the title compound was prepared using the general procedure C as light yellow solid (64%), MS: m/e=456 (M+H⁺).

EXAMPLE 307

4-[(2-Methoxy-ethylamino)-methyl]-N-(4-methoxy-7-morpholin-4-yl-benzothiazol-2-yl)-benzamide Using 4-chloromethyl-benzoyl chloride and 2-methoxy-ethylamine the title compound was prepared using the general procedure C as white solid (64%), MS: m/e=457 (M+H⁺).

EXAMPLE 308

N-(4-Methoxy-7-morpholin-4-yl-benzothiazol-2-yl)-4-(2-methyl-imidazol-1-yl-methyl)-benzamide Using 4-chloromethyl-benzoyl chloride and 2-methyl-1H-imidazole the title compound was prepared using the general procedure C as white solid (87%), MS: m/e=464 (M+H⁺).

EXAMPLE 309

N-(4-Methoxy-7-morpholin-4-yl-benzothiazol-2-yl)-4-(4-methyl-piperazin-1-yl-methyl)-benzamide Using 4-chloromethyl-benzoyl chloride and 1-methyl-piperazine the title compound was prepared using the general procedure C as white solid (78%), MS: m/e=482 (M+H⁺).

EXAMPLE 310

N-(4-Methoxy-7-morpholin-4-yl-benzothiazol-2-yl)-4-pyrrolidin-1-yl-methyl-benzamide Using 4-chloromethyl-benzoyl chloride and pyrrolidine the title compound was prepared using the general procedure C as white solid (81%), MS: m/e=454 (M+H⁺).

EXAMPLE 311

N-(4-Methoxy-7-morpholin-4-yl-benzothiazol-2-yl)-4-morpholin-4-yl-methyl-benzamide Using 4-chloromethyl-benzoyl chloride and morpholine the title compound was prepared using the general procedure C as white solid (83%), MS: m/e=469 (M+H⁺).

EXAMPLE 312

N-(4-Benzyloxy-7-morpholin-4-yl-benzothiazol-2-yl)-4-{[(2-methoxy-ethyl)-methyl-amino]-methyl}-benzamide Using N-(4-benzyloxy-7-morpholin-4-yl-benzothiazol-2-yl)-4-chloromethyl-benzamide and (2-methoxy-ethyl)-methyl-amine the title compound was prepared using the general procedure C as white solid (69%), MS: m/e=547 (M+H⁺).

EXAMPLE 313

N-(4-Methoxy-7-morpholin-4-yl-benzothiazol-2-yl)-4-{[methyl-(3,3,3-trifluoro-propyl)-amino]-methyl}-benzamide; hydrochloride N-(4-Methoxy-7-morpholin-4-yl-benzothiazol-2-yl)-4-methylaminomethyl-benzamide (100 mg, 0.24 mmol), triethylamine (35 mg, 0.34 mmol), potassium iodide (0.4 mg, 0.02 mmol) and 3,3,3-trifluoro-propylamine (48 mg, 0.27 mmol) were dissolved in ethanol (1ml) and dioxane (0.5 ml). The reaction vessel is sealed and heated to 90° C. for 18 h.

Workup and purification as described in the general procedure C afforded the title compound as light brown solid (28%), MS: m/e=509 (M+H$^+$).

EXAMPLE 314

4-(2-Methoxy-ethoxymethyl)-N-(4-methoxy-7-morpholin-4-yl-benzothiazol-2-yl)-benzamide 4-Chloromethyl-N-(4-methoxy-7-morpholin-4-yl-benzothiazol-2-yl)-benzamide (200 mg, 0.48 mmol) and sodium hydride (42 mg 55% dispersion in mineral oil, 0.96 mmol) were dissolved in 2-methoxy-ethanol (3.8 ml, 48 mmol) and stirred at ambient temperature for 18 h. Workup and, purification as described in the general procedure C afforded the title compound as white solid (70%), MS: m/e=458 (M+H$^+$).

EXAMPLE 315

4-Methoxymethyl-N-(4-methoxy-7-morpholin-4-yl-benzothiazol-2-yl)-benzamide

4-Chloromethyl-N-(4-methoxy-7-morpholin-4-yl-benzothiazol-2-yl)-benzamide (200 mg, 0.48 mmol) were suspended in THF (5 ml) and sodium methoxide (0.27 ml 5.4 M in MeOH, 1.4 mmol) were added at 0° C. The mixture was stirred at ambient temperature for 18 h. Workup and purification as described in the general procedure C afforded the title compound as light yellow solid (41%), MS: m/e=414 (M+H$^+$).

EXAMPLE 316

N-[4-Methoxy-7-(1-oxo-1λ$^4$-thiomorpholin-4-yl)-benzothiazol-2-yl]-benzamide

To a solution of N-(4-methoxy-7-thiomorpholin-4-yl-benzothiazol-2-yl)-benzamide (80 mg, 0.21 mmol) in [1,4] dioxane (3 ml) was added sodium periodate (89 mg, 0.42 mmol) and the mixture stirred for 20 h at ambient temperature. To this mixture water (10 ml) and dichloromethane (10 ml) were added, the phases were separated and the aqueous layer extracted twice with dichloromethane. The combined organic extracts were dryed with Na$_2$SO$_4$ and the solvent evaporated. Recrystallization from hot THF afforded the title compound as white solid (21%), MS: m/e=402 (M+H$^+$).

EXAMPLE 317

N-(4-Methoxy-7-thiomorpholin-4-yl-benzothiazol-2-yl)-benzamide

Following the general method of example 403 the title compound was synthesized from 3-(2-methoxy-5-thiomorpholin-4-yl-phenyl)-thiourea (synthesized from 4-bromo-1-methoxy-2-nitro-benzene and thiomorpholine as described for 1-benzoyl-3-(2-methoxy-5-morpholin-4-yl-phenyl)-thiourea) as a white solid (15%), MS: m/e=386 (M+H$^+$).

EXAMPLE 318

5-Methyl-thiophene-2-carboxylic acid (4-methoxy-7-piperazin-1-yl-benzothiazol-2-yl)-amide To a solution of 4-{4-methoxy-2-[(5-methyl-thiophene-2-carbonyl)-amino]-benzothiazol-7-yl}-piperazine-1-carboxylic acid benzyl ester (300 mg, 0.57 mmol) in dichloromethane (5 ml) were added boron trifluoride diethyl etherate (0.72 ml, 5.7 mmol) and ethane thiol (1.2 ml, 17 mmol) and the mixture stirred for 36 h. The volatile components are evaporated and the residue codistilled twice with toluene. The residue was dissolved in dichloromethane (25 ml), extracted with 1N aqueous sodium carbonate and the organic phase dryed with Na$_2$SO$_4$. Removal of the solvent and flash chromatography (silica, eluent CH$_2$Cl$_2$/MeOH/ aqu. NH$_4$OH 100:10:1) afforded the title compound as light yellow solid (58%), MS: m/e=389 (M+H$^+$).

EXAMPLE 319

5-Methyl-thiophene-2-carboxylic acid [7-(4-acetyl-piperazin-1-yl)-4-methoxy-benzothiazol-2-yl]-amide 5-Methyl-thiophene-2-carboxylic acid (4-methoxy-7-piperazin-1-yl-benzothiazol-2-yl)-amide (100 mg, 0.26 mmol) were suspended in DMF (2 ml) and treated with acetyl chloride (22 µl, 0.30 mmol) and pyridine (27 µl, 0.34 mmol) and the mixture stirred for 5 h at ambient temperature. Workup and purification as described in the general procedure C afforded the product as a white solid (55%), MS: m/e=431 (M+H$^+$).

EXAMPLE 320

4-{4-Methoxy-2-[(5-methyl-thiophene-2-carbonyl)-amino]-benzothiazol-7-yl}-piperazine-1-carboxylic acid methyl ester Using methyl chloroformate the tilte compound was synthesized as described for example 319 and obtained as white solid (26%), MS: m/e=447(M+H$^+$).

EXAMPLE 321

5-Methyl-thiophene-2-carboxylic acid [4-methoxy-7-(4-methyl-piperazin-1-yl)-benzothiazol-2-yl]-amide To a solution of 5-methyl-thiophene-2-carboxylic acid (4-methoxy-7-piperazin-1-yl-benzothiazol-2-yl)-amide (100 mg, 0.26 mmol) in methanol (8 ml) were added formic acid (100 µl, 2.6 mmol) and formaldehyde (23 µl, 0.31 mmol) and the mixture refluxed for 18 h. Workup and purification as described for 5-methyl-thiophene-2-carboxylic acid (4-methoxy-7-piperazin-1-yl-benzothiazol-2-yl)-amide afforded the product as light yellow powder (34%), MS: m/e=403(M+H$^+$).

EXAMPLE 322

5-Methyl-thiophene-2-carboxylic acid [7-(2,3-dihydro-1H-indol-6-yl)-4-methoxy-benzothiazol-2-yl]-amide The title compound was prepared from 5-methyl-thiophene-2-carboxylic acid (7-iodo-4-methoxy-benzothiazol-2-yl)-amide (100 mg, 0.23 mmol) and 6-iodo-2,3-dihydro-1H-indole using the general procedure B in Example 54 as light brown crystals (26%), MS: m/e=422 (M+H$^+$).

Intermediate 4-(4-Benzyloxy-3-nitro-phenyl)-morpholine

The title compound was prepared using morpholine and 1-benzyloxy-4-bromo-2-nitro-benzene (prepared from 4-bromo-2-nitro-anisol and benzyl bromide) using the general method of example "4-(4-methoxy-3-nitro-phenyl)-morpholine" as yellow solid (58%), MS: m/e=315(M+H$^+$).

Intermediate

2-Amino-4-morpholin-4-yl-phenol

Catalytic hydrogenation of 4-(4-benzyloxy-3-nitro-phenyl)-morpholine (5 g, 16 mmol) in dichloromethane (500 ml) and ethanol (500 ml) using palladium on carbon (500 mg, 10%) afforded the title compound as a grey solid (96%), MS: m/e=194(M$^+$).

EXAMPLE 323

N-(4-Hydroxy-7-morpholin-4-yl-benzothiazol-2-yl)-benzamide

The title compound was prepared using 2-amino-4-morpholin-4-yl-phenol as described for N-(4-methoxy-7-morpholin-4-yl-benzothiazol-2-yl)-benzamide and obtained as a light brown solid in 14% overall yield, MS: m/e=356 (M+H$^+$).

EXAMPLE 324

5-Methyl-thiophene-2-carboxylic acid [7-(3-dimethylamino-pyrrolidin-1-yl)-4-methoxy-benzothiazol-2-yl]-amide Using 5-methyl-thiophene-2-carbonyl chloride and 7-(3-dimethylamino-pyrrolidin-1-yl)-4-methoxy-benzothiazol-2-yl-amine the title compound was prepared using the general method of example 1 as yellow solid (90%), MS: m/e=417 (M+H$^+$).

Intermediate 7-(3-Dimethylamino-pyrrolidin-1-yl)-4-methoxy-benzothiazol-2-yl-amine Following the general method of example 403 the title compound was synthesized from [5-(3-dimethylamino-pyrrolidin-1-yl)-2-methoxy-phenyl]-thiourea (synthesized from 4-bromo-1-methoxy-2-nitro-benzene and dimethyl-pyrrolidin-3-yl-amine as described for (2-methoxy-5-morpholin-4-yl-phenyl)-thiourea) as a white solid (25%), MS: m/e=293 (M+H$^+$).

EXAMPLE 325

Tetrahydro-pyran-4-carboxylic acid (4-methoxy-7-morpholin-4-yl-benzothiazol-2-yl)-amide To a solution of 2-amino-4-methoxy-7-morpholin-4-yl-benzothiazol (100 mg, 0.4 mmol) in tetrahydrofurane (2 ml) were subsequently added N-ethyl-diisopropylamine (194 □1, 1.1 mmol) and tetrahydropyran-4-carbonyl chloride (77 mg, 0.52 mmol, dissolved in 0.5 ml tetrahydrofurane) and the mixture refluxed for 3 h. The mixture was then cooled to 0° C., methanol (0.4 ml) was added and the mixture slowly warmed to 20° C. Then the mixture was evaporated to dryness, dichloromethane was added (3 ml) and extracted with saturated aqueous sodium carbonate. After back extraction of the aqueous phase with two portions of dichloromethane (3 ml), the combined organic phases were dryed with Na$_2$SO$_4$ and the solvent evaporated. The crude product was was then chromatographed over SiO$_2$, eluting with CH$_2$Cl$_2$/MeOH 98:2, the product fractions were pooled and the solvent evaporated, to afford the title compound as a beige powder (142 mg, 76% yield), MS: m/e=378(M+H$^+$).

Following the General Method of Example 325 the Following Examples were Prepared

EXAMPLE 326

4-(4-Methoxy-7-morpholin-4-yl-benzothiazol-2-ylcarbamoyl)-piperidine-1-carboxylic acid tert-butyl ester Using 2-amino-4-methoxy-7-morpholin-4-yl-benzothiazol and 4-chlorocarbonyl-piperidine-1-carboxylic acid tert-butyl ester the title compound was obtained as a white solid (3%), MS: m/e=477(M+H$^+$).

EXAMPLE 327

1-Acetyl-piperidine-4-carboxylic acid (4-methoxy-7-morpholin-4-yl-benzothiazol-2-yl)-amide Using 2-amino-4-methoxy-7-morpholin-4-yl-benzothiazol and 1-acetyl-piperidine-4-carbonyl chloride the title compound was obtained as a white solid (22%), MS: m/e=419(M+H$^+$).

EXAMPLE 328

Piperidine-4-carboxylic acid (4-methoxy-7-morpholin-4-yl-benzothiazol-2-yl)-amide 4-(4-Methoxy-7-morpholin-4-yl-benzothiazol-2-ylcarbamoyl)-piperidine-1-carboxylic acid tert-butyl ester (95 mg, 0.2 mmol) were dissolved in trifluoroacetic acid (0.8 ml). After 1 h at room temperature, the mixture was evaporated to dryness. Purification as described for tetrahydro-pyran-4-carboxylic acid (4-methoxy-7-morpholin-4-yl-benzothiazol-2-yl)-amide afforded the title compound as a white solid (77%), MS: m/e=377(M+H$^+$).

General procedure E (ureas): The appropriate substituated 2-amino-benzothiazol (1 part, typically 500 mg) is dissolved in CH$_2$Cl$_2$ (100 parts) and treated with pyridine (3 parts) and phenyl chloroformate (1.25 parts). After stirring for 30 min at room temperature the mixture is refluxed for 2 h when the appropriate amine (5 equivalents) is added. After refluxing for 18 h, the mixture is evaporated to dryness, dissolved in CH$_2$Cl$_2$ and extracted with aqueous sodium carbonate. after back extraction of the aqueous phase with CH$_2$Cl$_2$ the combined organic layers were dried with Na$_2$SO$_4$, and evaporated to dryness. The product is isolated by flash chromatography (silica, eluent dichloromethane containing 2.5% methanol).

Following the General Method E the Compounds of Examples 329 to 367 and Example 370 were Prepared

EXAMPLE 329

4-[(4-Fluoro-phenylamino)-methyl]-piperidine-1-carboxylic acid (4-methoxy-7-morpholin-4-yl-benzothiazol-2-yl)-amide Using 4-methoxy-7-morpholin-4-yl-benzothiazol-2-ylamine and 4-[(4-fluoro-phenylamino)-methyl]-piperidine the title compound was obtained as off-white solid (25%). MS: m/e=522 (M+H$^+$).

EXAMPLE 330

4-Hydroxymethyl-4-phenyl-piperidine-1-carboxylic acid (4-methoxy-7-morpholin-4-yl-benzothiazol-2-yl)-amide Using 4-methoxy-7-morpholin-4-yl-benzothiazol-2-ylamine and 4-hydroxymethyl-4-phenyl-piperidine the title compound was obtained as light yellow solid (50%). MS: m/e=483 (M+H$^+$).

EXAMPLE 331

[1-(4-Methoxy-7-morpholin-4-yl-benzothiazol-2-yl-carbamoyl)-piperidin-4-ylmethyl]-carbamic acid methyl ester Using 4-methoxy-7-morpholin-4-yl-benzothiazol-2-yl-amine and piperidin-4-ylmethyl-carbamic acid methyl ester the title compound was obtained as white solid (81%). MS: m/e=464 (M+H$^+$).

EXAMPLE 332

4-Ethyl-piperidine-1-carboxylic acid (4-methoxy-7-morpholin-4-yl-benzothiazol-2-yl)-amide Using 4-methoxy-7-morpholin-4-yl-benzothiazol-2-ylamine and 4-ethyl-piperidine the title compound was obtained as white solid (26%). MS: m/e=406 (M+H$^+$).

EXAMPLE 333

4-(2-Oxo-pyrrolidin-1-ylmethyl)-piperidine-1-carboxylic acid (4-methoxy-7-morpholin-4-yl-benzothiazol-2-yl)-amide Using 4-methoxy-7-morpholin-4-yl-benzothiazol-2-yl-amine and 4-(2-oxo-pyrrolidin-1-ylmethyl)-piperidine the title compound was obtained as white solid (29%). MS: m/e=474 (M+H$^+$).

EXAMPLE 334

4-(2-Methoxy-ethyl)-piperazine-1-carboxylic acid (4-methoxy-7-morpholin-4-yl-benzothiazol-2-yl)-amide Using 4-methoxy-7-morpholin-4-yl-benzothiazol-2-yl-amine and 4-(2-methoxy-ethyl)-piperazine-the title compound was obtained as off-white solid (79%). MS: m/e=437 (M+H$^+$).

EXAMPLE 335

4-Cyanomethyl-piperidine-1-carboxylic acid (4-methoxy-7-morpholin-4-yl-benzothiazol-2-yl)-amide Using 4-methoxy-7-morpholin-4-yl-benzothiazol-2-yl-amine and 4-cyanomethyl-piperidine the title compound was obtained as white solid (46%). MS: m/e=416 (M+H$^+$).

EXAMPLE 336

[1-(4-Methoxy-7-morpholin-4-yl-benzothiazol-2-yl-carbamoyl)-piperidin-4-ylmethyl]-carbamic acid tert-butyl ester Using 4-methoxy-7-morpholin-4-yl-benzothiazol-2-yl-amine and piperidin-4-ylmethyl-carbamic acid tert-butyl ester the title compound was obtained as white solid (11%). MS: m/e=506 (M+H$^+$).

EXAMPLE 337

4-[2-(4-Chloro-phenyl)-tetrahydro-furan-2-yl]-piperidine-1-carboxylic acid (4-methoxy-7-morpholin-4-yl-benzothiazol-2-yl)-amide Using 4-methoxy-7-morpholin-4-yl-benzothiazol-2-yl-amine and 4-[2-(4-chloro-phenyl)-tetrahydro-furan-2-yl]-piperidine the title compound was obtained as white solid (43%). MS: m/e=557 (M+H$^+$).

EXAMPLE 338

4-(2-Hydroxy-ethyl)-piperidine-1-carboxylic acid (4-methoxy-7-morpholin-4-yl-benzothiazol-2-yl)-amide Using 4-methoxy-7-morpholin-4-yl-benzothiazol-2-yl-amine and 4-(2-hydroxy-ethyl)-piperidine the title compound was obtained as white solid (64%). MS: m/e=421 (M+H$^+$).

EXAMPLE 339

1-(2-Methoxy-ethyl)-3-(4-methoxy-7-morpholin-4-yl-benzothiazol-2-yl)-1-methyl-urea Using 4-methoxy-7-morpholin-4-yl-benzothiazol-2-yl-amine and (2-methoxy-ethyl)-methyl-amine the title compound was obtained as white solid (65%). MS: m/e=381 (M+H$^+$).

EXAMPLE 340

4-Methoxyacetyl-piperazine-1-carboxylic acid (4-methoxy-7-morpholin-4-yl-benzothiazol-2-yl)-amide Using 4-methoxy-7-morpholin-4-yl-benzothiazol-2-yl-amine and 4-methoxyacetyl-piperazine the title compound was obtained as beige solid (84%). MS: m/e=450 (M+H$^+$).

EXAMPLE 341

4-Methyl-piperidine-1-carboxylic acid (4-methoxy-7-morpholin-4-yl-benzothiazol-2-yl)-amide Using 4-methoxy-7-morpholin-4-yl-benzothiazol-2-yl-amine and 4-methyl-piperidine the title compound was obtained as white solid (47%) MS: m/e=391 (M+H$^+$).

EXAMPLE 342

4-Oxo-piperidine-1-carboxylic acid (4-methoxy-7-morpholin-4-yl-benzothiazol-2-yl)-amide Using 4-methoxy-7-morpholin-4-yl-benzothiazol-2-yl-amine and piperidin-4-one the title compound was obtained as white solid (38%). MS: m/e=391 (M+H$^+$).

EXAMPLE 343

4-Cyclopropyl-4-hydroxy-piperidine-1-carboxylic acid (4-methoxy-7-morpholin-4-yl-benzothiazol-2-yl)-amide Using 4-methoxy-7-morpholin-4-yl-benzothiazol-2-yl-amine and 4-cyclopropyl-4-hydroxy-piperidine the title compound was obtained as white solid (27%). MS: m/e=434 (M+H$^+$).

EXAMPLE 344

1,1-Dioxo-1$\lambda^6$-thiomorpholine-4-carboxylic acid (4-methoxy-7-morpholin-4-yl-benzothiazol-2-yl)-amide Using 4-methoxy-7-morpholin-4-yl-benzothiazol-2-yl-amine and thiomorpholine 1,1-dioxide the title compound was obtained as white solid (50% ). MS: m/e=427 (M+H$^+$).

EXAMPLE 345

4-Hydroxymethyl-piperidine-1-carboxylic acid (4-methoxy-7-morpholin-4-yl-benzothiazol-2-yl)-amide Using 4-methoxy-7-morpholin-4-yl-benzothiazol-2-ylamine and 4-hydroxymethyl-piperidine the title compound was obtained as white solid (31%). MS: m/e=407 (M+H$^+$).

EXAMPLE 346

Octahydro-quinoline-1-carboxylic acid (4-methoxy-7-morpholin-4-yl-benzothiazol-2-yl)-amide Using 4-methoxy-7-morpholin-4-yl-benzothiazol-2-yl-amine and octahydro-quinoline the title compound was obtained as white solid (79%). MS: m/e=432 (M+H$^+$).

EXAMPLE 347

2,3-Benzo-1,4-dioxa-8-aza-spiro[4,5]decane-8-carboxylic acid (4-methoxy-7-morpholin-4-yl-benzothiazol-2-yl)-amide Using 4-methoxy-7-morpholin-4-yl-benzothiazol-2-yl-amine and 2,3-benzo-1,4-dioxa-8-aza-spiro[4,5]decane the title compound was obtained as white solid (63%). MS: m/e=483 (M+H$^+$).

EXAMPLE 348

4-(4-Methoxy-7-morpholin-4-yl-benzothiazol-2-yl-carbamoyl)-piperazine-1-carboxylic acid methyl ester Using 4-methoxy-7-morpholin-4-yl-benzothiazol-2-yl-amine and piperazine-1-carboxylic acid methyl ester the title compound was obtained as white solid (90%). MS: m/e=436 (M+H$^+$).

EXAMPLE 349

Octahydro-isoquinoline-2-carboxylic acid (4-methoxy-7-morpholin-4-yl-benzothiazol-2-yl)-amide Using 4-methoxy-7-morpholin-4-yl-benzothiazol-2-yl-amine and octahydro-isoquinoline the title compound was obtained as white solid (53%). MS: m/e=432 (M+H$^+$).

EXAMPLE 350

3-Methyl-piperidine-1-carboxylic acid (4-methoxy-7-morpholin-4-yl-benzothiazol-2-yl)-amide Using 4-methoxy-7-morpholin-4-yl-benzothiazol-2-yl-amine and 3-methyl-piperidine the title compound was obtained as white solid (50%). MS: m/e=391 (M+H$^+$).

EXAMPLE 351

3-Hydroxymethyl-piperidine-1-carboxylic acid (4-methoxy-7-morpholin-4-yl-benzothiazol-2-yl)-amide Using 4-methoxy-7-morpholin-4-yl-benzothiazol-2-ylamine and 3-hydroxymethyl-piperidine the title compound was obtained as white solid (69%). MS: m/e=436 (M+H$^+$).

EXAMPLE 352

3,4-Benzo-1-oxa-8-aza-spiro[4.5]decane-8-carboxylic acid (4-methoxy-7-morpholin-4-yl-benzothiazol-2-yl-amide Using 4-methoxy-7-morpholin-4-yl-benzothiazol-2-yl-amine and 3,4-benzo-1-oxa-8-aza-spiro[4.5]decane the title compound was obtained as light yellow solid (67%). MS: m/e=481 (M+H$^+$).

EXAMPLE 353

4-(4-Methoxy-7-morpholin-4-yl-benzothiazol-2-yl-carbamoyl)-piperazine-1-carboxylic acid tert-butyl ester Using 4-methoxy-7-morpholin-4-yl-benzothiazol-2-yl-amine and piperazine-1-carboxylic acid tert-butyl ester the title compound was obtained as light yellow solid (66%). MS: m/e=478 (M+H$^+$).

EXAMPLE 354

4-Hydroxy-4-phenyl-piperidine-1-carboxylic acid (4-methoxy-7-morpholin-4-yl-benzothiazol-2-yl)-amide Using 4-methoxy-7-morpholin-4-yl-benzothiazol-2-yl-amine and 4-hydroxy-4-phenyl-piperidine the title compound was obtained as light yellow solid (36%). MS: m/e=469 (M+H$^+$).

EXAMPLE 355

4-Methyl-piperazine-1-carboxylic acid (4-methoxy-7-morpholin-4-yl-benzothiazol-2-yl)-amide Using 4-methoxy-7-morpholin-4-yl-benzothiazol-2-yl-amine and 4-methyl-piperazine the title compound was obtained as beige solid (20%). MS: m/e=392 (M+H$^+$).

EXAMPLE 356

4-Trifluoromethyl-piperidine-1-carboxylic acid (4-methoxy-7-morpholin-4-yl-benzothiazol-2-yl)-amide Using 4-methoxy-7-morpholin-4-yl-benzothiazol-2-yl-amine and 4-trifluoromethyl-piperidine the title compound was obtained as white solid (16%). MS: m/e=445 (M+H$^+$).

EXAMPLE 357

[1,4']Bipiperidinyl-1'-carboxylic acid (4-methoxy-7-morpholin-4-yl-benzothiazol-2-yl)-amide Using 4-methoxy-7-morpholin-4-yl-benzothiazol-2-yl-amine and [1,4']bipiperidinyl the title compound was obtained as white solid (35%). MS: m/e=461 (M+H$^+$).

EXAMPLE 358

3-(4-Methoxy-7-morpholin-4-yl-benzothiazol-2-yl)-1-(4-methoxy-phenyl)-1-methyl-urea Using 4-methoxy-7-morpholin-4-yl-benzothiazol-2-yl-amine and 4-methoxy-phenyl)-methyl-amine the title compound was obtained as light yellow solid (40%). MS: m/e=430 (M+H$^+$).

EXAMPLE 359

1,4-Dioxa-8-aza-spiro[4.5]decane-8-carboxylic acid (4-methoxy-7-morpholin-4-yl-benzothiazol-2-yl)-amide Using 4-methoxy-7-morpholin-4-yl-benzothiazol-2-yl-amine and 1,4-dioxa-8-aza-spiro[4,5]decane the title compound was obtained as beige solid (28%). MS: m/e=435 (M+H$^+$).

EXAMPLE 360

3,4-Dihydro-1H-isoquinoline-2-carboxylic acid (4-methoxy-7-morpholin-4-yl-benzothiazol-2-yl)-amide Using 4-methoxy-7-morpholin-4-yl-benzothiazol-2-yl-amine and 1,2,3,4-tetrahydro-isoquinoline the title compound was obtained as orange solid (63%). MS: m/e=425 (M+H$^+$).

EXAMPLE 361

3-(4-Methoxy-7-morpholin-4-yl-benzothiazol-2-yl)-1-methyl-1-phenyl-urea

Using 4-methoxy-7-morpholin-4-yl-benzothiazol-2-yl-amine and methyl-phenyl-amine the title compound was obtained as white solid (19%). MS: m/e=399 (M+H$^+$).

EXAMPLE 362

4-Hydroxy-piperidine-1-carboxylic acid (4-methoxy-7-morpholin-4-yl-benzothiazol-2-yl)-amide Using 4-methoxy-7-morpholin-4-yl-benzothiazol-2-yl-amine and piperidin-4-ol the title compound was obtained as yellow solid (50%). MS: m/e=393 (M+H$^+$).

EXAMPLE 363

4-Methoxy-piperidine-1-carboxylic acid (4-methoxy-7-morpholin-4-yl-benzothiazol-2-yl)-amide Using 4-methoxy-7-morpholin-4-yl-benzothiazol-2-yl-amine and 4-methoxy-piperidine the title compound was obtained as yellow solid (33%). MS: m/e=407 (M+H$^+$).

EXAMPLE 364

1-Oxo-1□$^4$-thiomorpholine-4-carboxylic acid (4-methoxy-7-morpholin-4-yl-benzothiazol-2-yl)-amide Using 4-methoxy-7-morpholin-4-yl-benzothiazol-2-yl-amine and thiomorpholine 1-oxide the title compound was obtained as white solid (87%). MS: m/e=411 (M+H$^+$).

EXAMPLE 365

Methanesulfonic acid 1-(4-methoxy-7-morpholin-4-yl-benzothiazol-2-ylcarbamoyl)-piperidin-4-yl-methyl ester 4-Hydroxymethyl-piperidine-1-carboxylic acid (4-methoxy-7-morpholin-4-yl-benzothiazol-2-yl)-amide (300 mg, 0.43 mmol) and N-ethyldiisopropylamine (95 μl, 0.56 mmol) were dissolved in CH$_2$Cl$_2$ (10 ml), methanesulfonyl chloride (36 μl, 0.47 mmol) was added and the mixture stirred at ambient temperature for 3 days. Purification as described in the general procedure E afforded the product as a white solid (34%).MS: m/e=466 (M+H$^+$).

EXAMPLE 366

Piperazine-1-carboxylic acid (4-methoxy-7-morpholin-4-yl-benzothiazol-2-yl)-amide Following the general method for piperidine-4-carboxylic acid (4-methoxy-7-morpholin-4-yl-benzothiazol-2-yl)-amide the title compound was prepared from 4-(4-methoxy-7-morpholin-4-yl-benzothiazol-2-yl-carbamoyl)-piperazine-1-carboxylic acid tert-butyl ester as a light yellow solid (99%).MS: m/e=378 (M+H$^+$).

EXAMPLE 367

4-Aminomethyl-piperidine-1-carboxylic acid (4-methoxy-7-morpholin-4-yl-benzothiazol-2-yl)-amide Following the general method for piperidine-4-carboxylic acid (4-methoxy-7-morpholin-4-yl-benzothiazol-2-yl)-amide the title compound was prepared from [1-(4-methoxy-7-morpholin-4-yl-benzothiazol-2-yl-carbamoyl)-piperidin-4-ylmethyl]-carbamic acid tert-butyl ester as a white solid (50%).MS: m/e=(M+H$^+$).

EXAMPLE 368

(4-Methoxy-7-morpholin-4-yl-benzothiazol-2-yl)-carbamic acid 2-methoxy-ethyl ester 4-Methoxy-7-morpholin-4-yl-benzothiazol-2-yl-amine (300 mg, 1.1 mmol) and N-ethyldiisopropylamine (0.56 ml, 3.4 mmol) were dissolved in tetrahydrofurane (11 ml) and 2-methoxyethyl chloroformate (0.19 ml, 1.4 mmol) were added over 5 min. Then the mixture was heated to 70° C. for 3 h. The mixture was cooled to room temperature, water added and extracted twice with ethyl acetate. The combined organic phases were dryed with Na$_2$SO$_4$ and evapprated to dryness. The title compound was obtained as off-white solid (52%). MS: m/e=368 (M+H$^+$).

EXAMPLE 369

[4-(4-Methoxy-7-morpholin-4-yl-benzothiazol-2-ylcarbamoyl)-benzyl]-methyl-carbamic acid methyl ester N-(4-Methoxy-7-morpholin-4-yl-benzothiazol-2-yl)-4-methylaminomethyl-benzamide (100 mg, 0.24 mmol), pyridine (29 μl, 0.36 mmol) and methyl chloroformate (24 μl, 0.32 mmol) were dissolved in dichloromethanel (5 ml) and stirred at ambient temperature for 18 h. Workup and purification as described in the general procedure C afforded the title compound as light yellow solid (66%), MS: m/e=471 (M+H$^+$).

EXAMPLE 370

1-Oxo-1λ$^4$-thiomorpholine-4-carboxylic acid (4-methoxy-7-piperidin-1-yl-benzothiazol-2-yl)-amide hydrochloride Using 4-methoxy-7-piperidin-1-yl-benzothiazol-2-ylamine and thiomorpholine 1-oxide the title compound was obtained as white solid in accordance with general procedure E (80%). MS: m/e=409 (M+H$^+$).

EXAMPLE 371

N-(4-Ethoxy-7-piperidin-1-yl-benzothiazol-2-yl)-4-fluoro-benzamide

The title compound was prepared strarting from 4-bromo-1-ethoxy-2-nitro-benzene and piperidine as described for 4-fluoro-N-(4-methoxy-7-morpholin-4-yl-benzothiazol-2-yl)-benzamide (Example 275) and obtained as a yellow solid in 10% overall yield, MS: m/e=400 (M+H$^+$).

EXAMPLE 372

4-Fluoro-N-(4-isopropoxy-7-piperidin-1-yl-benzothiazol-2-yl)-benzamide

The title compound was prepared strarting from 4-bromo-1-isopropoxy-2-nitro-benzene and piperidine as described for 4-fluoro-N-(4-methoxy-7-morpholin-4-yl-benzothiazol-2-yl)-benzamide (Example 275) and obtained as a light brown solid in 10% overall yield, MS: m/e=414 (M+H$^+$).

EXAMPLE 373

4-Fluoro-N-(4-methoxy-7-pyrrolidin-1-yl-benzothiazol-2-yl)-benzamide

The title compound was prepared strarting from 4-bromo-1-methoxy-2-nitro-benzene and pyrrolidine as described for 4-fluoro-N-(4-methoxy-7-morpholin-4-yl-benzothiazol-2-yl)-benzamide (Example 275) and obtained as a light brown solid in about 10% overall yield, MS: m/e=372 (M+H$^+$).

EXAMPLE 374

4-Fluoro-N-(4-methoxy-7-[1,4]oxazepan-4-yl-benzothiazol-2-yl)-benzamide

The title compound was prepared strarting from 4-bromo-1-methoxy-2-nitro-benzene and [1.4]Oxazepane as described for 4-fluoro-N-(4-methoxy-7-morpholin-4-yl-benzothiazol-2-yl)-benzamide (Example 275) and obtained as a light yellow solid in about 10% overall yield, MS: m/e=402 (M+H$^+$).

EXAMPLE 375

Morpholine-4-carboxylic acid [4-methoxy-7-(4-methoxy-piperidin-1-yl)-benzothiazol-2-yl]-amide The title compound was prepared strarting from 4-bromo-1-methoxy-2-nitro-benzene and 4-methoxy-piperidine as described for morpholine-4-carboxylic acid (4-methoxy-7-morpholin-4-yl-benzothiazol-2-yl)-amide (Example 136) and obtained as a light yellow solid in about 10% overall yield, MS: m/e=407 (M+H$^+$).

EXAMPLE 376

N-(7-Azepan-1-yl-4-methoxy-benzothiazol-2-yl)-4-nitro-benzamide

The title compound was prepared using 4-bromo-1-methoxy-2-nitro-benzene, azepane and 4-nitro-benzoyl chloride as described for 4-fluoro-N-(4-methoxy-7-morpholin-4-yl-benzothiazol-2-yl)-benzamide (Example 275) and obtained as a light yellow solid in about 10% overall yield, MS: m/e=427 (M+H$^+$).

EXAMPLE 377

Morpholine-4-carboxylic acid (4-methoxy-7-thiophen-3-yl-benzothiazol-2-yl)-amide The title compound was prepared strarting from 4-bromo-1-methoxy-2-nitro-benzene and trimethyl-thiophen-3-yl-stannane as described for morpholine-4-carboxylic acid (4-methoxy-7-phenyl-benzothiazol-2-yl)-amide (Example 157) and obtained as a light yellow solid in about 10% overall yield, MS: m/e=376 (M+H$^+$).

EXAMPLE 378

4-Fluoro-N-[4-methoxy-7-(2-methyl-imidazol-1-yl)-benzothiazol-2-yl]-benzamide

N-(7-Acetylamino-4-methoxy-benzothiazol-2-yl)-4-fluoro-benzamide (100 mg, 0.28 mmol) and Lawessons reagent (135 mg, 0.33 mmol) were dissolved in THF (10 ml) and stirred at ambient temperature for 18 h. Removal of the solvent and flash chromatoigraphy (silica, eluent CH$_2$Cl$_2$/2N aqu. NH$_3$ in MeOH 99:1 to 19:1) afforded a yellow solid which was dissolved in acetone (10 ml) and treated with iodomethane (19.8 mg, 1.4 mmol). After 3 h at ambient temperature the solvent was removed and after dissolution in ethanol (10 ml), aminoacetaldehyde dimethyl acetal (15 mg, 1.4 mmol) were added and the mixture stirred for 18 h at room temperature. The solvent was removed and the residue refluxed for 24 h in ethanol (10 ml) and conc. sulfuric acid (1 ml). The mixture was diluted with water (50 ml) and the pH adjusted to 8 with sodium carbonate. It was extracted three times with dichloromethane. The combined organic extracts were dryed with sodium sulfate and the solvebt removed. Flash chromatography (silica, eluent CH$_2$Cl$_2$/2N aqu. NH$_3$ in MeOH 96:4 to 9:1) afforded the title compound as brown solid, MS: m/e=383 (M+H$^+$).

EXAMPLE 379

2-Chloro-N-(4-methoxy-7-morpholin-4-yl-benzothiazol-2-yl)-6-methyl-isonicotinamide To a stirred suspension of 4-methoxy-7-morpholin-4-yl-benzothiazol-2-yl-amine (13.3 g, 50.1 mmol) in THF (700 ml) was added N-ethyldiisopropylamine (21.3 ml, 125 mmol). The mixture was then cooled to 5° C. and a solution of 2-chloro-6-methyl-isonicotinoyl chloride (10.5 g, 55.1 mmol) in dichloromethane (350 ml) was added dropwise over 2 hours. The reaction mixture was then stirred overnight at 20° C. To this mixture was added methanol (40 ml) and stirring continued for ten minutes. The mixture was then concentrated in vacuo and the residue partitioned between ethyl acetate and saturated sodium bicarbonate solution. The organic phases were then dried over Na$_2$SO$_4$ and the solvent evaporated. The crude product was then chromatographed over SiO$_2$ (Merck 230–400 mesh) eluting with CH$_2$Cl$_2$/MeOH (98:2), the product fractions were pooled and the solvent evaporated, to afford the title compound as a brown solid (16.0 g, 76% yield), MS: m/e=421 (M{$^{37}$Cl}+H$^+$), 419 (M{$^{35}$Cl}+H$^+$).

Following General Procedure E the Compounds of Examples 380 and 381 were Prepared

EXAMPLE 380

(4-Methoxy-7-morpholin-4-yl-benzothiazol-2-yl)-urea

Using 4-methoxy-7-morpholin-4-yl-benzothiazol-2-yl-amine and ammonia the title compound was obtained as a white solid (20%), MS: m/e=309 (M+H$^+$).

EXAMPLE 381

(4-Methoxy-7-morpholin-4-yl-benzothiazol-2-yl)-carbamic acid phenyl ester

Using 4-methoxy-7-morpholin-4-yl-benzothiazol-2-yl-amine and without adding an amine the title compound was obtained as a white foam (75%), MS: m/e=386 (M+H$^+$).

Following the General Method of Example 379 the Following Compound was Prepared

EXAMPLE 382

2-Chloro-N-(4-methoxy-7-morpholin-4-yl-benzothiazol-2-yl)-isonicotinamide

Using 4-methoxy-7-morpholin-4-yl-benzothiazol-2-yl-amine and 2-chloro-isonicotinoyl chloride the title compound was obtained as a brown solid (59%), MS: m/e=407 (M{$^{37}$Cl}+H$^+$), 405 (M{$^{35}$Cl}+H$^+$).

EXAMPLE 383

2-Iodo-N-(4-methoxy-7-morpholin-4-yl-benzothiazol-2-yl)-6-methyl-isonicotinamide To a stirred suspension of 2-chloro-N-(4-methoxy-7-morpholin-4-yl-benzothiazol-2-yl)-6-methyl-isonicotinamide (1.00 g, 2.39 mmol) in ethyl methyl ketone (10 ml) and dioxane (20 ml) were added sodium iodide (2.0 g, 13.3 mmol) and hydriodic acid (0.95 ml, 7.2 mmol, 57% aqueous). The mixture was then heated at 100° C. for 96 hours. The mixture was then concentrated in vacuo and the residue resuspended in dichloromethane and washed sequentially with saturated sodium bicarbonate solution, 0.1 M sodium thiosulfate solution, and saturated brine. The organic phase was then dried over Na$_2$SO$_4$ and the solvent evaporated. The crude product was then chromatographed over SiO$_2$ (Merck 230–400 mesh) eluting with CH$_2$Cl$_2$MeOH (99:1 then 98:2), the product fractions were pooled and the solvent evaporated, to afford the title compound as a brown solid (80 mg, 7% yield), MS: m/e=511 (M+H$^+$).

Following General Procedure E the Compounds of Examples 384 and 385 were Prepared

EXAMPLE 384

1-Benzyl-3-(4-methoxy-7-morpholin-4-yl-benzothiazol-2-yl)-1-methyl-urea

Using 4-methoxy-7-morpholin-4-yl-benzothiazol-2-yl-amine and N-benzylmethylamine the title compound was obtained as an off-white solid (94%), MS: m/e=413 (M+H$^+$).

EXAMPLE 385

3-(4-Methoxy-7-morpholin-4-yl-benzothiazol-2-yl)-1-methyl-1-phenethyl-urea

Using 4-methoxy-7-morpholin-4-yl-benzothiazol-2-ylamine and N-methyl-2-phenylethylamine the title compound was obtained as an off-white solid (53%), MS: m/e=427 (M+H$^+$).

Following the General Method of Example 379 the Compounds of Examples 386 to 391 were Prepared

EXAMPLE 386

N-(4-Methoxy-7-morpholin-4-yl-benzothiazol-2-yl)-2-phenyl-acetamide

Using 4-methoxy-7-morpholin-4-yl-benzothiazol-2-yl-amine and phenylacetyl chloride the title compound was obtained as a light yellow solid (37%), MS: m/e=384 (M+H$^+$).

EXAMPLE 387

N-(4-Methoxy-7-morpholin-4-yl-benzothiazol-2-yl)-propionamide

Using 4-methoxy-7-morpholin-4-yl-benzothiazol-2-yl-amine and propionyl chloride the title compound was obtained as a light yellow solid (5%), MS: m/e=322 (M+H$^+$).

EXAMPLE 388

2-Methoxy-N-(4-methoxy-7-morpholin-4-yl-benzothiazol-2-yl)-acetamide

Using 4-methoxy-7-morpholin-4-yl-benzothiazol-2-yl-amine and methoxyacetyl chloride the title compound was obtained as a light yellow solid (37%), MS: m/e=338 (M+H$^+$).

EXAMPLE 389

Pentanoic acid (4-methoxy-7-morpholin-4-yl-benzothiazol-2-yl)-amide

Using 4-methoxy-7-morpholin-4-yl-benzothiazol-2-yl-amine and valeroyl chloride the title compound was obtained as a light yellow solid (48%), MS: m/e=350 (M+H$^+$).

EXAMPLE 390

N-(4-Methoxy-7-morpholin-4-yl-benzothiazol-2-yl)-isobutyramide

Using 4-methoxy-7-morpholin-4-yl-benzothiazol-2-yl-amine and isobutyryl chloride the title compound was obtained as a light yellow solid (8%), MS: m/e=336 (M+H$^+$).

EXAMPLE 391

N-(4-Methoxy-7-morpholin-4-yl-benzothiazol-2-yl)-3-phenyl-propionamide

Using 4-methoxy-7-morpholin-4-yl-benzothiazol-2-yl-amine and 3-phenylpropionyl chloride the title compound was obtained as a light yellow solid (3%), MS: m/e=398 (M+H$^+$).

Following General Procedure E the Compounds of Examples 392 to 396 were Prepared

EXAMPLE 392

1-Benzyl-3-(4-methoxy-7-morpholin-4-yl-benzothiazol-2-yl)-urea

Using 4-methoxy-7-morpholin-4-yl-benzothiazol-2-yl-amine and benzylamine the title compound was obtained as an off-white solid (99%), MS: m/e=399 (M+H$^+$).

EXAMPLE 393

1-(4-Methoxy-7-morpholin-4-yl-benzothiazol-2-yl)-3-phenethyl-urea

Using 4-methoxy-7-morpholin-4-yl-benzothiazol-2-yl-amine and 2-phenylethylamine the title compound was obtained as an off-white solid (87%), MS: m/e=413 (M+H$^+$).

EXAMPLE 394

1-(2-Methoxy-ethyl)-3-(4-methoxy-7-morpholin-4-yl-benzothiazol-2-yl)-urea

Using 4-methoxy-7-morpholin-4-yl-benzothiazol-2-yl-amine and 2-methoxyethylamine the title compound was obtained as an off-white solid (80%), MS: m/e=367 (M+H$^+$).

EXAMPLE 395

1-(2-Dimethylamino-ethyl)-3-(4-methoxy-7-morpholin-4-yl-benzothiazol-2-yl)-1-methyl-urea Using 4-methoxy-7-morpholin-4-yl-benzothiazol-2-yl-amine and N,N,N'-trimethylethylenediamine the title compound was obtained as an off-white solid (61%), MS: m/e=394 (M+H$^+$).

EXAMPLE 396

1-(2-Dimethylamino-ethyl)-3-(4-methoxy-7-morpholin-4-yl-benzothiazol-2-yl)-urea

Using 4-methoxy-7-morpholin-4-yl-benzothiazol-2-yl-amine and 2-dimethylamino-ethylamine the title compound was obtained as an off-white solid (79%), MS: m/e=380 (M+H$^+$).

Following the General Method of Example 379 the Compound of Example 397 was Prepared

EXAMPLE 397

4-Dimethylamino-N-(4-methoxy-7-morpholin-4-yl-benzothiazol-2-yl)-butyramide

Using 4-methoxy-7-morpholin-4-yl-benzothiazol-2-yl-amine and 4-dimethylamino-butyryl chloride the title compound was obtained as a light yellow solid (10%), MS: m/e=379 (M+H$^+$).

Preparation of intermediates for examples 1 to 187

EXAMPLE 398

(7-Iodo-4-methoxy-benzothiazol-2-yl)-carbamic acid methyl ester (4-Methoxy-benzothiazol-2-yl)-carbamic acid methyl ester (31.0 g, 130 mmol) and sodium acetate (32.3 g, 394 mmol) are dissolved in 400 ml of glacial acetic acid and slowly treated with iodine monochloride (13.5 ml, 264 mmol) at 0° C. The reaction mixture is then slowly warmed to room temperature and stirred for 15 hours. After addition of water (1.3 l), the formed precipitate is filtered off and washed with water. The filter cake is then dissolved in a minimal amount of tetrahydrofurane (about 150 ml) and decolorized with 1M aqueous sodium thiosulfate. The product is precipitated by the addition of water (about 2.0 l), filtered off and dried at 60° C. for 12 hours. 42.3 g (89%) white solid. MS: m/e=364 (M$^+$).

EXAMPLE 399

(4-Methoxy-benzothiazol-2-yl)-carbamic acid methyl ester

2-Amino-4-methoxybenzothiazol (23.6 g, 131 mmol) and pyridine (12.6 ml, 157 mmol) in dichloromethane (230 ml) are slowly treated with methyl chloroformate (10.6 ml, 137 mmol) at 0° C. After 10 minutes, further methyl chloroformate (1.0 ml, 13 mmol) and pyridine (1.0 ml, 12 mmol) are added. After 10 minutes, the mixture is poured into 200 ml 1M aqueous hydrochloric acid, the organic layer is separated, diluted with dichloromethane (250 ml) and washed with brine (50 ml). The organic phase is dried and the solvent evaporated in vacuo. 31.0 g (99.4%) white solid. MS: m/e=238 (M+H$^+$).

EXAMPLE 400

(4-Methoxy-7-phenyl-benzoyhiazol-2-yl)-carbamic acid tert-butyl ester

To a suspension of 2-amino-4-methoxy-7-phenyl-benzothiazole (1.0 g, 3.9 mmol) in THF (50 ml) was added di(tert-butoxycarbonyl)-anhydride (BOC)$_2$O and DMAP (47 mg, 0.04 mmol) and the mixture stirred for 1 h a r.t., followed by 3 h at 60° C. After cooling the solvent was evaporated and the residue chromatographed over SiO$_2$ (Merck 230–400 mesh) eluting with a gradient of cyclohexane/EtOAc (10% to 50% EtOAc), after pooling the product fractons and evaporation of the solvents the title compound was obtained as a white foam (1.1 g, 79% yield), MS: m/e=356 (M$^+$).

EXAMPLE 401

(4-Methoxy-benzothiazol-2-yl)-carbamic acid tert-butyl ester

Using 2-amino-4-methoxy-benzothiazole the title compound was obtained as a white solid (60% yield), MS: m/e=281.2 (M+H$^+$).

EXAMPLE 402

2-Amino-4-methoxy-7-phenyl-benzothiazole

The title compound was prepared from 3-amino-4-methoxy-biphenyl, according to the patent literature N-(Benzothiazol-2-yl)oxamic acid derivatives. W. Winter, M. Thiel, A. Roesch and O. H. Wilhelms, German Patent, DE 2656468, 1978. and is obtained as a white solid, MS: m/e=256 (M$^+$), mp. 207–208° C.

EXAMPLE 403

4-Methoxy-7-phenoxy-benzothiazol-2-yl-amine

To a suspension of 2-methoxy-5-phenoxy-phenyl)-thiourea (8.25 g, 30 mmol) in CHCl$_3$ (70 ml) was added bromine (4.8 g, 30 mmol) in CHCl$_3$ (10 ml) dropwise over 10 min. The mixture was then heated to reflux for 3 h, then cooled to r.t., the solvent was evaporated and the residue crystallised from MeOH/ether (1:4). The filter cake was then further washed with saturated aqueous NaHSO$_3$ solution /water (1:1), (100 ml), water (200 ml), 1N NaOH (60 ml), then water (100 ml), and finally ether (100 ml). The solid material thus obtained was dried under vacuum (0.05 mmHg, 60° C.) to afford the title compoud as a white solid (6.7 g, 82% yield), MS: m/e=272.1 (M$^+$).

Following the General Method of Example 403, the Compounds of Examples 404 to 409 were Prepared

EXAMPLE 404

2-Amino-4-methoxy-benzothiazole-7-carboxylic acid methyl ester

Using 4-methoxy-3-thioureido-benzoic acid methyl ester the title compound was obtained as a white solid (55% yield), MS: m/e=239.2 (M+H$^+$).

EXAMPLE 405

7-Bromo-4-methoxy-benzothiazole-2-yl-amine

Using (5-bromo-2-methoxy-phenyl)-thiourea the title compound was obtained as a white solid (46% yield), MS: m/e=258 (M$^+$).

EXAMPLE 406

7-tert-Butyl-4-methoxy-benzothiazole-2-yl-amine

Using (5-tert-butyl-2-methoxy-phenyl)-thiourea the title compound was obtained as a white solid (79% yield), MS: m/e=238.1 (M$^+$).

EXAMPLE 407

7-Acetylamino-4-methoxy-benzothiazole-2-yl-amine

Using (5-acetylamino-2-methoxy-phenyl)-thiourea the title compound was obtained as a purple solid (49% yield), MS: m/e=238.2 (M+H$^+$.)

EXAMPLE 408

4-methoxy-7-(1H-tetrazol-5-yl)-benzothiazol-2-yl-amine

Using 2-methoxy-5-(1H-tetrazol-5-yl)-phenyl]-thiourea the title compound was obtained as a tan solid (54% yield), MS: m/e=248.2 (M$^+$)

EXAMPLE 409

(4-Methoxy-7-phenyl-benzothiazol-2-yl)-methyl-amine

Using (4-methoxy-biphenyl-3-yl)-thiourea the title compound was obtained as a white solid (71% yield), MS: m/e=270.1 (M$^+$).

EXAMPLE 410

5-Methoxy-7-phenyl-benzothiazol-2-yl-amine (5-Methoxy-biphenyl-3-yl)-thiourea (109 mg, 0.42 mmol) in chloroform (2 ml) are treated with bromine (22 μl) and the mixture heated to 61° C. for 5 hours. After removal of the volatile components in vacuo, the product (93 g, 86%) is isolated by flash chromatography (silica, eluent ethyl acetate/cyclohexane 2:1 to 5:1) as beige solid. The regiochemistry of the cyclization was checked by transfer-NOE measurements. MS: m/e=256 (M+).

EXAMPLE 411

2-Amino-4,5-dimethoxybanzothiazol

2-Amino-4,5-dimethoxybanzothiazol is synthesized starting from 2,3-dimethoxyaniline (1.0 g, 6.5 mmol) in the same manner as described for 5-methoxy-7-phenyl-benzothiazol-2-yl-amine in 72% total yield over three steps. MS: m/e=210 (M+).

EXAMPLE 412

6-Bromo-4-trifluoromethoxy-benzothiazol-2-yl-amine

4-Bromo-2-trifluoromethoxy)aniline (768 mg, 3 mmol) and potassium thiocyanate (875 mg, 9 mmol) are dissolved in acetic acid (5 ml) and at 0° C., bromine (0.19 ml, 3.6 mmol) are slowly added. After stirring for 1 h, acetic acid (2 ml) are added and the mixture heated to 100° C. for 3 h. After cooling to room temperature, aqueous sodium hydroxide (10M, 25 ml) is added and the mixture extracted three times with ethyl acetate. The combined organic layers were wasged with brine, dried and the solvent removed in vacuo. Flash chromatography (silica, eluent ethyl acetate/cyclohexane 1:4) and final recrystallization from ethyl acetate/cyclohexane affords the product as white solid. 170 mg (18%). MS: m/e=315 (M+H+).

EXAMPLE 413

4-Methoxy-7-morpholin-4-yl-benzothiazol-2-yl-amine (2-Methoxy-5-morpholin-4-yl-phenyl)-thiourea (5.0 g, 19 mmol) in chloroform (130 ml) are treated with bromine (960 □l) and the mixture refluxed for 18 hours. After removal of the volatile components in vacuo, the product is recrystallized from THF (2.8 g, 57%). MS: m/e=266 (M+).

EXAMPLE 414

7- Benzyloxy -4-methoxy-benzothiazole-2-yl-amine

Synthesized starting from (5-Benzyloxy-2-methoxy-phenyl)-thiourea in the same manner as described for 5-methoxy-7-phenyl-benzothiazol-2-yl-amine in 82% yield as a beige solid. Mp: 165° C. (dec.).

EXAMPLE 415

4-Trifluoromethoxy-benzothiazol-2-yl-amine

6-Bromo-4-trifluoromethoxy-benzothiazol-2-ylamine (157 mg, 0.50 mg), triethylamine (0.21 ml, 1.5 mmol) and palladium on carbon (10%, 15 mg) are suspended in ethanol (12 ml) and hydrogenated at atmospheric pressure for 96 h. The catalyst was filtered off and the solution evaporated to dryness. The residue was dissolved in ethyl acetate, washed three times with water, dried and the solvent removed in vacuo. The product is obtained as brown solid (85 mg, 73%). MS: m/e=235 (M+H+).

EXAMPLE 416

2-Amino-4-methoxy-benzothiazole-7-carbaldehyde

Using (5-Formyl-2-methoxy-phenyl)-thiourea the title compound was synthesised as described for 4-methoxy-7-phenoxy-benzothiazol-2-yl-amine and obtained as a beige solid (70% yield), MS: m/e=208.0 (M+).

EXAMPLE 417

4-Methoxy-7-morpholin-4-ylmethyl-benzothiazol-2-yl-amine

To a suspension of 2-amino-4-methoxy-benzothiazole-7-carbaldehyde (440 mg, 2.1 mmol) in THF (100 ml) was added morpholine (276 mg, 3.2 mmol), acetic acid (190 mg, 3.2 mmol) followed by NaBH(OAc)$_3$ (672 mg, 3.2 mmol). This mixture was stirred vigorously at 20° C. for 48 hours, after which time water (50 ml) and 5% NaHCO$_3$ solution (50 ml) were added and the mixture agitated vigorously. After separating the organic and aqueous layers, the aqueous phase was extracted with EtOAc (50 ml) and the combined organic phase was washed with saturated NaCl solution (100 ml) then dried with Na$_2$SO$_4$, filtered and evaporated. The solid residue was suspended in ether (20 ml) and filtered then the filter cake was washed with ether (10 ml), and dried under vacuum (0.05 mmHg, 50° C.) to afford the title compound as a yellow solid (430 mg, 73% yield), MS: m/e=280.2 (M+).

EXAMPLE 418

2-Chloro-4-methoxy-7-phenyl-benzothiazole

To a suspension of 2-amino-4-methoxy-7-phenyl-benzothiazole (5.1 g, 20 mmol) in ethylene glycol (75 ml) were added hydrazine monohydrate (4 g, 80 mmol) and hydrazine dihydrochloride (4.2 g, 40 mmol) and the suspension was heated for 18 h at 140° C. After cooling to r.t. the suspension was filtered, then the filter cake was washed with water (200 ml) followed by ether (100 ml), and dried under vacuum (0.05 mmHg, 70° C.) to afford 2-hydrzino-4-methoxy-7-phenyl-benzothiazole as a white solid (5.2 g, 96% yield). The 2-hydrzino-4-methoxy-7-phenyl-benzothiazole (4.5 g, 16.6 mmol) was then added in portions over 20 min. to stirred neat thionyl chloride (12 ml, 165 mmol), the mixture was then heated to 50° C. for 2 h to complete the reaction. The reaction mixture was then cooled and poured on to ice/water (300 ml) and stirrd for 20 min. at 0–10° C. The whole mixture was then filtered and the filter cake waas washed with water (100 ml). The filter cake was then dissolved in CH$_2$Cl$_2$ (250 ml) and washed with saturated NaCl solution. The organic phase was dried with Na$_2$SO$_4$ filtered and evaporaterd to affoed a red oil which was chromatographed over SiO$_2$ (Merck 230–400 mesh) eluting with CH$_2$Cl$_2$. The product fractions were pooled and evaporated to afford the title compound as a brown solid (4.24 g, 93% yield), MS: m/e=275.0 (M+).

Lit: *Synth. Commun.*, 1992, 2769–80.

EXAMPLE 419

4-(Morpholine-4-sulfonyl)-benzoic acid

To a solution of 4-(chlorosulfonyl)-benzoic acid (0.5 g, 2.2 mmol) in THF (20 ml) was added morpholine (0.434 ml, 5 mmol) dropwise over 5 min, and this mixture stirred at r.t. for 1 h. Water (50 ml) was then addedand the mixture agitated, the phases were separated and the aqueous phase extracted with EtOAc (2×50 ml). The combined organic phases were washed with satd. aq. NaCl solution, dried, filtered and evaporated. The residue was chromatographed over $SiO_2$ (Merck 230–400 mesh) eluting with a $CHCl_3$/ (acetone+10% $HCO_2H$) (9:1), the product fractions were pooled, evaporated and dried in vacuo (0.05 mmHg, 50° C.) to afford the title compound as a beige solid (270 mg, 20% yield), MS: m/e=271 ($M^+$).

Following the General Method of Example 419, the Compounds of Examples 420 to 422 were Prepared

EXAMPLE 420

4-Dipropylsulfamoyl-benzoic acid

Using dipropylamine the title compound was obtained as a beige solid, MS: m/e=285 ($M^+$).

EXAMPLE 421

4-Ethylsulfamoyl-benzoic acid

Using ethylamine the title compound was obtained as a white solid (85% yield), MS: m/e=228.1 $(M–H)^-$.

EXAMPLE 422

4-Diethylsulfamoyl-benzoic acid

Using diethylamine the title compound was obtained as a white solid (44% yield), MS: m/e=257 ($M^+$).

EXAMPLE 423

2-(1,1-Dioxo-thiomorpholin-4-yl)-ethylamine

The title compound was prepared according to the following patent literature: W. R. Baker, S. A. Boyd, A. K. L Fung, H. H Stein, J. F. Denissen, C. W. Hutchins and S. H. Rosenberg, WO 9203429 (1992).

EXAMPLE 424

Methyl-(6-methyl-pyridin-3-ylmethyl)-amine

To a suspension of $LiAlH_4$ in THF (120 ml) at 10° C. was added a solution of methyl-6-methyl nicotinate (12 g, 79 mmol) in THF (80 ml) dropwise with cooling over 45 min. After stirring 1.5 h at 20° C., a mixture of THF/water (4:1) 60 ml was added to the reaction over 30 min. at 0° C., $Na_2SO_4$ (50 g) was then added dirctly to the reaction mixture which was stirred vigorously, then filtered and the THF evaporated in vacuo. The residue was chromatographed over $SiO_2$ (Merck 230–400 mesh) eluting with a gradient of $CH_2Cl_2$/MeOH (97:3 to 9:1), affording a colourless oil (7.5 g, 77% yield). This material was dissolved in $CHCl_3$ (100 ml) and treated dropwise with thionyl chloride (17.2 ml, 237 mmol) stirred at 5° C. to 20° C. over 16 h. The solvents were then removed in vacuo and the residue partitioned between $CH_2C_2$ (100 ml) and aq. 5% $NaHCO_3$ (100 ml), the aqueous phase was further extracted with $CH_2Cl_2$ (2×50 ml) and the combined extracts washed with satd. aq. NaCl solution (1×50 ml), then dried and the solvent evaporated in vacuo. The resulting red oil was dissolved in EtOH (80 ml) cooled to 0° C. and treated with 33% methylamine/EtOH (50 ml) dropwise over 1 h, then the mixture was stirred to 20° C. over 3 h. After evaporation of all the solvents the residue was partitioned between $CH_2Cl_2$ and water (100 ml ea.), the aqueous phase was further extracted with $CH_2Cl_2$ (2×100 ml), dried ($Na_2SO_4$), filtered and the solvent evaporated in vacuo. The brown oily residue was then distilled under high vacuum (0.1 mm Hg, 68–70° C.) over a Vigreux column to afford the title compound as a pale yellow liquid (6.03 g, 75% yield), MS: m/e=136.1($M^+$).

Lit: *J. Med. Chem.*, 1996, 5053–63.

Following the General Method of Example 424, the Compounds of Examples 425 to 4266 were Prepared

EXAMPLE 425

Methyl-pyridin-2-yl-methyl-amine

Using 2-chloromethyl-pyridine hydrochloride salt and 33% methylamine/EtOH the title compound was obtained as a colourless liquid (0.1 mm Hg, 47–48° C.) (20% yield), MS: m/e=93.1 ($M—NHCH_3$).

EXAMPLE 426

Methyl-pyridin-4-ylmethyl-amine

Using 4-chloromethyl-pyridine hydrochloride salt and 33% methylamine/EtOH the title compound was obtained as a colourless liquid (0.1 mm Hg, 60–62° C.) (79% yield), MS: m/e=122.1 ($M^+$).

Preparation of intermediates for examples 188 to 208

EXAMPLE 427

2-Methoxy-5-phenoxy-phenyl)-thiourea

To a solution of 2-methoxy-5-phenoxy-aniline (9.9 g, 46 mmol) in acetone (60 ml) was added benzoylisothiocyanate (9 g, 55 mmol) and the mixture heated to reflux (56° C.) for 4 h. After cooling to r.t., the solvent was evaporated and the oily orange residue was precipitated from ether (20 ml) under ultrasonnication, the solid was then washed on the filter with ether/nHexane (1:3) (50 ml). The solid thus obtained was further dried under vacuum (0.05 mmHg, 50° C.) to afford the benzoylated thiourea as a beige solid (17.2 g, 99%, yield). Fresh sodium methoxide (14.5 g, 38 mmol) was then added to a suspension of the benzoylated thiourea (14.5 g, 38 mmol) in methanol (70 ml) and this mixture stirred for 1 h at r.t. Water was then added (210 ml) and the precipitated solid was collected, then washed on the filter with water (100 ml), followed by ether (100 ml), then dried under vacuum (0.05 mmHg, 50° C.) to afford the title compound as a white solid (8.5 g, 81% yield), MS: m/e= 274.1 ($M^+$).

Following the General Method of Example 427 the Compounds of Examples 428 to 433 were Prepared

EXAMPLE 428

(5-tert-Butyl-2-methoxy-phenyl)-thiourea

Using 4-tert-butyl-2-methoxy-aniline the title compound was obtained as a white solid (79% yield), MS: m/e=238.1 ($M^+$).

EXAMPLE 429

(5-Acetylamino-2-methoxy-phenyl)-thiourea

Using 3-amino-4-methoxyacetanilide the title compound was obtained as a grey solid (69% yield), MS: m/e=240.3 ($M+H^+$).

EXAMPLE 430

4-Methoxy-3-thioureido-benzoic acid methyl ester

Using 3-Amino-4-methoxy-benzoic acid methyl ester the title compound was obtained as a tan solid (78% yield), MS: m/e=240.0 (M$^+$).

EXAMPLE 431

(5-Bromo-2-methoxy-phenyl)-thiourea

Using 5-bromo-2-methoxy-aniline the title compound was obtained as a white solid (88% yield), MS: m/e=260 (M$^+$).

EXAMPLE 432

2-methoxy-5-(1H-tetrazol-5-yl)-phenyl]-thiourea

Using 2-methoxy-5-(1H-tetrazol-5-yl)-aniline the title compound was obtained as a tan solid (92% yield), MS: m/e=250.1 (M$^+$).

EXAMPLE 433

1-(4-Methoxy-biphenyl-3-yl)-3-methyl-thiourea

Using 4-methoxy-biphenyl-3-ylamine and N-methyl-isothiocyanate the title compound was directly obtained as a white solid (96% yield), MS: m/e=273.2 (M+H$^+$).

EXAMPLE 434

(5-Methoxy-biphenyl-3-yl)-thiourea

1-Benzoyl-3-(5-methoxy-biphenyl-3-yl)-thiourea (183 mg, 0.51 mmol) in methanol (5 ml) are treated with sodium methoxide (5.4M in methanol, 0.14 ml) and the formed precipitate is filtered off. Washing with methanol yields the product (115 mg, 88%) as off-white powder. MS: m/e=258 (M$^+$).

EXAMPLE 435

1-Benzoyl-3-(5-methoxy-biphenyl-3-yl)-thiourea

5-Methoxy-biphenyl-3-ylamine (129 mg, 0.65 mmol) are dissolved in acetone (5 ml) and slowly treated with a solution of benzoyl isothiocyanate (0.096 ml, 0.71 mmol) in acetone (2 ml). After stirring at ambient temperature for 18 h, the solvent is removed in vacuo and the residue crystallized from hexane. The product (203 mg, 86%) is obtained as colorless crystals. Mp 149° C.

EXAMPLE 436

(2-Methoxy-5-morpholin-4-yl-phenyl)-thiourea

1-Benzoyl-3-(2-methoxy-5-morpholin-4-yl-phenyl)-thiourea (8.0 g, 21 mmol), suspended in methanol (260 ml), are treated with 6 ml sodium methanolate (5.4M in methanol) and the mixture stirred until a white precipitate forms. The mixture is concentrated in vacuo, the crystals are isolated by filtration and washed with methanol and hexane (5.0 g 86%). MS: m/e=268 (M$^+$).

EXAMPLE 437

1-Benzoyl-3-(2-methoxy-5-morpholin-4-yl-phenyl)-thiourea

To a solution of 2-methoxy-5-morpholin-4-yl-phenylamine (4.6 g, 22 mmol) in acetone (140 ml) is added a solution of benzoyl isithiocyanate (3.4 ml, 25 mmol) in acetone (80 ml) and the reaction mixture is stirred for further 30 min at ambient temperature. After removal of the volatile components in vacuo, the product is isolated by flash chromatography (silica, eluent ethyl acetate/n-hexane 1:4, then 1:2) as a yellow solid (8.0 g, 97%). MS: m/e=272 (M$^+$).

EXAMPLE 438

(5-Benzyloxy-2-methoxy-phenyl)-thiourea

Synthesized from 5-benzyloxy-2-methoxy-aniline as described for example 427 in 80% overall yield. Obtained as white crystals. M.p. 130° C. (dec.).

EXAMPLE 439

(5-Formyl-2-methoxy-phenyl)-thiourea

To a solution of 2-(4-methoxy-3-nitro-phenyl)-[1,3] dioxolane (13 g, 57.7 mmol) in MeOH (400 ml) was added Adams catalyst-Pt(O$_2$) (700 mg) and the mixture stirred vigorously under an atmosphere of hydrogen at 20° C. until 41 of hydrogen had been taken up. The catalyst was then filtered off and and methanol evaporated and replaced with acetone (150 ml). Benzoyl isothiocyanate was then added dropwse (8.5 ml, 63.5 mmol) over 15 min at r.t. and the mixture then heated to reflux for 1.5 h. After cooling the solvent was evaporated and the residue was chromatographed over SiO$_2$ (Merck 230–400 mesh) eluting with CH$_2$Cl$_2$ affording a yellow oil (10 g). This oil was teken up in MeOH (150 ml) and sodium methoxide was added (3.7 g, 69 mmol) and the mixture stirred at 20° C. for 1 h. Following this the solvent was evaporated and the residue dissolved in THF (200 ml) and 2N HCl (100 ml) was added and the mixture stirred for 30 min. EtOAc (200 ml) was then added and the aqueous phase separated and extracted with EtOAc/THF (1:1) (200 ml). The combined organic phases were washed with satd. aq. NaCl solution (2×200 ml), dried, filtered and the solvent evaporated. The solid residue was suspended in ether (100 ml) and filtered off, washed with ether (50 ml) and dried under vacuum (0.05 mmHg, 50° C.) to afford the title compound as a yellow solid (4.7 g, 39% yield). MS: m/e=210.1 (M$^+$).

EXAMPLE 440

2-(4-Methoxy-3-nitro-phenyl)-[1,3]dioxolane

To a solution of 4-methoxy-3-nito-benzaldehyde (11.2 g, 61.8 mmol) in toluene (300 ml) was added ethylene glycol (5.2 ml, 92.7 mmol) and Amberlyst A15 resin acid catalyst (0.6 g). This mixture was stirred vigorously at reflux for 16 h. in a Dean-Stark apparatus. Upon cooling the Amberlyst resn was filtered off and the filtrate washed with satd. aq. NaCl solution (3×150 ml), then dried with Na$_2$SO$_4$, filtered and evaporated to afford the title compound as an orange oil (14 g, 100% yield), MS: m/e=224.1 (M–H)$^-$.

EXAMPLE 441

2-Methoxy-5-(1H-tetrazol-5-yl)-aniline

To a solution of 4-methoxy-3-nitro-benzonitrile (2.5 g, 1.4 mmol) in toluene (20 ml) was added sodium azide (1.3 g, 1.8 mmol) and triethylamine hydrochlride (1.5 g, 1.8 mmol), and this mixture stirred at 100° C. fro 48 h. Water was then added (200 ml) and the mixture agitated, the aqueous phase was further washed with water (2×30 ml). The organic phase was then adjusted to pH 2 and the solid which precipitated was filtered off and washed further with water (100 ml) then dried in vacuo (0.05 mmHg, 60° C.) to afford the crude tetrazole. This material was then directly dissolved in MeOH (80 ml), Pd/C (10%) (250 mg) was added and the mixture stirred under 1 atm of hydrogen at 20° C. for ca. 1 h until the theoretical amount of hydrogen (ca. 880 ml) had been taken up. The catalyst was then filtered off and the solvent evaporated to afford the title compound as a white solid (2.2 g, 82% yield), MS: m/e=191.1 (M$^+$).

Lit: *Synthesis* 1998, p910.

EXAMPLE 442

1-Iodo-3-methoxy-5-nitro-benzene

1-Iodo-3,5-dinitrobenzene (1.8 g, 6.1 mmol) are dissolved in methanol (12 ml) and treated with a solution of sodium methoxide in methanol (5.4M, 1.2 ml). The mixture is then stirred at 65° C. for 52 h. After cooling to ambient temperature, water (50 ml) is added and the mixture extracted three times with ethyl acetate (50 ml). The combined organic layers are extracted with brine (100 ml), dried and evaporated to dryness. Flash chromatography (silica, eluent ethyl acetate/cyclohexane 1:1) affords the product (1.7 g, 99%) as light yellow solid. MS: m/e=279 (M$^+$).

EXAMPLE 443

5-Methoxy-biphenyl-3-yl-amine

3-Methoxy-5-nitro-biphenyl (176 mg, 0.77 mmol) are hydrogenated in ethanol (5 ml) using palladium on carbon (10%, 17 mg) at atmospheric pressure for 2 h. The catalyst is filtered off and the solvent removed in vacuo. Flash chromatography (silica, eluent ethyl acetate/cyclohexane 1:1) affords the product (139 mg, 91%) as a bown oil. MS: m/e=199 (M$^+$).

EXAMPLE 444

2-Methoxy-5-morpholin-4-yl-phenylamine 4-(4-Methoxy-3-nitro-phenyl)-morpholine (6 g) is hydrogenated in dichloromethane (100 ml) and methanol (600 ml) using palladium on carbon (10%, 600 mg) for 12 hours. The catalyst is removed by filtration and the solution evaporated in vacuo. Purification by flash chromatography (silica, eluent ethyl acetate/n-hexane 1:1, then) affords the product as off-white solid (4.6 g, 88%). MS: m/e=209 (M+H$^+$).

EXAMPLE 445

4-(4-Methoxy-3-nitro-phenyl)-morpholine

4-Bromo-2-nitroanisol (8.5 g, 36 mmol), morpholine (3.8 ml, 44 mmol), potassium phosphate (11 g, 51 mmol), 2-biphenyl-dicyclohexyl phosphine (960 mg, 2.7 mmol) and palladium(II)acetate (411 mg, 1.8 mmol) are dissolved in dimethoxyethane (80 ml) and stirred at 80° C. for 96 hours. The mixture is then cooled to room temperature, diluted with ethyl acetate (50 ml) and filtrated through dicalite. Flash chromatography on silica (eluent dichloromethane/methanol 99:1) affords the product as red solid (6.0 g, 69%). MS: m/e=238 (M$^+$).

EXAMPLE 446

3-Methoxy-5-nitro-biphenyl

1-Iodo-3-methoxy-5-nitro-benzene (279 mg, 1 mmol), phenylboronic acid (146 mg, 1.2 mmol), potassium carbonate (2M, 1.0 ml) and tetrakis(triphenylphosphino)palladium (0) are dissolved in ethanol (0.5 ml) and toluene (10 ml) and the mixture heated to 90° C. for 24 h. The volatile components are removed in vacuo and the residue codistilled twice with toluene. Flash chromatography (silica,. eluent dichloromethane/cyclohexane 1:2) affords the product (185 mg, 81%) as light brown solid. MS: m/e=229 (M$^+$).

EXAMPLE 447

5-Bromo-2-methoxy-aniline

A solution of 4-bromo-2-nitro-anisole (7.7 g, 33.1 mmol), triethylamine (4.6 ml, 33.1 mmol) and Raney Nickel catalyst (4 g) was vigorously stirred in ethanol (300 ml) under an atmosphere of hydrogen for 1 h at 20° C. After this time the theoretical amount of hydrogen had been absorbed (2.5 l), so the catalyst was filtered off and the solvent evaporated to afford the title compound as a light yellow solid (7 g, 104% yield), MS: m/e=201 (M$^+$).

Intermediates for the Preparation of Benzylic Amines

EXAMPLE 448

4-Chloromethyl-N-(4-hydroxy-7-morpholin-4-yl-benzothiazol-2-yl)-benzamide

N-(4-Benzyloxy-7-morpholin-4-yl-benzothiazol-2-yl)-4-chloromethyl-benzamide (1.0 g, 2.0 mmol) were dissolved in CH$_2$Cl$_2$ (10 ml) and treated at −78° C. with tetrabutyl ammonium iodide (0.95 g, 2.6 mmol) and a solution of boron trichloride in CH$_2$Cl$_2$ (1M, 7.4 ml). After subsequent warming to 0° and stirring for additional 2 h, ice (2 g) and then water (10 ml) and methanol (2 ml) were added and the phases separated. The aqueous phases were extracted twice with CH$_2$Cl$_2$/MeOH, the combined organic layers were dried with Na$_2$SO$_4$ and evaporated to dryness. Recrystallization from CH$_2$Cl$_2$/MeOH afforded the title compound as an off-white solid (18%). MS: m/e=403 ([M−H$^+$]$^-$).

EXAMPLE 449

4-(1-Bromo-ethyl)-N-(4-methoxy-7-morpholin-4-yl-benzothiazol-2-yl)-benzamide Following the general method of example 1 the title compound was obtained as a yellow solid (63%). MS: m/e=478 (M+H$^+$).

EXAMPLE 450

3-Chloromethyl-N-(4-methoxy-7-morpholin-4-yl-benzothiazol-2-yl)-benzamide

Following the general method of example 1 the title compound was obtained as a light yellow solid (59%). MS: m/e=418 (M+H$^+$).

EXAMPLE 451

4-Chloromethyl-3-fluoro-N-(4-methoxy-7-morpholin-4-yl-benzothiazol-2-yl)-benzamide Following the general method of example 1 the title compound was obtained as a light brown solid (99%). MS: m/e=436 (M+H$^+$).

EXAMPLE 452

4-Chloro-3-chloromethyl-N-(4-methoxy-7-morpholin-4-yl-benzothiazol-2-yl)-benzamide Following the general method of example 1 the title compound was obtained only in 75% purity (68%) and used in the subsequent steps without further purification. MS: m/e=452 (M+H$^+$).

EXAMPLE 453

4-[(2-Methoxy-ethyl)-methyl-sulfamoyl]-benzoic acid

4-Chloro-sulfonyl-benzoic acid (100 mg, 0.45 mmol) were dissolved in (2-methoxy-ethyl)-methyl-amine (1.0 g, 11.2 mmol) and heated to 50° C. for 18 h. Removal of the volatile components in vacuo and flash chromatography (silica, eluent $CH_2Cl_2/MeOH/H_2O/AcOH$ 90:10:1:1) afforded the product as white solid (65%). MS: m/e=272 ([M−H]−).

Intermediates for the Preparation of Benzylic Amines for 2-OBn

EXAMPLE 454

4-Benzyloxy-7-morpholin-4-yl-benzothiazol-2-yl-amine

Using 2-benzyloxy-5-morpholin-4-yl-phenyl)-thiourea following the general method of example 403 the title compound was obtained as off-white solid (69%). MS: m/e=342 (M+H+).

EXAMPLE 455

N-(4-Benzyloxy-7-morpholin-4-yl-benzothiazol-2-yl)-4-chloromethyl-benzamide

Following the general method of example 1 the title compound was obtained as a pale yellow solid (81%). MS: m/e=494 (M+H+).

Intermediates for the Preparation of Benzylic Amines for Changed 7-position

EXAMPLE 456

4-Methoxy-7-thiomorpholin-4-yl-benzothiazol-2-yl-amine

Using 2-methoxy-5-thiomorpholin-4-yl-phenyl)-thiourea following the general method of example 403 the title compound was obtained as light brown solid (31%). MS: m/e=282 (M+H+).

EXAMPLE 457

[4-Methoxy-7-(2-methyl-pyridin-4-yl)-benzothiazol-2-yl]-carbamic acid methyl ester Using the general procedure B the title compound was prepared from 4-methoxy-7-morpholin-4-yl-benzothiazol-2-yl-amine and 2-methyl-4-trimethylstannanyl-pyridine as a white solid (8%). MS: m/e=329 (M+).

EXAMPLE 458

4-Methoxy-7-(2-methyl-pyridin-4-yl)-benzothiazol-2-yl-amine

[4-Methoxy-7-(2-methyl-pyridin-4-yl)-benzothiazol-2-yl]-carbamic acid methyl ester (100 mg, 0.24 mmol) were dissolved in ethyleneglycol (3.0 ml) and treated with potassium hydroxide (528 mg, 1.1 mmol) and heated to 100° C. for 6.5 h. The reaction mixture was cooled to room temperature, diluted with water, neutralized with 1N HCl and extracted four times with ethyl acetate. The organic layers were combined and washed with water and saturated aqueous NaCl. The organic phases were then dried and the solvent removed in vacuo. The product was obtained as a light brown solid (83%). MS: m/e=272 (M+H+).

EXAMPLE A

Tablet Formulation (Wet Granulation)

|      |                         | mg/tablet |       |        |        |
|------|-------------------------|-----------|-------|--------|--------|
| Item | Ingredients             | 5 mg      | 25 mg | 100 mg | 500 mg |
| 1.   | Compound of formula I   | 5         | 25    | 100    | 500    |
| 2.   | Lactose Anhydrous DTG   | 125       | 105   | 30     | 150    |
| 3.   | Sta-Rx 1500             | 6         | 6     | 6      | 30     |
| 4.   | Microcrystalline Cellulose | 30     | 30    | 30     | 150    |
| 5.   | Magnesium Stearate      | 1         | 1     | 1      | 1      |
|      | Total                   | 167       | 167   | 167    | 831    |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

EXAMPLE B

Capsule Formulation

|      |                       | mg/capsule |       |        |        |
|------|-----------------------|------------|-------|--------|--------|
| Item | Ingredients           | 5 mg       | 25 mg | 100 mg | 500 mg |
| 1.   | Compound of formula I | 5          | 25    | 100    | 500    |
| 2.   | Hydrous Lactose       | 159        | 123   | 148    | —      |
| 3.   | Corn Starch           | 25         | 35    | 40     | 70     |
| 4.   | Talc                  | 10         | 15    | 10     | 25     |
| 5.   | Magnesium Stearate    | 1          | 2     | 2      | 5      |
|      | Total                 | 200        | 200   | 300    | 600    |

Manufacturing Procedure
1. Mix items 1, 2 and 3 in a suitable mixer for 30 minutes.
2. Add items 4 and 5 and mix for 3 minutes.
3. Fill into a suitable capsule.

What is claimed is:

1. A method of treating a person having a disease selected from the group consisting of Alzheimer's disease, Parkinson's disease, schizophrenia, neuroprotection, anxiety, ischemia, hypoxia, and epilepsy comprising administering, to the person an effective amount of a compound of the formula

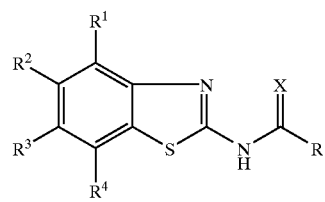

wherein
 $R^1$ is hydrogen, lower alkyl, lower alkoxy, benzyloxy, cycloalkyloxy, halogen, hydroxy or trifluoromethyloxy;
 $R^2$, $R^3$ are independently from each other hydrogen, halogen, lower alkyl or lower alkyloxy;

R$^4$ is a five or six membered aromatic or non aromatic heterocycle, which may be attached to the benzo group via the linker —(O)$_m$—(CH$_2$)$_n$ or —N═C(CH$_3$)— and is unsubstituted or substituted by one or two group(s) R$^7$, wherein R$^7$ is defined below;

R is (CH$_2$)$_n$— six membered aromatic heterocycle, with the exception of the piperazinyl group in case if n=O, which rings are unsubstituted or substituted by one or two substituents, selected from the group consisting of 2-oxo-pyrrolidin, piperidinyl, phenyl, —(CH$_2$)$_n$OH, halogen, CF$_3$, ═O, lower alkyl, cycloalkyl, —(CH$_2$)$_n$—O-lower alkyl, —(CH$_2$)$_n$NH$_2$, —(CH$_2$)$_n$CN, —C(O)O-lower alkyl, —CH$_2$—O—S(O)$_2$CH$_3$, —C(O)-lower alkyl, —C(O)—(CH$_2$)$_n$-lower alkoxy, —CH$_2$—N(R$^6$)C$_6$H$_4$F, —CH$_2$—N(R$^6$)C(O)O-lower alkyl, —N(R$^6$)—C(O)—N(R$^5$)—(CH$_2$)$_n$—O-lower alkyl, or by tetrahydrofuran, substituted by 4-Cl-phenyl, or by piperazin-1-yl, morpholinyl, thiomorpholinyl, thiomorpholin-1-oxo, pyrrolidin-1-yl or by piperidin-1-yl or is benzopiperidin-1-yl or benzothien-2-yl, X is O or S;

R$^5$, R$^6$ are independently from each other hydrogen or lower alkyl,

R$^7$ is lower alkyl, lower alkoxy, —C(O)-lower alkyl, —C(O)O-benzyl, —C(O)O-lower alkyl, —(CH$_2$)$_n$NR$^5$R$^6$, pyridinyl, optionally substituted by lower alkyl, or is —CH$_2$N(R$^5$)—C(O)O-lower alkyl, —NH—C(phenyl)$_3$, pyrrolidinyl, piperidinyl, morpholinyl, piperazinyl, unsubstituted or substituted by lower alkyl;

n is 0, 1, 2, 3 or 4;

m is 0 or 1;

o is 0, 1, 2, 3 or 4;

or a pharmaceutically acceptable salt thereof.

2. The method of claim 1, which comprises administering a compound of formula wherein R$^1$ is hydrogen, lower alkyl, lower alkoxy, halogen, hydroxy or trifluoromethyloxy;

R$^2$, R$^3$ are independently from each other hydrogen, halogen, lower alkyl or lower alkyloxy;

R$^4$ is a five or six membered aromatic or non aromatic heterocycle, which is attached to the benzo group via the linker —(O)$_m$—(CH$_2$)$_n$ and is unsubstituted or substituted by lower alkyl, —C(O)O-benzyl or —NR$^5$R$^6$;

R is —(CH$_2$)$_n$— six membered aromatic heterocycle, with the exception of the piperazinyl group in case if n=O, which rings may be optionally substituted by halogen, hydroxy, lower alkyl, or by piperazin-1-yl, morpholinyl, thiomorpholinyl, thiomorpholin-1-oxo, pyrrolidin-1-yl or by piperidin-1-yl or is benzopiperidin-1-yl or benzothien-2-yl, X is O or S;

R$^5$, R$^6$ are independently from each other hydrogen or lower alkyl, n is 0, 1, 2, 3 or 4;

m is 0 or 1;

o is 0, 1, 2, 3 or 4;

or a pharmaceutically acceptable salt thereof.

3. The method of claim 1, wherein in the compound R$^1$ is methoxy, X is oxygen and R$^2$/R$^3$ are hydrogen.

4. The method of claim 1, wherein the compound is selected from the group consisting of:

N-(4-methoxy-7-thiophen-2-yl-benzothiazol-2-yl)-2-methyl-isonicotinamide,

N-[4-methoxy-7-(2-pyridin-2-yl-thiazol-4-yl)-benzothiazol-2-yl]-2-methyl-isonicotinamide, N-[4-methoxy-7-(2-pyrrolidin-1-yl-thiazol-4-yl)-benzothiazol-2-yl]-2-methyl-isonicotinamide, N-{4-methoxy-7-[2-(4-methyl-piperazin-1-yl)-thiazol-4-yl]-benzothiazol-2-yl}-2-methyl-isonicotinamide, and N-[4-methoxy-7-(5-methyl-thiophen-2-yl)-benzothiazol-2-yl]-2-methyl-isonicotinamide.

5. A composition comprising a pharmaceutically effective amount of the compound of formula I wherein R$^1$ is hydrogen, lower alkyl, lower alkoxy, benzyloxy, cycloalkyloxy, halogen, hydroxy or trifluoromethyloxy;

R$^2$, R$^3$ are independently from each other hydrogen, halogen, lower alkyl or lower alkyloxy;

R$^4$ is a five or six membered aromatic or non aromatic heterocycle, which may be attached to the benzo group via the linker —(O)$_m$—(CH$_2$)$_n$ or —N═C(CH$_3$)— and is unsubstituted or substituted by one or two group(s) R$^7$, wherein R$^7$ is defined below;

R is (CH$_2$)$_n$-six membered aromatic heterocycle, with the exception of the piperazinyl group in case if n=O, which rings are unsubstituted or substituted by one or two substituents, selected from the group consisting of 2-oxo-pyrrolidin, piperidinyl, phenyl, —(CH$_2$)$_n$OH, halogen, CF$_3$, ═O, lower alkyl, cycloalkyl, —(CH$_2$)$_n$—O-lower alkyl, —(CH$_2$)$_n$NH$_2$, —(CH$_2$)$_n$CN, —C(O)O-lower alkyl, —CH$_2$—O—S(O)$_2$CH$_3$, —C(O)-lower alkyl, —C(O)—(CH$_2$)$_n$-lower alkoxy, —CH$_2$—N(R$^6$)C$_6$H$_4$F, —CH$_2$—N(R$^6$)C(O)O-lower alkyl, —N(R$^6$)—C(O)—N(R$^5$)—(CH$_2$)$_n$—O-lower alkyl, or by tetrahydrofuran, substituted by 4-Cl-phenyl, or by piperazin-1-yl, morpholinyl, thiomorpholinyl, thiomorpholin-1-oxo, pyrrolidin-1-yl or by piperidin-1-yl or is benzopiperidin-1-yl or benzothien-2-yl, X is O or S;

R$^5$, R$^6$ are independently from each other hydrogen or lower alkyl,

R$^7$ is lower alkyl, lower alkoxy, —C(O)-lower alkyl, —C(O)O-benzyl, —C(O)O-lower alkyl, —(CH$_2$)$_n$ NR⁵R⁶, pyridinyl, optionally substituted by lower alkyl, or is —CH₂N(R⁵)—C(O)O-lower alkyl, —NH—C(phenyl)₃, pyrrolidinyl, piperidinyl, morpholinyl, piperazinyl, unsubstituted or substituted by lower alkyl;

n is 0, 1, 2, 3 or 4;

m is 0 or 1;

o is 0, 1, 2, 3 or 4;

or a pharmaceutically acceptable salt thereof and a pharmaceutically acceptable excipient.

6. The method of claim 1, wherein the compound is selected from the group consisting of 3-(4-Methoxy-7-morpholin-4-yl-benzothiazol-2-yl)-1-methyl-1-(6-methyl-pyridin-3-ylmethyl)-urea;

N-(4-Methoxy-7-thiophen-2-yl-benzothiazol-2-yl)-2-methyl-isonicotinamide

N-[4-Methoxy-7-(2-pyridin-2-yl-thiazol-4-yl)-benzothiazol-2-yl]-2-methyl-isonicotinamide;

N-[4-Methoxy-7-(2-pyrrolidin-1-yl-thiazol-4-yl)-benzothiazol-2-yl]-2-methyl-isonicotinamide;

N-{4-Methoxy-7-[2-(4-methyl-piperazin-1-yl)-thiazol-4-yl]-benzothiazol-2-yl}-2-methyl-isonicotinamide;

N-[4-Methoxy-7-(5-methyl-thiophen-2-yl)-benzothiazol-2-yl]-2-methyl-isonicotinamide;

N-(4-Methoxy-7-morpholin-4-yl-benzothiazol-2-yl)-2-methyl-isonicotinamide;

2-Chloro-N-(4-methoxy-7-morpholin-4-yl-benzothiazol-2-yl)-6-methyl-isonicotinamide;

2-Chloro-N-(4-methoxy-7-morpholin-4-yl-benzothiazol-2-yl)-isonicotinamide; and

2-Iodo-N-(4-methoxy-7-morpholin-4-yl-benzothiazol-2-yl)-6-methyl-isonicotinamide.

7. The method of claim 1, wherein the compound is N-(4-methoxy-7-thiophen-2-yl-benzothiazol-2-yl)-2-methyl-isonicotinamide.

8. The method of claim 1, wherein the compound is N-[4-methoxy-7-(2-pyridin-2-yl-thiazol-4-yl)-benzothiazol-2-yl]-2-methyl-isonicotinamide.

9. The method of claim 1, wherein the compound is N-[4-methoxy-7-(2-pyrrolidin-1-yl-thiazol-4-yl)-benzothiazol-2-yl]-2-methyl-isonicotinamide.

10. The method of claim 1, wherein the compound is N-{4-methoxy-7-[2-(4-methyl-piperazin-1-yl)-thiazol-4-yl]-benzothiazol-2-yl}-2-isonicotinamide.

11. The method of claim 1, wherein the compound is N-[4-methoxy-7-(5-methyl-thiophen-2-yl)-benzothiazol-2-yl]-2-methyl-isonicotinamide.

12. The method of claim 1, wherein the disease is Alzheimer's disease.

13. The method of claim 1, wherein the disease is Parkinson's disease.

14. The method of claim 1, wherein the disease is schizophrenia.

15. The method of claim 1, wherein the disease is neuroprotection.

16. The method of claim 1, wherein the disease is anxiety.

17. The method of claim 1, wherein the disease is ischemia or hypoxia.

18. The method of claim 1, wherein the disease is epilepsy.

* * * * *

UNITED STATES PATENT AND TRADEMARK OFFICE
CERTIFICATE OF CORRECTION

| | |
|---|---|
| PATENT NO. | : 6,835,732 B2 |
| DATED | : December 28, 2004 |
| INVENTOR(S) | : Alexander Alanine et al. |

It is certified that error appears in the above-identified patent and that said Letters Patent is hereby corrected as shown below:

<u>Title page,</u>
Item [73], Assignee, reads "Hoffman-La Roche Inc., Nutley, NJ (US)" and should read
-- Hoffmann-La Roche Inc., Nutley, NJ (US) --.

Signed and Sealed this

Thirty-first Day of May, 2005

JON W. DUDAS
*Director of the United States Patent and Trademark Office*